US010556943B2

(12) United States Patent
Knutson et al.

(10) Patent No.: US 10,556,943 B2
(45) Date of Patent: Feb. 11, 2020

(54) HLA-DR BINDING PEPTIDES AND THEIR USES

(71) Applicants: Mayo Foundation for Medical Education and Research, Rochester, MN (US); University of Washington, Seattle, WA (US)

(72) Inventors: Keith L. Knutson, Jacksonville, FL (US); Mary L. Disis, Renton, WA (US); John D. Fikes, San Diego, CA (US); Melanie Beebe, Apex, NC (US); Glenn Ishioka, San Diego, CA (US)

(73) Assignees: Mayo Foundation for Medical Education and Research, Rochester, MN (US); University of Washington, Seattle, WA (US)

(*) Notice: Subject to any disclaimer, the term of this patent is extended or adjusted under 35 U.S.C. 154(b) by 137 days.

(21) Appl. No.: 15/381,454

(22) Filed: Dec. 16, 2016

(65) Prior Publication Data

US 2017/0342126 A1 Nov. 30, 2017

Related U.S. Application Data

(63) Continuation of application No. 14/480,365, filed on Sep. 8, 2014, now abandoned, which is a continuation of application No. 12/740,562, filed as application No. PCT/US2008/081799 on Oct. 30, 2008, now abandoned.

(60) Provisional application No. 60/984,646, filed on Nov. 1, 2007.

(51) Int. Cl.
| | | |
|---|---|---|
| A61K 39/00 | (2006.01) | |
| A61K 9/127 | (2006.01) | |
| C07K 14/47 | (2006.01) | |
| C07K 14/71 | (2006.01) | |
| C07K 7/08 | (2006.01) | |
| C07K 14/705 | (2006.01) | |
| A61K 38/00 | (2006.01) | |

(52) U.S. Cl.
CPC ............ *C07K 14/71* (2013.01); *C07K 7/08* (2013.01); *C07K 14/4738* (2013.01); *C07K 14/4743* (2013.01); *C07K 14/4748* (2013.01); *C07K 14/70503* (2013.01); *A61K 38/00* (2013.01); *A61K 2039/572* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,722,848 A | 2/1988 | Paoletti et al. | |
| 4,837,028 A | 6/1989 | Allen | |
| 5,019,369 A | 5/1991 | Presant et al. | |
| 5,204,253 A | 4/1993 | Sanford et al. | |
| 5,279,833 A | 1/1994 | Rose | |
| 5,580,859 A | 12/1996 | Felgner et al. | |
| 5,589,466 A | 12/1996 | Felgner et al. | |
| 5,679,647 A | 10/1997 | Carson et al. | |
| 5,736,142 A | 4/1998 | Sette et al. | |
| 5,736,524 A | 4/1998 | Content et al. | |
| 5,739,118 A | 4/1998 | Carrano et al. | |
| 5,804,566 A | 9/1998 | Carson et al. | |
| 5,922,687 A | 7/1999 | Mann et al. | |
| 7,462,354 B2 | 12/2008 | Sette et al. | |
| 2003/0224036 A1 | 12/2003 | Fikes et al. | |
| 2004/0121946 A9 | 6/2004 | Fikes et al. | |
| 2007/0098776 A1 | 5/2007 | Fikes et al. | |

FOREIGN PATENT DOCUMENTS

| | | |
|---|---|---|
| EP | 1 806 359 | 7/2007 |
| WO | WO 1991/006309 | 5/1991 |
| WO | WO 1993/024640 | 12/1993 |
| WO | WO 1994/003205 | 2/1994 |
| WO | WO 1994/020127 | 9/1994 |
| WO | WO 1995/007707 | 3/1995 |
| WO | WO 1996/018372 | 6/1996 |
| WO | WO 1997/033602 | 9/1997 |
| WO | WO 1998/004720 | 2/1998 |
| WO | WO 1999/058658 | 11/1999 |
| WO | WO 1999/061916 | 12/1999 |
| WO | WO 2001/041741 | 6/2001 |
| WO | WO 2001/041787 | 6/2001 |
| WO | WO 2004/094454 | 11/2004 |
| WO | WO 2005/012502 | 2/2005 |

OTHER PUBLICATIONS

Cid and Anton (Crit. Rev. Oncol. Hematol. 2013, 85: 350-362) (Year: 2013).*
Alexander et al., "Derivation of HLA-A11/Kb transgenic mice: functional CTL repertoire and recognition of human A11-restricted CTL epitopes," *J. Immunol.*, 1997, 159:4753-4761.
Alonso et al., "Biodegradable Microspheres as Controlled Release Tetanus Toxoid Delivery Systems," *Vaccine*, 1994, 12:299-306.

(Continued)

*Primary Examiner* — Michael Szperka
*Assistant Examiner* — Marianne DiBrino
(74) *Attorney, Agent, or Firm* — Fish & Richardson P.C.

(57) ABSTRACT

The present invention provides HLA-DR (MHC class II) binding peptides derived from the ovarian/breast cancer associated antigens, Human Epidermal Growth Factor Receptor 2 (HER-2/neu), Carcinoembryonic Antigen (CEA), Insulin Growth Factor Binding Protein 2 (IGFBP-2), and Cyclin D1. The immunogenic peptides can be used in cancer vaccines.

10 Claims, 6 Drawing Sheets

Specification includes a Sequence Listing.

(56) References Cited

OTHER PUBLICATIONS

Altman et al., "Phenotypic Analysis of Antigen-Specific T Lymphocytes," *Science*, 1996, 174:94-96.
Arndt et al., "Selection of the MHC class II-associated peptide repertoire by HLA-DM," *Immunol. Res.*, 1997, 16:261-272.
Babbitt et al., "Binding of immunogenic peptides to Ia histocompatibility molecules ," *Nature*, 1985, 317:359.
Bertoni et al., "Human Class I Supertypes and CTL Repertoires Extend to Chimpanzees," *J. Immunol.*, 1998, 161:4447-4455.
Bertoni et al., "Human Histocompatibility Leukocyte Antigen-binding Supermotifs Predict Broadly Cross-reactive Cytotoxic T Lymphocyte Responses in Patients with Acute Hepatitis," *J. Clin. Invest.*, 1997, 100:503-513.
Blum et al., "Antigen-presenting cells and the selection of immunodominant epitopes," *Crit. Rev. Immunol.*, 1997, 17:411-417.
Boog, "Stimulation with dendritic cells decreases or obviates the CD4l helper cell requirement in cytotoxic T lymphocyte responses," *Eur. J. Immunol.*, 1988, 18:219.
Busch et al., "Degenerate binding of immunogenic peptides to HLA-DR proteins on B cell surfaces," *Int. Immunol.*, 1990, 2:443-451.
Buus et al., "Isolation and characterization of antigen-Ia complexes involved in T cell recognition," *Cell*, 1986, 47:1071-1077.
Cease and Berzofsky, "Toward a vaccine for AIDS: the emergence of immunobiology-based vaccine development," *Annu. Rev. Immunol.*, 1994, 12:923-989.
Celis et al., "Induction of anti-tumor cytotoxic T lymphocytes in normal humans using primary cultures and synthetic peptide epitopes," *Proc. Natl. Acad. Sci. USA*, 1994, 91:2105-2109.
Ceppellini et al., "Binding of labelled influenza matrix peptide to HLA DR in living B lymphoid cells," *Nature* , 1989, 339:392-394.
Cerundolo et al., "The binding affinity and dissociation rates of peptides for class I major histocompatibility complex molecules," *J Immunol.*, 1991, 21:2069-2075.
Chakrabarti et al., "Expression of the HTLV-III envelope gene by a recombinant vaccinia virus," *Nature*, 1986, 320:535-537.
Chanda et al., "High level expression of the envelope glycoproteins of the human immunodeficiency virus type I in presence of rev gene using helper-independent adenovirus type 7 recombinants," *Virology*, 1990, 175:535-547.
Christnick et al., "Peptide binding to class I MHC on living cells and quantitation of complexes required for CTL lysis," *Nature*, 1991, 352:67-70.
De Bruijn et al., "Peptide loading of empty major histocompatibility complex molecules on RMA-S cells allows the induction of primary cytotoxic T lymphocyte responses," *Eur. J. Immunol.*, 1991, 21:2963-2970.
Del Guercio et al., "Binding of a peptide antigen to multiple HLA alleles allows definition of an A2-like supertype," *J Immunol.*, 1995, 154:685.
Deres et al., "In vivo priming of virus-specific cytotoxic T lymphocytes with synthetic lipopeptide vaccine," *Nature*, 1989, 342:561-564.
Dermer, "Another anniversary for the war on cancer," *Bio/Technology*, vol. 12, p. 320, Mar. 12, 1994.
Diepolder et al., "Immunodominant CD4+ T-cell epitope within non-structural protein 3 in acute hepatitis C virus infection," *J. Virol.*, 1997, 71:6011-6019.
Disis et al., "Generation of immunity to the HER-2/neu oncogenic protein in patients with breast and ovarian cancer using a peptide-based vaccine," *Clin Cancer Res.*, 1999, 5:1289-1297.
Disis et al., "Generation of T-cell immunity to the HER-2/neu protein after active immunization with HER-2/neu peptide-based vaccines," *J Clin Oncol.*, 20(11):2624-2632, Jun. 1, 2002.
Disis et al., "Maximizing the retention of antigen specific lymphocyte function after cryopreservation," *J Immunol Methods*, 308(1-2):13-18, Epub Oct. 21, 2005.

Disis et al., "Peptide Based, but not Whole Protein, Vaccines Elicit Immunity to HER-2/neu, an Oncogenic Self Protein," *J. Immunol.*, 1996, 156:3151-3158.
Doolan et al., "Degenerate cytotoxic T cell epitopes from P. falciparum restricted by multiple HLA-A and HLA-B supertype alleles," *Immunity*, 1997, 7:97-112.
Dzuris et al., "Conserved MHC class I peptide binding motif between humans and rhesus macaques," *J Immunol.*, 2000, 164:283-291.
Eldridge et al., "Biodegradable microspheres as a vaccine delivery system," *Mol. Immunol.*, 1991, 28:287-294.
Eldridge et al., "New advances in vaccine delivery systems," *Sem. Hematol.*, 1993, 30:16-25.
Falk et al., "Allele-specific motifs revealed by sequencing of self-peptides eluted from MHC molecules," *Nature*, 351(6324):290-296, May 23, 1991.
Falo et al., "Targeting antigen into the phagocytic pathway in vivo induces protective tumour immunity," *Nature Med.*, 1995, 7:649-653.
Felgner et al., "Lipofection: a highly efficient, lipid-mediated DNA-transfection procedure," *Proc. Natl. Acad. Sci. USA*, 1987, 84:7413-7414.
Fournier and Schirrmacher, "Randomized clinical studies of anti-tumor vaccination: state of the art in 2008," *Expert Rev Vaccines*, 8(1):51-66, Jan. 2009.
Freshney, *Culture of Animal Cells, A Manual of Basic Technique*, Alan R. Liss, Inc., 1983, New York, p. 4.
Geluk et al., "HLA-DR3 molecules can bind peptides carrying two alternative specific submotifs," *J. Immunol.*, 1994, 152:5742.
Germain, "The biochemistry and cell biology of antigen processing and presentation," *Annu. Rev. Immunol.*, 1993, 11:403-450.
Hammer et al., "Precise prediction of major histocompatibility complex class II peptide interactions based on side chain scanning," *J. Exp. Med.*, 1994, 180:2353-2358.
Hammer et al., "Promiscuous and allele-specific anchors in HLA-DR-binding peptides," *Cell*, 1993, 74:197.
Hill et al., "Conformational and structural characteristics of peptides binding to HLA-DR molecules," *J Immunol.*, 1991, 147:189.
Hill et al., "Exploration of requirements for peptide binding to HLA DRB1*0101 and DRB1*0401," *J Immunol.*, 1994, 152:2890.
Hu et al., "Expression of AIDS virus envelope gene in recombinant vaccinia viruses," *Nature*, 1986, 320:537-540.
Hu et al., "The immunostimulating complex (ISCOM) is an efficient mucosal delivery system for respiratory syncytial virus (RSV) envelope antigens inducing high local and systemic antibody responses," *Clin Exp Immunol.*, 1998, 113:235-224.
Hunkapiller et al., "High-sensitivity sequencing with a gas-phase sequenator," *Methods Enzymol.*, 1983, 91:399-413.
Hunt et al., "Characterization of peptides bound to the class I MHC molecule HLA-A2.1 by mass spectrometry," *Science*, 1992, 255:1261-1263.
Inaba et al., "Direct activation of $CD8^+$ cytotoxic T lymphocytes by dendritic cells," *J. Exp. Med.*, 1987, 166:182.
Jones et al., "Protection of mice from Bordetella pertussis respiratory infection using microencapsulated pertussis fimbriae," *Vaccine*, 1995, 13:675-681.
Kalli et al., "An HLA-DR-degenerate epitope pool detects insulin-like growth factor binding protein 2-specific immunity in patients with cancer," *Cancer Res.*, Jun. 15, 2008, 68(12):4893-4901.
Kawashima et al., "The multi-epitope approach for immunotherapy for cancer: identification of several CTL epitopes from various tumor-associated antigens expressed on solid epithelial tumors," *Human Immunol.*, 1998, 59(1):1-14.
Khilko et al., "Direct detection of major histocompatibility complex class I binding to antigenic peptides using surface plasmon resonance. Peptide immobilization and characterization of binding specificity," *J Biol. Chem.*, 1993, 268:15425-15434.
Kieny et al., "AIDS virus ENV protein expressed from a recombinant Vaccinia virus," *AIDS Bio/Technology*, 1986, 4:790.
Klebanoff et al., "Therapeutic cancer vaccines: are we there yet?" *Immunol Rev.*, 239(1):27-44, Jan. 2011.

(56) References Cited

OTHER PUBLICATIONS

Knutson et al., "T-Cell Immunity to the Folate Receptor Alpha Is Prevalent in Women With Breast or Ovarian Cancer," *J Clin Oncol.*, 2006, 24:4254-4261.
Kofler et al., "Preparation and characterization of poly-($^{D,L}$-lactide-co-glycolide) and poly-($^{L}$-lactic acid) microspheres with entrapped pneumotropic bacterial antigens," *J Immunol. Methods*, 1996, 192:2.
Madden, "The 3-dimensional structure of peptide-MHC complexes," *Ann. Rev. Immunol.*, 1995, 13:587-622.
Mannino and Gould-Fogerite, "Liposome mediated gene transfer," *BioTechniques*, 1988, 6(7):682-691.
Marshall et al., "Role of the polymorphic residues in HLA-DR molecules in allele-specific binding of peptide ligands," *J Immunol.*, 1994, 152:4946-4957.
Matteucci et al., "Synthesis of deoxynucleotides on a polymer support," *J. Am. Chem. Soc.*, 1981, 103:3185-3191.
Mora and Tam, "Controlled Lipidation and Encapsulation of Peptides as a Useful Approach to Mucosal Immunizations," *J. Immunol.*, 1998, 161:3616-3623.
NIH National Cancer Institute, "What are vaccines?" Nov. 15, 2011, 12 pages.
O'Sullivan et al., "On the interaction of promiscuous antigenic peptides with different DR alleles. Identification of common structural motifs," *J. Immunol.*, 1991, 147:2663.
Ogg et al., "Quantitation of HIV-1-specific cytotoxic T lymphocytes and plasma load of viral RNA," *Science*, 1998, 279:2103-2106.
Pamer et al., "Precise prediction of a dominant class I MHC-restricted epitope of Listeria monocytogenes," *Nature*, 1991, 353:852-955.
Pazo Cid and Antón, "Advanced HER2-positive gastric cancer: current and future targeted therapies," *Crit Rev Oncol Hematol.*, 85(3):350-362, Epub Sep. 26, 2012.
Perez et al., "HER-2/neu-derived peptide 884-899 is expressed by human breast, colorectal and pancreatic adenocarcinomas and is recognized by in-vitro-induced specific CD4)+) T cell clones," *Cancer Immunol. Immunother.*, Jan. 2002, 50(11):615-624, Epub Nov. 23, 2001.
Perkus and Paoletti, "Recombinant virus as vaccination carrier of heterologous antigens," *Concepts in Vaccine Development*, p. 379, Kaufmann, ed., Walter de Gruyter and Co., Berlin.
Press et al., "Expression of the HER-2/neu proto-oncogene in normal human adult and fetal tissues," *Oncogene*, 5(7):953-962, Jul. 1990.
Reay et al., "pH dependence and exchange of high and low responder peptides binding to a class II MHC molecule," *EMBO J*, 1992, 11:2829-2839.
Reddy et al., "In vivo cytotoxic T lymphocyte induction with soluble proteins administered in liposomes" *J. Immunol.*, 1992, 148:1585-1589.
Rehermann et al., "The cytotoxic T lymphocyte response to multiple hepatitis B virus polymerase epitopes during and after acute viral hepatitis," *J. Exp. Med.*, 1995, 181:1047-1058.
Robinson et al., "Protection against a lethal influenza virus challenge by immunization with a haemagglutinin-expressing plasmid DNA," *Vaccine*, 1993, 11:957-960.
Rock, "A new foreign policy: MHC class I molecules monitor the outside world," *Immunol. Today* 17(3):131-137, Mar. 1996.
Rupert et al., "Prominent role of secondary anchor residues in peptide binding to HLA-A2.1 molecules," *Cell*, 1993, 74:929-937.
Salazar et al., "Immunization of cancer patients with HER-2/neu-derived peptides demonstrating high-affinity binding to multiple class II alleles," *Clin Cancer Res.*, Nov. 15, 2003, 9(15):5559-5565.
Schaeffer et al., "Relative contribution of "determinant selection" and "holes in the T-cell repertoire" to T-cell responses," *Proc. Natl. Acad. Sci. USA*, 1989, 86:4649-4653.
Schreiber et al., "Tumor immunogenicity and responsiveness to cancer vaccine therapy: the state of the art," *Semin Immunol.*, 22(3):105-112, Epub Mar. 11, 2010.
Sercarz et al., "Dominance and crypticity of T cell antigenic determinants," *Annu. Rev. Immunol.*, 1993, 11:729-766.
Sette et al., "HLA DR4w4-binding motifs illustrate the biochemical basis of degeneracy and specificity in peptide-DR interactions," *J. Immunol.*, 1993, 151:3163-3170.
Sette et al., "Prediction of major histocompatibility complex binding regions of protein antigens by sequence pattern analysis ," *Proc Natl Acad Sci USA*, 1989, 86:3296-3300.
Sette et al., "Random association between the peptide repertoire of A2.1 class I and several different DR class II molecules," *J. Immunol.*, 1991, 141:3893-3900.
Sette et al., "Structural analysis of peptides capable of binding to more than one Ia antigen," *J Immunol.*, 1989, 142:35-40.
Sette et al., "The relationship between class I binding affinity and immunogenicity of potential cytotoxic T cell epitopes," *J. Immunol.*, 1994, 153:5586-5592.
Shiver et al., "Naked DNA Vaccination," In: *Concepts in vaccine development*, Kaufmann, S. H. E., ed., p. 423-436, 1996.
Sidney et al., "Definition of an HLA-A3-like supermotif demonstrates the overlapping peptide-binding repertoires of common HLA molecules," *Hum. Immunol.* 1996, 45:79-93.
Sidney et al., "Measurement of MHC/peptide interactions by gel filtration," *Curr Protocols Immunol.*, 1998, 18:18.3.2-.3.9.
Sidney et al., "Several HLA alleles share overlapping peptide specificities," *J. Immunol.*, 1995, 154:247.
Southwood et al., "Several Common HLA-DR Types Share Largely Overlapping Peptide Binding Repertoires," *J. Immunol.* 1998, 160:3363-3373.
Stover et al., "New use of BCG for recombinant vaccines," *Nature*, 1991, 351:456-460.
Szoka et al., "Comparative properties and methods of preparation of lipid vesicles (liposomes)," *Ann. Rev. Biophys. Bioeng.*, 1980, 9:467-508.
Takahashi et al., "Induction of CD8+ cytotoxic T cells by immunization with purified HIV-1 envelope protein in ISCOMs," *Nature*, 1990, 344:873-875.
Tam, "Recent advances in multiple antigen peptides," *J. Immunol Methods*, 1996, 196:17-32.
Tam, "Synthetic peptide vaccine design: synthesis and properties of a high-density multiple antigenic peptide system," *Proc. Natl. Acad. Sci. USA*, 1988, 85:5409-5413.
Threlkeld et al., "Degenerate and promiscuous recognition by CTL of peptides presented by the MHC class I A3-like superfamily: implications for vaccine development," *J. Immunol.*, 1997, 159:1648-1657.
Top et al., "Immunization with live types 7 and 4 adenovirus vaccines. I. Safety, infectivity, antigenicity, and potency of adenovirus type 7 vaccine in humans," *J Infect. Dis.*, 1971, 124:148-154.
Townsend and Bodmer, "Antigen recognition by class I-restricted T lymphocytes," *Annu. Rev. Immunol.*, 1989, 7:601-624.
Townsend et al., "Assembly of MHC class I molecules analyzed in vitro," *Cell*, 1990, 62:285-295.
Tsai et al., "Identification of subdominant CTL epitopes of the gp100 melanoma associated tumor antigen by primary in vitro immunization with peptide-pulsed dendritic cells," *J. Immunol.*, 1997, 158:1796-7802.
Tsang et al., "Generation of human cytotoxic T cells specific for human carcinoembryonic antigen epitopes from patients immunized with recombinant vaccinia-CEA vaccine," *J. Natl. Cancer Inst.*, 1995, 87:982-990.
Ulmer et al., "Heterologous protection against influenza by injection of DNA encoding a viral protein," *Science*, 1993, 259:1745.
Verhoef et al., "Des-enkephalin-γ-endorphin (DEγE): Biotransformation in rat, dog and human plasma," *Eur. J. Drug Metab. Pharmacokin.* 1986, 11(4):291-302.
Vitiello et al., "Development of a lipopeptide-based therapeutic vaccine to treat chronic HBV infection. I. Induction of a primary cytotoxic T lymphocyte response in humans," *J. Clin. Invest.*, 1995, 95:341-349.
Warren et al., "Current Status of Immunological Adjuvants," *Annu. Rev. Immunol.*, 1986, 4:369-388.
Wentworth et al., "Differences and similarities in the A2.1-restricted cytotoxic T cell repertoire in humans and human leukocyte antigen-transgenic mice," *J. Immunol.*, 1996, 26:97-101.

(56) References Cited

OTHER PUBLICATIONS

Wentworth et al., "In vitro induction of primary, antigen-specific CTL from human peripheral blood mononuclear cells stimulated with synthetic peptides," *Mol. Immunol.*, 32:603-612.
Wentworth et al., Identification of A2-restricted hepatitis C virus-specific cytotoxic T lymphocyte epitopes from conserved regions of the viral genome, *Int. Immunol.*, 1996, 8:651-659.
Wolff et al., "Direct gene transfer into mouse muscle in vivo ," *Science*, 1990, 247:1465-1468.
Zips et al., "New anticancer agents: in vitro and in vivo evaluation," *In Vivo*, 19(1):1-7, Jan.-Feb. 2005.
European Search Report in Application No. 08843542.5, dated Jul. 5, 2011, 8 pages.
Extended European Search Report in Application No. 16160535.7, dated Jul. 6, 2016, 5 pages.
International Preliminary Report on Patentability in International Application No. PCT/US2008/081799, dated May 4, 2010, 7 pages.
International Search Report and Written Opinion of the International Searching Authority in International Application No. PCT/US2008/081799, dated Sep. 1, 2009, 17 pages.
Search Report in Chinese Application No. 200880124030.6, dated Feb. 5, 2013, 5 pages.
Canadian Office Action in Canadian Application No. 2991175 dated Jun. 7, 2019, 7 pages.

\* cited by examiner

IGFBP-2

HLA-DR BINDING PEPTIDES AND THEIR USES

CROSS-REFERENCE TO RELATED APPLICATIONS

This application is a continuation of U.S. application Ser. No. 14/480,365, filed Sep. 8, 2014 (Abandoned), which is a continuation of U.S. application Ser. No. 12/740,562, filed Aug. 24, 2010 (Abandoned), which is a National Stage application under 35 U.S.C. § 371 that claims the benefit of PCT/US2008/081799, filed Oct. 3, 2008, which claims benefit of priority from U.S. Provisional Application Ser. No. 60/984,646, filed on Nov. 1, 2007. The disclosures of the prior applications are considered part of (and are incorporated by reference in) the disclosure of this application.

STATEMENT AS TO FEDERALLY SPONSORED RESEARCH

This invention was made with government support under CA107590 and CA015083 awarded by the National Institutes of Health. The government has certain rights in the invention.

BACKGROUND OF THE INVENTION

Field of Invention

The present invention relates to compositions and methods for preventing, treating or diagnosing a number of pathological states such as cancers. In particular, it provides novel peptides capable of binding selected major histocompatibility complex (MHC) molecules and induce an immune response.

MHC molecules are classified as either Class I or Class II molecules. Class II MHC molecules are expressed primarily on cells involved in initiating and sustaining immune responses, such as T lymphocytes, B lymphocytes, dendritic cells, macrophages, etc. Class II MHC molecules are recognized by helper T lymphocytes and induce proliferation of helper T lymphocytes and amplification of the immune response to the particular immunogenic peptide that is displayed. Complexes between a particular disease-associated antigenic peptide and class II HLA molecules are recognized by helper T lymphocytes and induce proliferation of helper T lymphocytes and amplification of specific CTL and antibody immune responses.

A complex of an HLA molecule and a peptidic antigen acts as the ligand recognized by HLA-restricted T cells (Buus, S. et al., Cell 47:1071, 1986; Babbitt, B. P. et al., Nature 317:359, 1985; Townsend, A. and Bodmer, H., Annu. Rev. Immunol. 7:601, 1989; Germain, R. N., Annu. Rev. Immunol. 11:403, 1993).

Peptides of the present invention comprise epitopes that bind to HLA class II DR molecules. A greater degree of heterogeneity in both size and binding frame position of the motif, relative to the N- and C-termini of the peptide, exists for class II peptide ligands. This increased heterogeneity of HLA class II peptide ligands is due to the structure of the binding groove of the HLA class II molecule which, unlike its class I counterpart, is open at both ends. Crystallographic analysis of HLA class II DRB*0101-peptide complexes showed that the major energy of binding is contributed by peptide residues complexed with complementary pockets on the DRB*0101 molecules. An important anchor residue engages the deepest hydrophobic pocket (see, e.g., Madden, D. R. Ann. Rev. Immunol. 13:587, 1995) and is referred to as position 1 (P1). P1 may represent the N-terminal residue of a class II binding peptide epitope, but more typically is flanked towards the N-terminus by one or more residues. Other studies have also pointed to an important role for the peptide residue in the sixth position towards the C-terminus, relative to P1, for binding to various DR molecules.

In the past few years evidence has accumulated to demonstrate that a large fraction of HLA class I and class II molecules can be classified into a relatively few supertypes, each characterized by largely overlapping peptide binding repertoires, and consensus structures of the main peptide binding pockets. Thus, peptides of the present invention are identified by any one of several HLA-specific amino acid motifs, or if the presence of the motif corresponds to the ability to bind several allele-specific HLA molecules, a supermotif. The HLA molecules that bind to peptides that possess a particular amino acid supermotif are collectively referred to as an HLA "supertype." Because human population groups, including racial and ethnic groups, have distinct patterns of distribution of HLA alleles it will be of value to identify motifs that describe peptides capable of binding more than one HLA allele, so as to achieve sufficient coverage of all population groups. The present invention addresses these and other needs.

T lymphocytes recognize an antigen in the form of a peptide fragment bound to the MHC class I or class II molecule rather than the intact foreign antigen itself. Antigens presented by MHC class II molecules are usually soluble antigens that enter the antigen presenting cell via phagocytosis, pinocytosis, or receptor-mediated endocytosis. Once in the cell, the antigen is partially degraded by acid-dependent proteases in endosomes. The resulting fragments or peptide associate with the MHC class II molecule after the release of the CLIP fragment to form a stable complex that is then transported to the surface for potential recognition by specific HTLs. See Blum, et al., Crit. Rev. Immunol., 17: 411-17 (1997); Arndt, et al., Immunol. Res., 16: 261-72 (1997).

Peptides that bind a particular MHC allele frequently will fit within a motif and have amino acid residues with particular biochemical properties at specific positions within the peptide. Such residues are usually dictated by the biochemical properties of the MHC allele. Peptide sequence motifs have been utilized to screen peptides capable of binding MHC molecules (Sette, et al., Proc. Natl. Acad. Sci. USA 86:3296 (1989)), and it has previously been reported that class I binding motifs identified potential immunogenic peptides in animal models (De Bruijn, et al., Eur. J. Immunol. 21: 2963-70 (1991); Pamer, et al., Nature 353: 852-955 (1991)). Also, binding of a particular peptide to a MHC molecule has been correlated with immunogenicity of that peptide (Schaeffer, et al., Proc. Natl. Acad. Sci. USA 86:4649 (1989)).

Accordingly, while some MHC binding peptides have been identified, there is a need in the art to identify novel MHC binding peptides from tumor associated antigens that can be utilized to generate an immune response in vaccines against these targets. Further, there is a need in the art to identify peptides capable of binding a wide array of different types of MHC molecules such they are immunogenic in a large fraction a human outbred population.

One of the most formidable obstacles to the development of broadly efficacious peptide-based immunotherapeutics has been the extreme polymorphism of HLA molecules. Effective coverage of a population without bias would thus be a task of considerable complexity if epitopes were used specific for HLA molecules corresponding to each individual allele because a huge number of them would have to be used in order to cover an ethnically diverse population. There exists, therefore, a need to develop peptide epitopes that are bound by multiple HLA antigen molecules at high affinity for use in epitope-based vaccines. The greater the number of HLA antigen molecules bound, the greater the breadth of population coverage by the vaccine. Analog peptides may be engineered based on the information disclosed herein and thereby used to achieve such an enhancement in breadth of population coverage.

BRIEF DESCRIPTION OF THE DRAWINGS

FIG. 2 is identical to FIG. 1 with the only exception that CEA is the antigen. Seven candidate peptides were identified.

FIG. 3 is identical to FIG. 1 with the only exception that IGFBP2 is the antigen. Four candidate peptides were identified. Note that only 10 peptides were assessed as explained in the text above.

FIG. 4 is identical to FIG. 1 with the only exception that Cyclin D1 is the antigen. Using the more liberal statistical method, 7 potential epitopes were identified.

FIG. 6 is identical to FIG. 5 except that the results were obtained using IGFBP-2 derived helper epitopes.

BRIEF SUMMARY OF THE INVENTION

Figure 1:
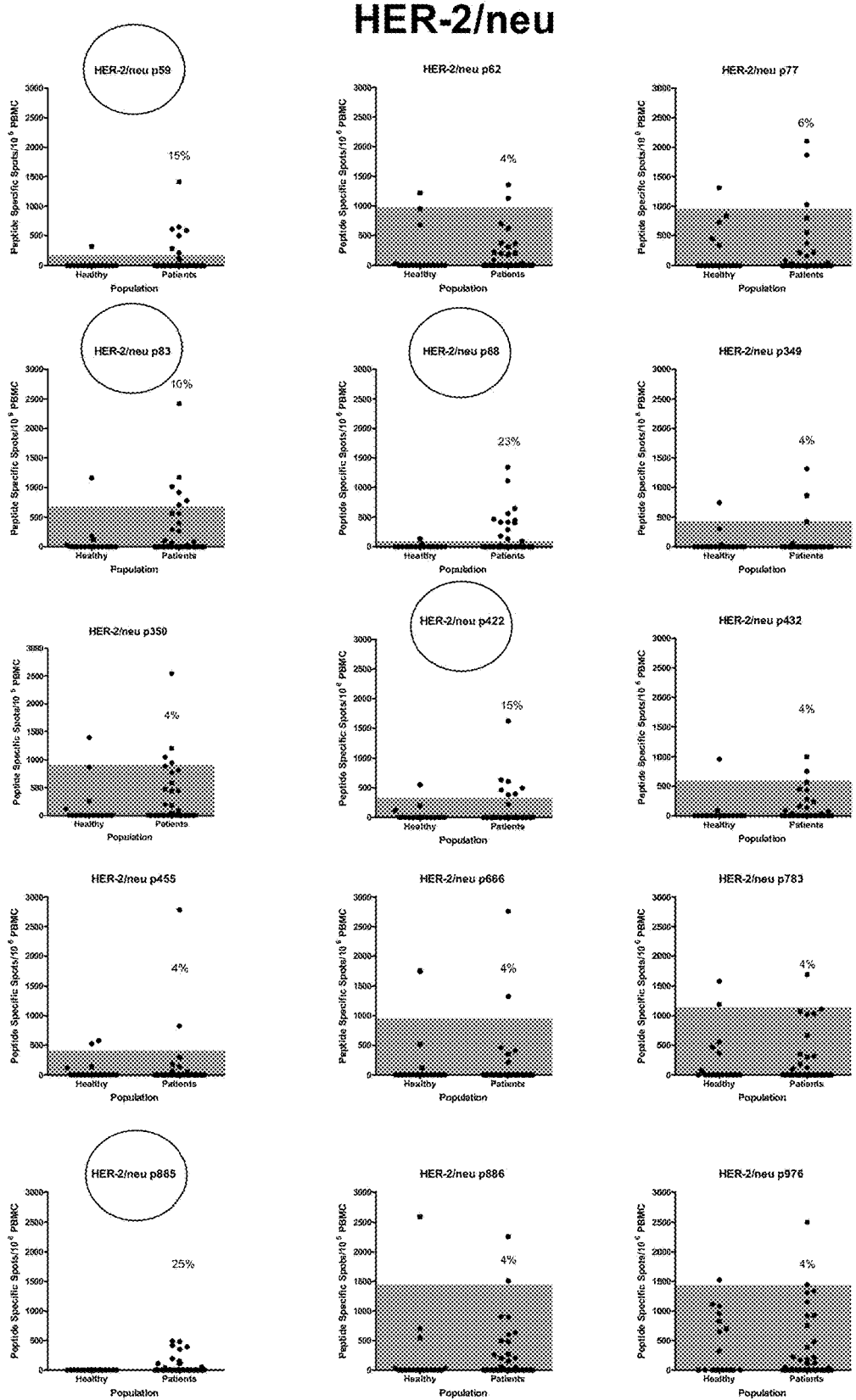
FIG. 1 shows the identification of preexistent immunity to promiscuous HER-2/neu HLA-DR epitopes. Each panel shows a scatter gram of the mean numbers of T cells specific for one of the identified HER-2/neu (see header of each panel) peptides in both healthy volunteer donors and patients. Each panel represents a unique peptide and each data point is derived from one individual. The grey box (i.e. cutoff) delineates the region that constitutes the mean and two standard deviations calculated from the normal healthy individuals. The percentages represent the fraction of patients that had mean T cell values above the cutoff. The peptides that are circled are those in which a higher fraction of the patients responded compared to the normal healthy controls. These peptides are considered to be the best vaccine candidates. However, it is clear that the rigidness of this approach could potentially result in many false negatives. For example, while p885 was shown to be recognized by 25% of patients, p886, a nearly identical peptide was found to be recognized by only 4%. However, if one looks at the graph for p886, there is a healthy individual that showed a robust response. The exclusion of that data point would have resulted in a patient response rate of 15%, which would have been consistent with the p885 response. Despite this, we identified 5 candidates to move forward. The fidelity of this approach is evident from a prior study which has already shown that a HER-2/neu peptide, p884-899, which encompasses the binding motif of p885, is an HLA-DR4 epitope.

The present invention relates to compositions and methods for preventing, treating or diagnosing a number of pathological states such as viral diseases and cancers. Thus, provided herein are novel peptides capable of binding selected major histocompatibility complex (MHC) molecules and inducing or modulating an immune response. Some of the peptides disclosed are capable of binding human class II MHC (HLA) molecules, including HLA-DR and HLA-DQ alleles. Also provided are compositions that include immunogenic peptides having binding motifs specific for MHC molecules. The peptides and compositions disclosed can be utilized in methods for inducing an immune response, a helper T lymphocyte (HTL) response, or a cytotoxic T lymphocyte (CTL) response when administered to a system.

Epitopes on a number of immunogenic tumor associated antigens have been identified. The peptides are thus useful in pharmaceutical compositions for both in vivo and ex vivo therapeutic and diagnostic applications (e.g., tetramer reagents; Beckman Coulter).

The peptides are also useful as epitope-based vaccines. The epitope-based vaccines preferably have enhanced, typically broadened, population coverage. The HLA-DR supermotif-bearing epitopes comprising the vaccine composition preferably bind to more than one HLA DR supertype molecule with a $K_D$ of less than 1000 nM or 500 nM, and stimulate a HTL response in patients bearing an HLA DR supertype allele to which the peptide binds.

Motif-bearing peptides may additionally be used as diagnostic, rather than immunogenic, reagents to evaluate an immune response. For example, an HLA-DR supermotif-bearing peptide epitope may be used prognostically to analyze an immune response for the presence of specific HTL populations from patients who possess an HLA DR supertype allele bound by the peptide epitope.

The binding affinity of a peptide epitope in accordance with the invention for at least one HLA DR supertype molecule is preferably determined. A preferred peptide epitope has a binding affinity of less than 1000 nM, or more preferably less than 500 nM for the at least one HLA DR supertype molecule, and most preferably less than 50 nM.

Synthesis of a HLA DR supermotif-containing epitope may occur in vitro or in vivo. In a preferred embodiment, the peptide is encoded by a recombinant nucleic acid and expressed in a cell. The nucleic acid may encode one or more peptides, at least one of which is an epitope of the invention.

A peptide epitope of the invention, in the context of an HLA DR supertype molecule to which it binds, can be contacted, either in vitro or in vivo, with a cytotoxic T lymphocyte and thereby be used to elicit a T cell response in an HLA-diverse population.

An HTL epitope may be comprised by a single peptide. Further, the HTL epitope may be lipidated, preferably with palmitic acid, and may be linked by a spacer molecule to another HTL epitope or a CTL epitope. The epitope may be expressed by a nucleotide sequence; in a preferred embodiment the nucleotide sequence is comprised in an attenuated viral host.

As will be apparent from the discussion below, other embodiments of methods and compositions are also within the scope of the invention. Further, novel synthetic peptides produced by any of the methods described herein are also part of the invention.

The present invention provides peptides and nucleic acids encoding them for use in vaccines and therapeutics. The invention provides methods of inducing a helper T cell response against a preselected antigen in, a patient, the method comprising contacting a helper T cell with an immunogenic peptide of the invention. The peptides of the invention may be derived from a number of tumor associated antigens. The methods of the invention can be carried out in vitro or in vivo. In a preferred embodiment the peptides are contacted with the helper T cell by administering to the patient a nucleic acid molecule comprising a sequence encoding the immunogenic peptide.

The present invention is directed to methods of modulating the binding of peptide epitopes to HLA class II molecules. The invention includes a method of modifying binding of an original peptide epitope that bears a motif correlated with binding to an HLA molecule, said motif comprising at least one primary anchor position, said at least one primary anchor position having specified therefore primary anchor amino acid residues consisting essentially of two or more residues, said method comprising exchanging the primary anchor residue of the original peptide epitope for another primary anchor residue, with the proviso that the original primary anchor residue is not the same as the exchanged primary anchor residue. A preferred embodiment of the invention includes a method where the original primary anchor residue is a less preferred residue, and the exchanged residue is a more preferred residue.

One alternative embodiment of the invention includes a method of modifying binding of an original peptide epitope that bears a motif correlated with binding to an HLA molecule, said motif comprising at least one primary anchor position having specified therefore at least one primary anchor residue, and at least one secondary anchor position having specified therefore at least one secondary residue, said method comprising exchanging the secondary anchor residue of the original peptide epitope for another secondary anchor residue, with the proviso that the original secondary anchor residue is different than the exchanged amino acid residue. In some cases the original secondary residue is a deleterious residue and the exchanged residue is a residue other than a deleterious residue and/or the original secondary anchor residue is a less preferred residue and the exchanged residue is a more preferred residue.

As will be apparent from the discussion below, other methods and embodiments are also contemplated. Further, novel synthetic peptides produced by any of the methods described herein are also part of the invention.

Definitions

The following definitions are provided to enable one of ordinary skill in the art to understand some of the preferred embodiments of invention disclosed herein. It is understood, however, that these definitions are exemplary only and should not be used to limit the scope of the invention as set forth in the claims. Those of ordinary skill in the art will be able to construct slight modifications to the definitions below and utilize such modified definitions to understand and practice the invention disclosed herein. Such modifications, which would be obvious to one of ordinary skill in the art, as they may be applicable to the claims set forth below, are considered to be within the scope of the present invention. If a definition set forth in this section is contrary to or otherwise inconsistent with a definition set forth in patents, published patent applications and other publications and sequences from GenBank and other databases that are herein incorporated by reference, the definition set forth in this section prevails over the definition that is incorporated herein by reference.

An "HLA supertype or family", as used herein, describes sets of HLA molecules grouped on the basis of shared peptide-binding specificities, rather than serologic supertypes based on shared antigenic determinants. HLA class II molecules that share somewhat similar binding affinity for peptides bearing certain amino acid motifs are grouped into HLA supertypes. The terms "HLA superfamily," "HLA supertype family," "HLA family," and "HLA xx-like molecules" (where xx denotes a particular HLA type), are synonyms.

As used herein, the term "$IC_{50}$" refers to the concentration of peptide in a binding assay at which 50% inhibition of binding of a reference peptide is observed. Depending on the conditions in which the assays are run (i.e., limiting MHC proteins and labeled peptide concentrations), these values may approximate $K_D$ values. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand.

Alternatively, binding is expressed relative to a reference peptide. As a particular assay becomes more, or less, sensitive, the $IC_{50}$'s of the peptides tested may change somewhat. However, the binding relative to the reference peptide will not change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide.

As used herein, "high affinity" with respect to peptide binding to HLA class II molecules is defined as binding with an $K_D$ (or $IC_{50}$) of less than 50 nM. "Intermediate affinity" is binding with a $K_D$ (or $IC_{50}$) of between about 50 and about 500 nM. As used herein, "high affinity" with respect to binding to HLA class II molecules is defined as binding with an $K_D$ (or $IC_{50}$) of less than 100 nM. "Intermediate affinity" is binding with a $K_D$ (or $IC_{50}$) of between about 100 and about 1000 nM. Assays for determining binding are described in detail, e.g., in PCT publications WO 94/20127 and WO 94/03205.

Binding may also be determined using other assay systems including those using: live cells (e.g., Ceppellini et al., *Nature* 339:392 (1989); Christnick et al., *Nature* 352:67 (1991); Busch et al., *Int. Immunol.* 2:443 (1990); Hill et al., *J Immunol.* 147:189 (1991); del Guercio et al., *J Immunol.* 154:685 (1995)), cell free systems using detergent lysates (e.g., Cerundolo et al., *J Immunol.* 21:2069 (1991)), immobilized purified MHC (e.g., Hill et al., *J Immunol.* 152,2890 (1994); Marshall et al., *J Immunol.* 152:4946 (1994)), ELISA systems (e.g., Reay et al., *EMBO J* 11:2829 (1992)), surface plasmon resonance (e.g., Khilko et al., *J Biol. Chem.* 268:15425 (1993)); high flux soluble phase assays (Hammer et al., *J. Exp. Med.* 180:2353 (1994)).

The term "peptide" is used interchangeably with "oligopeptide" in the present specification to designate a series of residues, typically L-amino acids, connected one to the other typically by peptide bonds between the alpha-amino and carbonyl groups of adjacent amino acids. In certain embodiments, the oligopeptides of the invention are less than about 50 residues in length and usually consist of between about 6 and about 25 residues, preferably 14 or 15 residues. Further, an oligopeptide of the invention can be such that it does not comprise more than 50 contiguous amino acids of a native antigen. The preferred HTL-inducing peptides of the invention are 30 residues or less in length, sometimes 20 residues or less and usually consist of between about 6 and about 25 residues, preferably 14 or 15 residues.

"Synthetic peptide" refers to a peptide that is not naturally occurring, but is man-made using such methods as chemical synthesis or recombinant DNA technology.

The nomenclature used to describe peptide compounds follows the conventional practice wherein the amino group is presented to the left (the N-terminus) and the carboxyl group to the right (the C-terminus) of each amino acid residue. In the formulae representing selected specific embodiments of the present invention, the amino- and carboxyl-terminal groups, although not specifically shown, are in the form they would assume at physiologic pH values, unless otherwise specified. In the amino acid structure formula, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G. Symbols for each amino acids are shown below:

TABLE 1

Amino acids with their abbreviations

| Amino acid | Three letter code | Single letter code |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vivo or in vitro, an epitope is the collective features of a molecule, such as primary, secondary and tertiary peptide structure, and charge, that together form a site recognized by an immunoglobulin, T cell receptor or HLA molecule. Throughout this disclosure epitope and peptide are often used interchangeably.

It is to be appreciated that protein or peptide molecules that comprise an epitope of the invention as well as additional amino acid(s) are still within the bounds of the invention. In certain embodiments, there is a limitation on the length of a peptide of the invention. The embodiment that is length-limited occurs when the protein/peptide comprising an epitope of the invention comprises a region (i.e., a contiguous series of amino acids) having 100% identity with a native sequence. In order to avoid the definition of epitope from reading, e.g., on whole natural molecules, there is a limitation on the length of any region that has 100% identity with a native peptide sequence. Thus, for a peptide comprising an epitope of the invention and a region with 100% identity with a native peptide sequence, the region with 100% identity to a native sequence generally has a length of: less than or equal to 600 amino acids, often less than or equal to 500 amino acids, often less than or equal to 400 amino acids, often less than or equal to 250 amino acids, often less than or equal to 100 amino acids; often less than or equal to 85 amino acids, often less than or equal to 75 amino acids, often less than or equal to 65 amino acids, and often less than or equal to 50 amino acids. In certain embodiments, an "epitope" of the invention is comprised by a peptide having a region with less than 51 amino acids that has 100% identity to a native peptide sequence, in any increment down to 5 amino acids.

Accordingly, peptide or protein sequences longer than 600 amino acids are within the scope of the invention, so long as they do not comprise any contiguous sequence of more than 600 amino acids that have 100% identity with a native peptide sequence. For any peptide that has five contiguous residues or less that correspond to a native sequence, there is no limitation on the maximal length of that peptide in order to fall within the scope of the invention. It is presently preferred that a CTL epitope be less than 600 residues long in any increment down to eight amino acid residues.

A "dominant epitope" induces an immune response upon immunization with whole native antigens which comprise the epitope. (See, e.g., Sercarz, et al., *Annu. Rev. Immunol.* 11:729-766 (1993)). Such a response is cross-reactive in vitro with an isolated peptide epitope.

A "cryptic epitope" elicits a response by immunization with isolated peptide, but the response is not cross-reactive in vitro when intact whole protein which comprises the epitope is used as an antigen.

A "subdominant epitope" is an epitope which evokes little or no response upon immunization with whole antigens which comprise the epitope, but for which a response can be obtained by immunization in vivo or in vitro with an isolated epitope, and this response (unlike the case of cryptic epitopes) is detected when whole protein is used to recall the response in vitro.

A "pharmaceutical excipient" comprises a material such as an adjuvant, a carrier, pH-adjusting and buffering agents, tonicity adjusting agents, wetting agents, preservatives, and the like.

As used herein, the term "pharmaceutically acceptable" refers to a generally non-toxic, inert, and/or physiologically compatible composition.

As used herein, the term "protective immune response" or "therapeutic immune response" refers to a HTL and/or a CTL response to a tumor associated antigen, which in some way prevents or at least partially arrests disease symptoms, side effects or progression. The immune response may include an antibody response that has been facilitated by the stimulation of helper T cells.

In certain embodiments, an "immunogenic peptide" is a peptide which comprises an allele-specific motif such that the peptide will bind an MHC (HLA) molecule and induce a HTL response. Immunogenic peptides of the invention are capable of binding to an appropriate class II MHC molecule (e.g., HLA-DR) and inducing a helper T cell response against the antigen from which the immunogenic peptide is derived.

An "immunogenic response" includes one that stimulates a HTL and/or CTL response in vitro and/or in vivo as well as modulates an ongoing immune response through directed induction of cell death (or apoptosis) in specific T cell populations.

Immunogenic peptides of the invention are capable of binding to an appropriate HLA-DR molecule and inducing a helper T-cell response against the antigen from which the immunogenic peptide is derived. The immunogenic peptides of the invention are less than about 50 residues in length, often 30 residues or less in length, or 20 residues or less in length and usually consist of between about 6 and about 25 residues, preferably 14 or 15 residues.

The term "derived" when used to discuss an epitope is a synonym for "prepared." A derived epitope can be isolated from a natural source, or it can be synthesized in accordance with standard protocols in the art. Synthetic epitopes can comprise artificial amino acids "amino acid mimetics," such as D isomers of natural occurring L amino acids or non-natural amino acids such as cyclohexylalanine. A derived/prepared epitope can be an analog of a native epitope.

Immunogenic peptides are conveniently identified using the binding motif algorithms described for the specific HLA subtype (e.g., HLA-DR). The algorithms are mathematical procedures that produce a score which enables the selection of immunogenic peptides. Typically one uses the algorithmic score with a "binding threshold" to enable selection of peptides that have a high probability of binding at a certain affinity and will in turn be immunogenic. The algorithm is based upon either the effects on MHC binding of a particular amino acid at a particular position of a peptide or the effects on binding of a particular substitution in a motif containing peptide.

The term "residue" refers to an amino acid or amino acid mimetic incorporated into an oligopeptide by an amide bond or amide bond mimetic.

A "conserved residue" is an amino acid which occurs in a significantly higher frequency than would be expected by random distribution at a particular position in a peptide. Typically a conserved residue is one where the MHC structure may provide a contact point with the immunogenic peptide. At least one to three or more, preferably two, conserved residues within a peptide of defined length defines a motif for an immunogenic peptide. These residues are typically in close contact with the peptide binding groove, with their side chains buried in specific pockets of the groove itself. Typically, an immunogenic peptide will comprise up to three conserved residues, more usually two conserved residues.

The term "motif" refers to the pattern of residues in a peptide of defined length, usually about 6 to about 25 amino acids, which is recognized by a particular MHC allele (one or more HLA molecules). The peptide motifs are typically different for each human MHC allele and differ in the pattern of the highly conserved residues and negative residues. Peptide motifs are often unique for the protein encoded by each human HLA allele, differing in their pattern of the primary and secondary anchor residues. Typically as used herein, a "motif" refers to that pattern of residues which is recognized by an HLA molecule encoded by a particular allele. The binding motif for an allele can be defined with increasing degrees of precision.

The designation of a residue position in an epitope as the "carboxyl terminus" or the "carboxyl terminal position" refers to the residue position at the end of the epitope which is nearest to the carboxyl terminus of a peptide, which is designated using conventional nomenclature as defined below. The "carboxyl terminal position" of the epitope may or may not actually correspond to the end of the peptide or polypeptide.

The designation of a residue position in an epitope as "amino terminus" or "amino-terminal position" refers to the residue position at the end of the epitope which is nearest to the amino terminus of a peptide, which is designated using conventional nomenclature as defined below. The "amino terminal position" of the epitope may or may not actually correspond to the end of the peptide or polypeptide.

A "motif bearing peptide" or "peptide which comprises a motif" refers to a peptide that comprises primary anchors specified for a given motif or supermotif.

In certain embodiments, a "supermotif" is a peptide binding specificity shared by HLA molecules encoded by two or more HLA alleles. Preferably, a supermotif-bearing peptide is recognized with high or intermediate affinity (as defined herein) by two or more HLA molecules or antigens.

Alternatively, the term "supermotif" refers to motifs that, when present in an immunogenic peptide, allow the peptide to bind more than one HLA antigen. The supermotif preferably is recognized with high or intermediate affinity (as defined herein) by at least one HLA allele having a wide distribution in the human population, preferably recognized by at least two alleles, more preferably recognized by at least three alleles, and most preferably recognized by more than three alleles.

"Human Leukocyte Antigen" or "HLA" is a human class I or class II Major Histocompatibility Complex (MHC) protein (see, Stites, et al., IMMUNOLOGY, $8^{TH}$ ED., Lange Publishing, Los Altos, Calif. (1994).

"Major Histocompatibility Complex" or "MHC" is a cluster of genes which plays a role in control of the cellular interactions responsible for physiologic immune responses. In humans, the MHC complex is also known as the HLA complex. For a detailed description of the MHC and HLA complexes, see, Paul, FUNDAMENTAL IMMUNOLOGY, $3^{RD}$ ED., Raven Press, New York, 1993.

The phrases "isolated" or "biologically pure" refer to material which is substantially or essentially free from components which normally accompany it as found in its native state. Thus, the peptides of this invention do not contain materials normally associated with their in situ environment, e.g., MHC class II molecules on antigen presenting cells. Even where a protein has been isolated to a homogenous or dominant band, there are trace contaminants in the range of 5-10% of native protein which co-purify with the desired protein. Isolated peptides of this invention do not contain such endogenous co-purified protein.

"Peripheral blood mononuclear cells" (PBMCs) are cells found in from the peripheral blood of a patient. PBMCs comprise, e.g., CTLs and HTLs and antigen presenting cells.

These cells can contact an antigen in vivo, or be obtained from a mammalian source and contacted with an antigen in vitro.

"Cross-reactive binding" indicates that a peptide is bound by more than one HLA molecule; a synonym is degenerate binding.

"Promiscuous recognition" is where the same peptide bound by different HLA molecules is recognized by the same T cell clone. It may also refer to the ability of a peptide to be recognized by a single T cell receptor in the context of multiple HLA alleles.

"Link" or "join" refers to any method known in the art for functionally connecting peptides, including, without limitation, recombinant fusion, covalent bonding, disulfide bonding, ionic bonding, hydrogen bonding, and electrostatic bonding.

A "non-native" sequence or "construct" refers to a sequence that is not found in nature, i.e., is "non-naturally occurring". Such sequences include, e.g., peptides that are lipidated or otherwise modified, and polyepitopic compositions that contain epitopes that are not contiguous in a native protein sequence.

As used herein, a "vaccine" is a composition that contains one or more peptides of the invention, see, e.g., TABLE I. There are numerous embodiments of vaccines in accordance with the invention, such as by a cocktail of one or more peptides; one or more peptides of the invention comprised by a polyepitopic peptide; or nucleic acids that encode such peptides or polypeptides, e.g., a minigene that encodes a polyepitopic peptide. The "one or more peptides" can include any whole unit integer from 1-150, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class II-binding peptides of the invention can be linked to HLA class I-binding peptides, to facilitate activation of both cytotoxic T lymphocytes and helper T lymphocytes. Vaccines can comprise peptide pulsed antigen presenting cells, e.g., dendritic cells.

DETAILED DESCRIPTION OF THE INVENTION

Certain embodiments of the present invention relate in part to an epitope-based approach for vaccine design. Such an approach is based on the well-established finding that the mechanism for inducing HTL immune response comprises the step of presenting a HTL epitope as a peptide of about 6-25 amino acids bound to an HLA molecule displayed on an antigen-presenting cell.

Certain embodiments of the present invention relate to peptides comprising allele-specific peptide motifs and supermotifs which bind to HLA class II molecules.

As noted above, high HLA binding affinity is correlated with higher immunogenicity. Higher immunogenicity can be manifested in several different ways. For instance, a higher binding peptide will be immunogenic more often. Close to 90% of high binding peptides are immunogenic, as contrasted with about 50% of the peptides which bind with intermediate affinity. A higher binding peptide will also lead to a more vigorous response. As a result, less peptide is required to elicit a similar biological effect. Thus, in some embodiments of the invention high binding epitopes are particularly desired.

It has been noted that a significant number of epitopes derived from known non-viral tumor associated antigens (TAA) bind HLA Class II with intermediate affinity ($IC_{50}$ in the 50-500 mM range). It has been found that 8 of 15 known TAA peptides recognized by tumor infiltrating lymphocytes (TIL) or CTL bound in the 50-500 mM range. These data are in contrast with estimates that 90% of known viral antigens that were recognized as peptides bound HLA with $IC_{50}$ of 50 mM or less while only approximately 10% bound in the 50-500 mM range (Sette, et al., J. Immunol., 153:5586-5592 (1994)). This phenomenon is probably due in the cancer setting to elimination, or functional inhibition of the CTL recognizing several of the highest binding peptides, presumably because of T cell tolerization events.

Epitope-bearing peptides in accordance with the invention can be prepared synthetically, by recombinant DNA technology, or from natural sources such as whole viruses or tumors. Although the peptide will preferably be substantially free of other naturally occurring host cell proteins and fragments thereof, in some embodiments the peptides are synthetically conjugated to native molecules or particles; the peptides can also be conjugated to non-native molecules or particles.

The peptides in accordance with the invention can be a variety of lengths, and either in their neutral (uncharged) forms or in forms which are salts. The peptides in accordance with the invention are either free of modifications such as glycosylation, side chain oxidation, or phosphorylation; or they contain these modifications.

Desirably, the epitope-bearing peptide will be as small as possible while still maintaining relevant immunologic activity of the large peptide; of course it is particularly desirable with peptides from pathogenic organisms that the peptide be small in order to avoid pathogenic function. When possible, it may be desirable to optimize epitopes of the invention to a length of about 6 to about 25, preferably 14 to 15 amino acid residues for a class II molecule. Preferably, the peptides are commensurate in size with endogenously processed viral peptides or tumor cell peptides that are bound to HLA class I or class II molecules on the cell surface. Nevertheless, the identification and preparation of peptides of other lengths can be carried out using the techniques described here such as the disclosures of primary anchor positions. It is to be appreciated that peptide epitopes in accordance with the invention can be present in peptides or proteins that are longer than the epitope itself. Moreover, multiepitopic peptides can comprise at least one epitope of the invention along with other epitope(s).

In particular, the invention provides motifs that are common to peptides bound by more than one HLA allele. By a combination of motif identification and MHC-peptide interaction studies, peptides useful for peptide vaccines have been identified.

Peptides comprising the epitopes from these antigens are synthesized and then tested for their ability to bind to the appropriate MHC molecules in assays using, for example, immunofluorescent staining and flow microfluorometry, peptide-dependent class II assembly assays. Those peptides that bind to the class II molecule are further evaluated for their ability to serve as targets for HTLs derived from infected or immunized individuals, as well as for their capacity to induce primary in vitro or in vivo HTL responses that can give rise to HTL populations capable of reacting with tumor cells as potential therapeutic agents.

The starting point, therefore, for the design of effective vaccines is to ensure that the vaccine will generate a large number of epitopes that can successfully be presented. It may be possible to administer the peptides representing the epitopes per se. Such administration is dependent on the presentation of "empty" HLA molecules displayed on the cells of the subject. In one approach to use of the immunogenic peptides per se, these peptides may be incubated with antigen-presenting cells from the subject to be treated ex vivo and the cells then returned to the subject.

Alternatively, the peptides can be generated in situ by administering a nucleic acid containing a nucleotide sequence encoding it. Means for providing such nucleic acid molecules are described in WO99/58658, the disclosure of which is incorporated herein by reference. Further, the immunogenic peptides can be administered as portions of a larger peptide molecule and cleaved to release the desired peptide. The larger peptide may contain extraneous amino acids, in general the fewer the better. Thus, peptides which contain such amino acids are typically 50 amino acids or less, more typically 30 amino acids or less, and more typically 20 amino acids or less. The precursor may also be a heteropolymer or homopolymer containing a multiplicity of different or same HTL epitopes. Of course, mixtures of peptides and nucleic acids which generate a variety of immunogenic peptides can also be employed. The design of the peptide vaccines, the nucleic acid molecules, or the hetero- or homo-polymers is dependent on the inclusion of the desired epitope.

In certain embodiments, it is preferred that peptides include an epitope that binds to an HLA-DR supertype allele. These motifs may be used to define T-cell epitopes from any desired antigen, particularly those associated with human cancers for which the amino acid sequence of the potential antigen targets is known.

The peptides are thus useful in pharmaceutical compositions for both in vivo and ex vivo therapeutic and diagnostic applications.

Peptides comprising the supermotif sequences can be identified, as noted above, by screening potential antigenic sources. Useful peptides can also be identified by synthesizing peptides with systematic or random substitution of the variable residues in the supermotif, and testing them according to the assays provided. As demonstrated below, it is useful to refer to the sequences of the target HLA molecule, as well.

For epitope-based vaccines, the peptides of the present invention preferably comprise a supermotif and/or motif recognized by an HLA class II molecule having a wide distribution in the human population. The large degree of HLA polymorphism is an important factor to be taken into account with the epitope-based approach to vaccine development. To address this factor, epitope selection encompassing identification of peptides capable of binding at high or intermediate affinity to multiple HLA molecules is preferably utilized, most preferably these epitopes bind at high or intermediate affinity to two or more allele-specific HLA molecules.

HTL-inducing peptides of interest for vaccine compositions preferably include those that have an $IC_{50}$ or binding affinity value for class II HLA molecules, 1000 nM or better (i.e., the value is greater than or equal to 1000 nM). For example, peptide binding is assessed by testing the capacity of a candidate peptide to bind to a purified HLA molecule in vitro. Peptides exhibiting high or intermediate affinity are then considered for further analysis. Selected peptides are generally tested on other members of the supertype family. In preferred embodiments, peptides that exhibit cross-reactive binding are then used in cellular screening analyses or vaccines.

Definition of motifs that are predictive of binding to specific class II alleles allows the identification of potential peptide epitopes from an antigenic protein whose amino acid sequence is known. Typically, identification of potential peptide epitopes is initially carried out using a computer to scan the amino acid sequence of a desired antigen for the presence of motifs and/or supermotifs.

The previous definition of motifs specific for different class II alleles allows the identification of potential peptide epitopes from an antigenic protein whose amino acid sequence is known. Typically, identification of potential peptide epitopes is initially carried out using a computer to scan the amino acid sequence of a desired antigen for the presence of motifs. The epitopic sequences are then synthesized. The capacity to bind MHC Class II molecules is measured in a variety of different ways.

The procedures used to identify peptides of the present invention generally follow the methods disclosed in Falk et al., Nature 351:290 (1991), which is incorporated herein by reference. Briefly, the methods involve large-scale isolation of MHC class II molecules, typically by immunoprecipitation or affinity chromatography, from the appropriate cell or cell line. Examples of other methods for isolation of the desired MHC molecule equally well known to the artisan include ion exchange chromatography, lectin chromatography, size exclusion, high performance ligand chromatography, and a combination of all of the above techniques.

The peptides bound to the peptide binding groove of the isolated MHC molecules are eluted typically using acid treatment. Peptides can also be dissociated from class II molecules by a variety of standard denaturing means, such as heat, pH, detergents, salts, chaotropic agents, or a combination thereof.

Peptide fractions are further separated from the MHC molecules by reversed-phase high performance liquid chromatography (HPLC) and sequenced. Peptides can be separated by a variety of other standard means well known to the artisan, including filtration, ultrafiltration, electrophoresis, size chromatography, precipitation with specific antibodies, ion exchange chromatography, isoelectrofocusing, and the like.

Sequencing of the isolated peptides can be performed according to standard techniques such as Edman degradation (Hunkapiller, M. W., et al., Methods Enzymol. 91, 399 [1983]). Other methods suitable for sequencing include mass spectrometry sequencing of individual peptides as previously described (Hunt, et al., Science 225:1261 (1992), which is incorporated herein by reference). Amino acid sequencing of bulk heterogenous peptides (e.g., pooled HPLC fractions) from different class I molecules typically reveals a characteristic sequence motif for each class I allele.

Next, peptides that test positive in the MHC class II binding assay are assayed for the ability of the peptides to induce specific HTL responses in vitro. For instance, antigen-presenting cells that have been incubated with a peptide can be assayed for the ability to induce HTL responses in responder cell populations. Antigen-presenting cells can be normal cells such as peripheral blood mononuclear cells or dendritic cells (Inaba, et al., J. Exp. Med. 166:182 (1987); Boog, Eur. J. Immunol, 18:219 (1988)).

As disclosed herein, higher HLA binding affinity is correlated with greater immunogenicity. Greater immunogenicity can be manifested in several different ways. Immunogenicity can correspond to whether an immune response is elicited at all, and to the vigor of any particular response, as well as to the extent of a diverse population in which a response is elicited. For example, a peptide might elicit an immune response in a diverse array of the population, yet in no instance produce a vigorous response. In accordance with the principles disclosed herein, close to 90% of high binding peptides have been found to be immunogenic, as contrasted with about 50% of the peptides which bind with intermediate affinity. Moreover, higher binding affinity peptides lead to more vigorous immunogenic responses. As a result, less peptide is required to elicit a similar biological effect if a high affinity binding peptide is used. Thus, in preferred embodiments of the invention, high affinity binding epitopes are particularly useful. Nevertheless, improvements over the prior art are achieved with intermediate or high binding peptides.

After determining their binding affinity, additional confirmatory work can be performed to select, amongst these vaccine candidates, epitopes with preferred characteristics in terms of population coverage, antigenicity, and immunogenicity.

Thus, various strategies can be utilized to evaluate immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998); This procedure involves the stimulation of peripheral blood lymphocytes (PBL) from normal subjects with a test peptide in the presence of antigen presenting cells in vitro over a period of several weeks. T cells specific for the peptide become activated during this time and are detected.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997); In this method, peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected.

3) Demonstration of recall T cell responses from patients who have been effectively vaccinated or who have a tumor; (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997; Tsang et al., *J. Natl. Cancer Inst.* 87:982-990, 1995; Disis et al., *J. Immunol.* 156:3151-3158, 1996). In applying this strategy, recall responses are detected by culturing PBL from patients with cancer who have generated an immune response "naturally", or from patients who were vaccinated with tumor antigen vaccines. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected.

An immunogenic peptide epitope of the invention may be included in a polyepitopic vaccine composition comprising additional peptide epitopes of the same antigen, antigens from the same source, and/or antigens from a different source. Moreover, class II epitopes can be included along with class I epitopes. Peptide epitopes from the same antigen may be adjacent epitopes that are contiguous in sequence or may be obtained from different regions of the protein.

An epitope present in the peptides of the invention can be cross-reactive or non-cross-reactive in its interactions with MHC alleles and allele subtypes. Cross-reactive binding of an epitope (or peptide) permits an epitope to be bound by more than one HLA molecule. Such cross-reactivity is also known as degenerate binding. A non-cross-reactive epitope would be restricted to binding a particular MHC allele or allele subtype.

Motifs Indicative of Class II HTL Inducing Peptide Epitope

The primary anchor residues of the HLA class II supermotifs and motifs are delineated below.

HLA DR-1-4-7 Supermotif

Motifs have also been identified for peptides that bind to three common HLA class II allele-specific HLA molecules: HLA DRB1*0401, DRB1*0101, and DRB1*0701 (see, e.g., the review by Southwood et al. *J. Immunology* 160:3363-3373, 1998). Collectively, the common residues from these motifs delineate the HLA DR-1-4-7 supermotif Peptides that bind to these DR molecules carry a supermotif characterized by a large aromatic or hydrophobic residue (Y, F, W, L, I, V, or M) as a primary anchor residue in position 1, and a small, non-charged residue (S, T, C, A, P, V, I, L, or M) as a primary anchor residue in position 6 of a 9-mer core region. Allele-specific secondary effects and secondary anchors for each of these HLA types have also been identified (Southwood et al., supra). Peptide binding to HLA-DRB1*0401, DRB1*0101, and/or DRB1*0701 can be modulated by substitutions at primary and/or secondary anchor positions, preferably choosing respective residues specified for the supermotif.

Two alternative motifs (i.e., submotifs) characterize peptide epitopes that bind to HLA-DR3 molecules (see, e.g., Geluk et al., *J. Immunol.* 152:5742, 1994). In the first motif (submotif DR3A) a large, hydrophobic residue (L, I, V, M, F, or Y) is present in anchor position 1 of a 9-mer core, and D is present as an anchor at position 4, towards the carboxyl terminus of the epitope. As in other class II motifs, core position 1 may or may not occupy the peptide N-terminal position.

The alternative DR3 submotif provides for lack of the large, hydrophobic residue at anchor position 1, and/or lack of the negatively charged or amide-like anchor residue at position 4, by the presence of a positive charge at position 6 towards the carboxyl terminus of the epitope. Thus, for the alternative allele-specific DR3 motif (submotif DR3B): L, I, V, M, F, Y, A, or Y is present at anchor position 1; D, N, Q, E, S, or T is present at anchor position 4; and K, R, or H is present at anchor position 6. Peptide binding to HLA-DR3 can be modulated by substitutions at primary and/or secondary anchor positions, preferably choosing respective residues specified for the motif.

As with HLA class I binding peptides, motifs have also been defined for HLA class II-binding peptides. Several studies have identified an important role for an aromatic or hydrophobic residue (I, L, M, V, F, W, or Y) at position 1 of a 9-mer core region, typically nested within a longer peptide sequence, in the binding of peptide ligands to several HLA-class II alleles (Hammer et al. *Cell* 74:197, (1993); Sette et al. *J. Immunol.* 151:3163-70 (1993); O'Sullivan et al. *J. Immunol.* 147:2663 (1991); and Southwood et al. *J. Immunol.* 160:3363-73 (1998)). A strong role has also been demonstrated for the residue in position 6 of the 9-mer core, where short and/or hydrophobic residues (S, T, C, A, P, V, I, L, or M) are preferred. This position 1-position 6 motif has been described as a DR-supermotif (Southwood et al. *J. Immunol.* 160:3363-3373 (1998)) and has been shown to efficiently identify peptides capable of binding a large set of common HLA-class II alleles.

Peptides binding to class II molecules may also be analyzed with respect to the identification of secondary preferred or deleterious residues. For example, to derive a more detailed DRB1*0401 motif to define secondary residues influencing peptide binding, we employed a strategy similar to that performed with class I peptides. For each peptide analyzed, nine-residue-long core regions were aligned on the basis of the primary class II positions P1 and P6 anchors. Then, the average binding affinity of a peptide carrying a particular residue was calculated for each position, relative to the remainder of the group. Following this method, values showing average relative binding were compiled. These values also present a map of the positive or negative effect of each of the 20 naturally occurring amino acids in DRB1*0401 binding capacity when occupying a particular position relative to the P1-P6 class II motif positions.

Variations in average relative binding of greater than or equal to fourfold or less than or equal to 0.25 were arbitrarily considered significant and indicative of secondary effects of a given residue on HLA-peptide interactions. Most secondary effects were associated with P4, P7, and P9. These positions correspond to secondary anchors engaging shallow pockets on the DR molecule. Similar studies defining secondary residues were also performed for DRB1*0101 and DRB1*0701. The definitions of secondary residues of motifs for DR1, DR4, and DR7 are shown in TABLE 139.

Upon definition of allele-specific secondary effects and secondary anchors, allele-specific algorithms were derived and utilized to identify peptides binding DRB1*0101, DRB1*0401, and DRB*0701. Further experiments, identified a large set of HLA class II molecules, which includes at least the DRB1*0101, DRB1*0401, and DRB*0701, DRB1*1501, DRB1*0901 and DRB1*1302 allelic products recognizing the DR supermotif, and is characterized by largely overlapping peptide binding repertoires.

The data presented above confirm that several common HLA class II types are characterized by largely overlapping peptide binding repertoires. On this basis, in analogy to the case of HLA class I molecules, HLA class II molecules can be grouped in a HLA class II supertype, defined and characterized by similar, or largely overlapping (albeit not identical) peptide binding specificities.

The peptides present in the invention can be identified by any suitable method. For example, peptides are conveniently identified using the algorithms of the invention described in the co-pending U.S. patent application Ser. No. 09/894,018. These algorithms are mathematical procedures that produce a score which enables the selection of immunogenic peptides. Typically one uses the algorithmic score with a binding threshold to enable selection of peptides that have a high probability of binding at a certain affinity and will in turn be immunogenic. The algorithm are based upon either the effects on MHC binding of a particular amino acid at a particular position of a peptide or the effects on binding MHC of a particular substitution in a motif containing peptide.

Peptide sequences characterized in molecular binding assays and capture assays have been and can be identified utilizing various technologies. Motif-positive sequences are identified using a customized application created at Epimmune. Sequences are also identified utilizing matrix-based algorithms, and have been used in conjunction with a "power" module that generates a predicted 50% inhibitory concentration (PIC) value. These latter methods are operational on Epimmune's HTML-based Epitope Information System (EIS) database. All of the described methods are viable options in peptide sequence selection for $IC_{50}$ determination using binding assays.

The capacity to bind MHC molecules is measured in a variety of different ways. One means is a MHC binding assay as described in the related applications, noted above. Other alternatives described in the literature include inhibition of antigen presentation (Sette, et al., *J. Immunol.* 141:3893 (1991), in vitro assembly assays (Townsend, et al., *Cell* 62:285 (1990), and FACS based assays using mutated cells, such as RMA.S (Melief, et al., *Eur. J. Immunol.* 21:2963 (1991)).

Capture Assay: Unlike the HPLC-based molecular binding assay, noted above, the high throughput screening ("HTS") Capture assay does not utilize a size-exclusion silica column for separation of bound from unbound radioactive marker. Instead, wells of an opaque white 96-well Optiplate (Packard) are coated with 3 μg (100 μl @ 30 μg/ml) of HLA-specific antibody (Ab) that "capture" complexes of radiolabeled MHC and unlabeled peptide transferred from the molecular binding assay plate in 100 μl of 0.05% NP40/PBS. After a 3-hour incubation period, the supernatant is decanted and scintillation fluid (Microscint 20) added. Captured complexes are then measured on a microplate scintillation and luminescence counter (TopCount NXT™; Packard).

Additional assays for determining binding are described in detail, i.e., in PCT publications WO 94/20127 and WO 94/03205. Binding data results are often expressed in terms of $IC_{50}$ value. $IC_{50}$ is the concentration of peptide in a binding assay at which 50% inhibition of binding of a reference peptide occurs. Given the conditions in which the assays are preformed (i.e., limiting MHC proteins and labeled peptide concentrations), these values approximate $K_D$ values. It should be noted that $IC_{50}$ values can change, often dramatically, if the assay conditions are varied, and depending on the particular reagents used (i.e., MHC preparation, etc.). For example, excessive concentrations of MHC molecules will increase the apparent measured $IC_{50}$ of a given ligand. Alternatively, binding is expressed relative to a reference peptide. Although as a particular assay becomes more, or less, sensitive, the $IC_{50}$'s of the peptides tested may change somewhat, the binding relative to the reference peptide will not significantly change. For example, in an assay preformed under conditions such that the $IC_{50}$ of the reference peptide increases 10-fold, the $IC_{50}$ values of the test peptides will also increase approximately 10-fold. Therefore, to avoid ambiguities, the assessment of whether a peptide is a good, intermediate, weak, or negative binder is generally based on its $IC_{50}$, relative to the $IC_{50}$ of a standard peptide.

The peptides of the invention may also comprise isosteres of two or more residues in the MHC-binding peptide. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, Peptides and Proteins*, Vol. VII (Weinstein ed., 1983).

Modifications of peptides with various amino acid mimetics or unnatural amino acids are particularly useful in increasing the stability of the peptide in vivo. Stability can be assayed in a number of ways. For instance, peptidases and various biological media, such as human plasma and serum, have been used to test stability. See, e.g., Verhoef et al., *Eur. J. Drug Metab. Pharmacokin.* 11:291-302 (1986). Half life of the peptides of the present invention is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

Such analogs may also possess improved shelf-life or manufacturing properties. More specifically, non-critical amino acids need not be limited to those naturally occurring in proteins, such as L-α-amino acids, or their D-isomers, but may include non-natural amino acids as well, such as amino acids mimetics, e.g. D- or L-naphylalanine; D- or L-phenylglycine; D- or L-2-thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-ρ-fluorophenylalanine; D- or L-ρ-biphenylphenylalanine; D- or L-ρ-methoxybiphenylphenylalanine; D- or L-2-indole(alkyl)alanines; and, D- or L-alkylalanines, where the alkyl group can be a substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Another embodiment for generating effective peptide analogs involves the substitution of residues that have an adverse impact on peptide stability or solubility in, e.g., a liquid environment. This substitution may occur at any position of the peptide epitope. Analogs of the present invention may include peptides containing substitutions to modify the physical property (e.g., stability or solubility) of the resulting peptide. For example, a cysteine (C) can be substituted out in favor of α-amino butyric acid. Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances (see, e.g., the review by Sette et al., In: Persistent Viral Infections, Eds. R. Ahmed and I. Chen, John Wiley & Sons, England, 1999). Substitution of cysteine with α-amino butyric acid may occur at any residue of a peptide epitope, i.e. at either anchor or non-anchor positions.

The binding activity, particularly modification of binding affinity or cross-reactivity among HLA supertype family members, of peptides of the invention can also be altered using analoging, which is described in co-pending U.S. application Ser. No. 09/226,775 filed Jan. 6, 1999. In brief, the analoging strategy utilizes the motifs or supermotifs that correlate with binding to certain HLA molecules. Analog peptides can be created by substituting amino acid residues at primary anchor, secondary anchor, or at primary and secondary anchor positions. Generally, analogs are made for peptides that already bear a motif or supermotif. For a number of the motifs or supermotifs in accordance with the invention, residues are defined which are deleterious to binding to allele-specific HLA molecules or members of HLA supertypes that bind the respective motif or supermotif (see, e.g., Rupert et al. Cell 74:929, 1993; Sidney, J. et al., Hu. Immunol. 45:79, 1996; and Sidney et al.; Sidney, et al., J. Immunol. 154:247, 1995). Accordingly, removal of such residues that are detrimental to binding can be performed in accordance with the present invention. For example, in the case of the A3 supertype, when all peptides that have such deleterious residues are removed from the population of peptides used in the analysis, the incidence of cross-reactivity increased from 22% to 37% (see, e.g., Sidney, J. et al., Hu. Immunol. 45:79, 1996).

Thus, one strategy to improve the cross-reactivity of peptides within a given supermotif is simply to delete one or more of the deleterious residues present within a peptide and substitute a small "neutral" residue such as Ala (that may not influence T cell recognition of the peptide). An enhanced likelihood of cross-reactivity is expected if, together with elimination of detrimental residues within a peptide, "preferred" residues associated with high affinity binding to an allele-specific HLA molecule or to multiple HLA molecules within a superfamily are inserted.

In some embodiments, a T helper peptide can used in addition to one of the peptides of the invention. One type of T helper peptide is one that is recognized by T helper cells in the majority of the population. This can be accomplished by selecting amino acid sequences that bind to many, most, or all of the MHC class II molecules. These are known as "loosely MHC-restricted" T helper sequences. Examples of amino acid sequences that are loosely MHC-restricted include sequences from antigens such as Tetanus toxin at positions 830-843 (QYIKANSKFIGITE (SEQ ID NO: 1)), *Plasmodium falciparum* circumsporozoite (CS) protein at positions 378-398 (DIEKKIAKMEKASSVFNVVNS (SEQ ID NO: 2)), and *Streptococcus* 18 kD protein at positions 1-16 (YGAVDSILGGVATYGAA (SEQ ID NO: 3)).

Alternatively, it is possible to prepare synthetic peptides capable of stimulating T helper lymphocytes, in a loosely MHC-restricted fashion, using amino acid sequences not found in nature (see, e.g., PCT publication WO 95/07707). These synthetic compounds, called Pan-DR-binding epitopes or PADRE® molecules (Epimmune, San Diego, Calif.), are designed on the basis of their binding activity to most HLA-DR (human MHC class II) molecules (see, e.g., U.S. Ser. No. 08/121,101 (now abandoned) and related U.S. Ser. No. 08/305,871 (now U.S. Pat. No. 5,736,142)). For instance, a pan-DR-binding epitope peptide having the formula: aKXVWANTLKAAa (SEQ ID NO: 4), where X is either cyclohexylalanine, phenylalanine, or tyrosine, and "a" is either D-alanine or L-alanine, has been found to bind to most HLA-DR alleles, and to stimulate the response of T helper lymphocytes from most individuals, regardless of their HLA type.

Particularly preferred immunogenic peptides and/or T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the HTL peptide may be linked to the T helper peptide without a spacer.

The immunogenic peptide may be linked to the T helper peptide either directly or via a spacer either at the amino or carboxy terminus of the HTL peptide. The amino terminus of either the immunogenic peptide or the T helper peptide may be acylated. The T helper peptides used in the invention can be modified in the same manner as HTL peptides. For instance, they may be modified to include D-amino acids or be conjugated to other molecules such as lipids, proteins, sugars and the like. Exemplary T helper peptides include tetanus toxoid 830-843, influenza 307-319, malaria circumsporozoite 382-398 and 378-389.

In some embodiments it may be desirable to include in the pharmaceutical compositions of the invention at least one component which primes HTL and CTL. Lipids have been identified as agents capable of priming HTL and CTL in vivo against viral antigens. For example, palmitic acid residues can be attached to the alpha and epsilon amino groups of a Lys residue and then linked, e.g., via one or more linking residues such as Gly, Gly-Gly-, Ser, Ser-Ser, or the like, to an immunogenic peptide. The lipidated peptide can then be injected directly in a micellar form, incorporated into a liposome or emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of the immunogenic peptide. Also in a preferred embodiment a particularly effective immunogen comprises palmitic acid attached to alpha and epsilon amino groups of Lys, which is attached via linkage, e.g., Ser-Ser, to the amino terminus of a class I restricted peptide having T cell determinants, such as those peptides described herein as well as other peptides which have been identified as having such determinants.

As another example of lipid priming of HTL and CTL responses, E. coli lipoproteins, such as tripalmitoyl-S-glycerylcysteinlyseryl-serine ($P_3CSS$) can be used to prime virus specific HTL CTL when covalently attached to an appropriate peptide. See, Deres et al., Nature 342:561-564 (1989), incorporated herein by reference. Peptides of the invention can be coupled to P3CSS, for example, and the lipopeptide administered to an individual to specifically prime a HTL response to the target antigen. Further, as the induction of neutralizing antibodies can also be primed with P3CSS conjugated to a peptide which displays an appropriate epitope, the two compositions can be combined to more effectively elicit both humoral and cell-mediated responses to infection.

In addition, additional amino acids can be added to the termini of a peptide to provide for ease of linking peptides one to another, for coupling to a carrier support, or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide. Modification at the C terminus in some cases may alter binding characteristics of the peptide. In addition, the peptide or oligopeptide sequences can differ from the natural sequence by being modified by terminal-$NH_2$ acylation, e.g., by alkanoyl ($C_1$-$C_{20}$) or thioglycolyl acetylation, terminal-carboxyl amidation, e.g., ammonia, methylamine, etc. In some instances these modifications may provide sites for linking to a support or other molecule.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co. (1984), supra.

Another aspect of the present invention is directed to vaccines which comprise an immunogenically effective amount of one or more peptides as described herein. Peptides may be introduced into a host using a variety of delivery vehicles known to those of skill in the art including PLG microspheres with entrapped peptides and virus-like particles. Furthermore, epitopes may be introduced as multiple antigen peptides (MAPs) (see e.g., Mora and Tam, J. Immunol. 161:3616-23 (1998)), or as immunostimulating complexes (ISCOMS) (see e.g., Hu et al. Clin. Exp. Immunol. 113:235-43 (1998)) as known in the art.

Vaccines that contain an immunogenically effective amount of one or more peptides as described herein are a further embodiment of the invention. The vaccines of the invention can be used both as a preventative or therapeutic. Once appropriately immunogenic epitopes have been defined, they can be delivered by various means, herein referred to as "vaccine" compositions. Such vaccine compositions can include, for example, lipopeptides (e.g., Vitiello, A. et al., J: Clin. Invest. 95:341, 1995), peptide compositions encapsulated in poly(DL-lactide-co-glycolide) ("PLG") microspheres (see, e.g., Eldridge, et al., Molec. Immunol. 28:287-294, 1991: Alonso et al., Vaccine 12:299-306, 1994; Jones et al., Vaccine 13:675-681, 1995), peptide compositions contained in immune stimulating complexes (ISCOMS) (see, e.g., Takahashi et al., Nature 344:873-875, 1990; Hu et al., Clin Exp Immunol. 113:235-24: 1998), multiple antigen peptide systems (MAPs) (see e.g., Tam, J. P., Proc. Natl. Acad Sci. U.S.A. 85:5409-5413, 1988; Tam, J. P., J Immunol. Methods 196:17-32, 1996), vir delivery vectors (Perkus, M. E. et al., In: Concepts in vaccine development, Kaufmann H. E., ed., p. 379, 1996; Chakrabarti, S. et al., Nature 320:535, 1986; Hu, S. L. et al., Nature 320:537, 1986; Kieny, M.-P. et al., AIDS Bio/Technology 4:790, 1986; Top, F. et al., J Infect. Dis. 124:148, 1971; Chanda, P. K. et al., Virology 175:535, 1990), particles of viral or synthetic origin (e.g., Kofler, N. et al., J Immunol. Methods. 192:2-1996; Eldridge, J. H. et al., Sem. Bematol. 30:16, 1993; Fa10, L. D., Jr. et al., Nature Med. 7:649, 1995), adjuvants (Warren, H. S., Vogel, F. R., and Chedid, L. A. Annu. Re Immunol. 4:369, 1986; Gupta, R. K. et al., Vaccine 11:293, 1993), liposomes (Reddy, R et al., J Immunol. 148:1585, 1992; Rock, K. L., Immunol. Today 17:131, 1996), or, naked or particle absorbed cDNA (Ulmer, J. B. et al., Science 259:1745, 1993; Robinsol H. L., Hunt, L. A., and Webster, R. G., Vaccine 11:957, 1993; Shiver, J. W. et al., In: Concepts in vaccine development, Kaufmann, S. H. E., ed., p. 423, 1996; Cease, K. B., and Berzofsky, J. A., Annu. Rev. Immunol. 12:923, 1994 and Eldridge, J. H. et al., Sem. Hematol. 30:16, 1993). Toxin-targeted delivery technologies, also known as receptor mediated targeting, such as those of Avant Immunotherapeutics, Inc. (Needham, Mass.) may also be used.

Vaccine compositions of the invention include nucleic acid-mediated modalities. DNA or RNA encoding one or more of the peptides of the invention can also be administered to a patient. This approach is described, for instance, in Wolff et. al., Science 247: 1465 (1990) as well as U.S. Pat. Nos. 5,580,859; 5,589,466; 5,804,566; 5,739,118; 5,736, 524; 5,679,647; WO 98/04720; and in more detail below. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, the peptides of the invention can be expression vectors include attenuated viral hosts, such as vaccinia or fowlpox. This approach involves the use of vaccinia virus, for example, as a vector to express nucleotide sequences that encode the pep tides of the invention. Upon introduction into an acutely or chronically infected host or into a non-infected host, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Furthermore, vaccines in accordance with the invention can encompass one or more of the peptides of the invention. Accordingly, a peptide can be present in a vaccine individually. Alternatively, the peptide can be individually linked to its own carrier; alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition may be a naturally occurring region of an antigen or may be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, CTL responses can be primed by conjugating peptides of the invention to lipids, such as tripalmitoyl-S-glycerylcysteinlyseryl-serine (P3CSS).

Upon immunization with a peptide composition in accordance with the invention, via injection, aerosol, oral, transdermal, transmucosal, intrapleural, intrathecal, or other suitable routes, the immune system of the host responds to the vaccine by producing large amounts of HTLs and/or CTLs specific for the desired antigen. Consequently, the host becomes at least partially immune to later infection, or at least partially resistant to developing an ongoing chronic infection, or derives at least some therapeutic benefit when the antigen was tumor-associated.

For therapeutic or immunization purposes, the peptides of the invention can also be expressed by vectors. Examples of expression vectors include attenuated viral hosts, such as vaccinia or fowlpox. This approach involves the use of vaccinia virus as a vector to express nucleotide sequences that encode the peptides of the invention. Vaccinia vectors and methods useful in immunization protocols are described in, e.g., U.S. Pat. No. 4,722,848. Another vector is BCG (Bacille Calmette Guerin). BCG vectors are described in Stover, et al. *Nature* 351:456-60 (1991). A wide variety of other vectors useful for therapeutic administration or immunization of the peptides of the invention, e.g., *Salmonella typhi* vectors, retroviral vectors, adenoviral or adeno-associated viral vectors, and the like will be apparent to those skilled in the art from the description herein.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1982) (also 1989), which is incorporated herein by reference. Thus, fusion proteins which comprise one or more peptide sequences of the invention can be used to present the appropriate T cell epitope. For example, a coding sequence encoding a peptide of the invention can be provided with appropriate linkers and ligated into expression vectors commonly available in the art, and the vectors used to transform suitable hosts to produce the desired fusion protein. A number of such vectors and suitable host systems are now available. Expression constructs, i.e., minigenes are described in greater detail in the sections below. Such methodologies are also used to present at least one peptide of the invention along with a substance which is not a peptide of the invention.

As the coding sequence for peptides of the length contemplated herein can be synthesized by chemical techniques, for example, using the phosphotriester method of Matteucci et al., *J. Am. Chem. Soc.* 103:3185 (1981), with modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

The peptides of the present invention and pharmaceutical and vaccine compositions thereof are useful for administration to mammals, particularly humans, to treat and/or prevent cancer.

In therapeutic applications, compositions are administered to a patient in an amount sufficient to elicit an effective HTL response to the tumor antigen and to cure or at least partially arrest symptoms and/or complications. An amount adequate to accomplish this is defined as "therapeutically effective dose" or "unit dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 5000 µg of peptide for a 70 kg patient, followed by boosting dosages of from about 1.0 µg to about 1000 µg of peptide pursuant to a boosting regimen over weeks to months depending upon the patient's response and condition by measuring specific CTL activity in the patient's blood. In alternative embodiments, generally for humans the dose range for the initial immunization (that is for therapeutic or prophylactic administration) is from about 1.0 µg to about 20,000 µg of peptide for a 70 kg patient, preferably, 100 µg-, 150 µg-, 200 µg-, 250 µg-, 300 µg-, 400 µg-, or 500 µg-20,000 µg, followed by boosting dosages in the same dose range pursuant to a boosting regimen over weeks to months depending upon the patient's response and condition by measuring specific HTL activity in the patient's blood. In embodiments where recombinant nucleic acid administration is used, the administered material is titrated to achieve the appropriate therapeutic response.

It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

For therapeutic use, administration should begin at the first sign of tumors or shortly after diagnosis. This is followed by boosting doses until at least symptoms are substantially abated and for a period thereafter.

Treatment of an affected individual with the compositions of the invention may hasten resolution of the infection in acutely infected individuals. For those individuals susceptible (or predisposed) to developing cancer the compositions are particularly useful in methods for preventing the evolution of cancer.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

A pharmaceutical composition of the invention may comprise one or more T cell stimulatory peptides of the invention. For example, a pharmaceutical composition may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more T cell stimulatory peptides of the invention. Moreover, a pharmaceutical composition of the invention may comprise one or more T cell stimulatory peptides of the invention in combination with one or more other T cell stimulatory peptides. The concentration of each unique T cell stimulatory peptide of the invention in the pharmaceutical formulations can vary widely, e.g., from less than about 0.001%, about 0.002%, about 0.003%, about 0.004%, about 0.005%, about 0.006%, 0.007%, 0.008%, 0.009%, about 0.01%, about 0.02%, about 0.025%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 3%, about 4%, about 5%, about 6%, about 7%, about 8%, about 9%, about 10%, about 20%, to about 50% or more by weight, and will be selected primarily by fluid volumes, viscosities, etc., in accordance with the particular mode of administration selected. In a preferred embodiment, the concentration of each unique T cell stimulatory peptide of the invention in the pharmaceutical formulations is about 0.001%, about 0.002%, about 0.003%, about 0.004%, about 0.005%, about 0.006%, 0.007%, 0.008%, 0.009%, about 0.01%, about 0.02%, about 0.025%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1% by weight. In a more preferred embodiment, the concentration of each unique T cell stimulatory peptide of the invention in the pharmaceutical formulations is about 0.01%, about 0.02%, about 0.025%, about 0.03%, about 0.04%, about 0.05%, about 0.06%, about 0.07%, about 0.08%, about 0.09%, about 0.1% by weight.

The concentration of HTL stimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected. A human unit dose form of the peptide composition is typically included in a pharmaceutical composition that comprises a human unit dose of an acceptable carrier, preferably an aqueous carrier, and is administered in a volume of fluid that is known by those of skill in the art to be used for administration of such compositions to humans.

The peptides of the invention may also be administered via liposomes, which serve to target the peptides to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

In another aspect the present invention is directed to vaccines which contain as an active ingredient an immunogenically effective amount of an immunogenic peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of tumor cells. Useful carriers are well known in the art, and include, e.g., thyroglobulin, albumins such as human serum albumin, tetanus toxoid, polyamino acids such as poly(lysine:glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. Upon immunization with a peptide composition as described herein, via injection, aerosol, oral, transdermal or other route, the immune system of the host responds to the vaccine by producing large amounts of HTLs specific for the desired antigen, and the host becomes at least partially immune to later infection, or resistant to developing chronic infection.

The peptides of the present invention and pharmaceutical and vaccine compositions of the invention are useful for administration to mammals, particularly humans, to treat and/or prevent cancer. Vaccine compositions containing the peptides of the invention are administered to a patient susceptible to or otherwise at risk of cancer to elicit an immune response against the antigen and thus enhance the patient's own immune response capabilities. Such an amount is defined to be an "immunogenically effective dose." In this use, the precise amounts again depend on the patient's state of health and weight, the mode of administration, the nature of the formulation, etc., but generally range from about 1.0 µg to about 5000 µg per 70 kilogram patient, more commonly from about 10 µg to about 500 µg mg per 70 kg of body weight.

As noted herein, the peptides of the invention induce HTL immune responses when contacted with a HTL specific to an epitope comprised by the peptide. The manner in which the peptide is contacted with the HTL is not critical to the invention. For instance, the peptide can be contacted with the HTL either in vivo or in vitro. If the contacting occurs in vivo, the peptide itself can be administered to the patient or other vehicles, e.g., DNA vectors encoding one or more peptide, viral vectors encoding the peptide(s), liposomes and the like, can be used, as described herein.

For therapeutic or immunization purposes, nucleic acids encoding one or more of the peptides of the invention can also be administered to the patient. A number of methods are conveniently used to deliver the nucleic acids to the patient. For instance, the nucleic acid can be delivered directly, as "naked DNA". This approach is described, for instance, in Wolff et. al., *Science* 247: 1465-68 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles.

The nucleic acids can also be delivered complexed to cationic compounds, such as cationic lipids. Lipid-mediated gene delivery methods are described, for instance, in WO 96/18372; WO 93/24640; Mannino and Gould-Fogerite (1988) *BioTechniques* 6(7): 682-691; Rose U.S. Pat. No. 5,279,833; WO 91/06309; and Felgner et al. (1987) *Proc. Natl. Acad. Sci. USA* 84: 7413-14.

Nucleic acids encoding one or more of the peptides of the invention can also be administered to the patient. This approach is described, for instance, in Wolff, et. al., *Science*, 247:1465-68 (1990) as well as U.S. Pat. Nos. 5,580,859 and 5,589,466.

A preferred means of administering nucleic acids encoding the peptides of the invention uses minigene constructs encoding multiple epitopes of the invention. To create a DNA sequence encoding the selected HTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: a leader (signal) sequence, and an endoplasmic reticulum retention signal. In addition, MHC presentation of HTL epitopes may be improved by including synthetic (e.g. poly-alanine) or naturally-occurring flanking sequences adjacent to the HTL epitopes.

The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the HTL epitope polypeptide, can then cloned into a desired expression vector.

Standard regulatory sequences well known to those of skill in the art are included in the vector to ensure expression in the target cells. Several vector elements are required: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences can also be considered for increasing minigene expression. It has recently been proposed that immunostimulatory sequences (ISSs or CpGs) play a role in the immunogenicity of DNA vaccines. These sequences could be included in the vector, outside the minigene coding sequence, if found to enhance immunogenicity.

In some embodiments, a bicistronic expression vector, to allow production of the minigene-encoded epitopes and a second protein included to enhance or decrease immunogenicity can be used. Examples of proteins or polypeptides that could beneficially enhance the immune response if co-expressed include cytokines (e.g., IL2, IL12, GM-CSF), cytokine-inducing molecules (e.g., LeIF) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-β) may be beneficial in certain diseases.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

Therapeutic quantities of plasmid DNA are produced by fermentation in *E. coli*, followed by purification. Aliquots from the working cell bank are used to inoculate fermentation medium (such as Terrific Broth), and grown to saturation in shaker flasks or a bioreactor according to well known techniques. Plasmid DNA can be purified using standard bioseparation technologies such as solid phase anion-exchange resins supplied by Quiagen. If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). A variety of methods have been described, and new techniques may become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

The nucleic acids can also be administered using ballistic delivery as described, for instance, in U.S. Pat. No. 5,204, 253. Particles comprised solely of DNA can be administered. Alternatively, DNA can be adhered to particles, such as gold particles.

In vivo immunogenicity is a second approach for functional testing of minigene DNA formulations. Transgenic mice expressing appropriate human MHC molecules are immunized with the DNA product. The dose and route of administration are formulation dependent (e.g. IM for DNA in PBS, IP for lipid-complexed DNA). Twenty-one days after immunization, splenocytes are harvested and restimulated for 1 week in the presence of peptides encoding each epitope being tested.

An embodiment of a vaccine composition in accordance with the invention comprises ex vivo administration of a cocktail of epitope-bearing peptides to PBMC, or isolated DC therefrom, from the patient's blood. After pulsing the DC with peptides and prior to reinfusion into patients, the DC are washed to remove unbound peptides. In this embodiment, a vaccine comprises peptide-pulsed DCs which present the pulsed peptide epitopes in HLA molecules on their surfaces.

Dendritic cells can also be transfected, e.g., with a minigene comprising nucleic acid sequences encoding the epitopes in accordance with the invention, in order to elicit immune responses. Vaccine compositions can be created in vitro, following dendritic cell mobilization and harvesting, whereby loading of dendritic cells occurs in vitro.

Transgenic animals of appropriate haplotypes may additionally provide a useful tool in optimizing the in vivo immunogenicity of minigene DNA. In addition, animals such as monkeys having conserved HLA molecules with cross reactivity to CTL epitopes recognized by human MHC molecules can be used to determine human immunogenicity of CTL epitopes (Bertoni, et al., *J. Immunol.* 161:4447-4455 (1998)).

Such in vivo studies are required to address the variables crucial for vaccine development, which are not easily evaluated by in vitro assays, such as route of administration, vaccine formulation, tissue biodistribution, and involvement of primary and secondary lymphoid organs. Because of their simplicity and flexibility, HLA transgenic mice represent an attractive alternative, at least for initial vaccine development studies, compared to more cumbersome and expensive studies in higher animal species, such as nonhuman primates.

Antigenic peptides are used to elicit a HTL response ex vivo, as well. The resulting HTL cells, can be used to treat tumors in patients that do not respond to other conventional forms of therapy, or will not respond to a therapeutic vaccine peptide or nucleic acid in accordance with the invention. Ex vivo HTL responses to a particular antigen are induced by incubating in tissue culture the patient's (HTLp), or genetically compatible, HTL precursor cells together with a source of antigen-presenting cells (APC), such as dendritic cells, and the appropriate immunogenic peptide. After an appropriate incubation time (typically about 7-28 days (1-4 weeks)), in which the precursor cells are activated and matured and expanded into effector cells, the cells are infused back into the patient, where they will destroy their specific target cell (an infected cell or a tumor cell). Transfected dendritic cells may also be used as antigen presenting cells. In order to optimize the in vitro conditions for the generation of specific helper T cells, the culture of stimulator cells is maintained in an appropriate serum-free medium.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic infection.

For example, a peptide of the invention may be used in a tetramer staining assay to assess peripheral blood mononuclear cells for the presence of antigen-specific CTLs following exposure to a pathogen or immunogen. The HLA-tetrameric complex is used to directly visualize antigen-specific CTLs (see, e.g., Ogg, et al. *Science* 279:2103-2106, 1998; and Altman, et al. *Science* 174:94-96, 1996) and determine the frequency of the antigen-specific CTL population in a sample of peripheral blood mononuclear cells. A tetramer reagent using a peptide of the invention may be generated as follows: A peptide that binds to an allele-specific HLA molecule or supertype molecule is refolded in the presence of the corresponding HLA heavy chain and $\beta_2$-microglobulin to generate a trimolecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells may then be identified, for example, by flow cytometry. Such an analysis may be used for diagnostic or prognostic purposes. In addition, the peptides may also be used to predict which individuals will be at substantial risk for developing chronic infection.

All publications, patents, and patent applications cited in this specification are herein incorporated by reference as if each individual publication, patent or patent application were specifically and individually indicated to be incorporated by reference. Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

Materials and Methods

The following materials and methods apply generally to all the examples disclosed herein. Specific materials and methods are disclosed in each example, as necessary.

Reagents:

Anti-IFN-γ and biotinylated anti-IFN-γ were obtained from Mabtech (Sweden). Phorbol myristate acetate (PMA), human serum albumin (HSA), polyclonal human IgG, tetanus toxin (TT), and ionomycin were from Sigma (St. Louis, Mo., USA). Goat anti-human horseradish peroxidase (HRP)-conjugated antibody was obtained from Santa Cruz Biotechnology (Santa Cruz, Calif.). Hank's balanced salts solution (HBSS), RPMI-1640 and phosphate-buffered saline were from Cellgro (Hernden, Va., USA). Ficoll-Paque was from Amersham Biosciences (Uppsala, Sweden). All peptides were synthesized by either the Mayo Clinic Protein Chemistry and Proteomics Core or by Epimmune, Inc. (San Diego, Calif.) and purified to >95% homogeneity by reverse-phase HPLC as previously described (Dzuris J L, Sidney J, Appella E, Chesnut R W, Watkins D I, Sette A. Conserved MHC class I peptide binding motif between humans and rhesus macaques. J Immunol 2000; 164: 283-91). Purity of peptides was determined with reverse-phase HPLC and amino acid analysis, sequencing, and/or mass spectrometry. Lyophilized peptides were resuspended at 20 mg/ml in 100% DMSO and then diluted to required concentrations in PBS.

Epitope Prediction:

The prediction program used, PIC (Predicted $IC_{50}$), is a modified linear coefficient, or matrix-based method for predicting peptides with HLA-DR binding capacity. PIC is predicated on the assumption that each residue along a peptide molecule can independently contribute to binding affinity (Sette A, et al. Proc Natl Acad Sci USA 1989; 86: 3296-300; Sette A, et al. J Immunol 1989; 142: 35-40). The algorithm yields a predicted $IC_{50}$ value (designated as PIC) for the corresponding input sequence. Lower PIC values indicate a higher probability of binding to HLA. The program analyzes 15 amino acid long sequences offset by 3 residues encompassing the entire protein.

Peripheral Blood Mononuclear Cell Preparation (PBMC):

PBMC were isolated from blood as described (Disis M L, et al. Clin Cancer Res 1999; 5: 1289-97), and cryopreserved in liquid nitrogen (20×106/ml cells) in freezing media (RPMI with 12.5% HSA, penicillin, streptomycin and 2 mM glutamine) (Disis M L et al. J Immunol Methods 2005.).

HLA-DR Purification.

Fifteen distinct HLA-DR molecules were used in quantitative assays to measure the binding of peptides to solubilized HLA-DR molecules. These HLA-DR molecules were chosen to allow balanced population coverage: DRB1*0101, DRB1*1501, DRB1*0301, DRB1*0401, DRB1*0404, DRB1*1101, DRB5*0101, DRB4*0101, DRB3*0101, DRB1*0701, DRB1*0405, DRB1*0802, DRB1*0901, DRB1*1201, and DRB1*1302 (24). MHC molecules utilized were purified from EBV transformed homozygous cell lines or single MHC allele transfected 721.221, C1R, or fibroblast lines. The cell lines were maintained by culture in RPMI-1640 medium supplemented with 2 mM L-glutamine, 100 U (100 μg/ml) penicillin-streptomycin solution, and 10% heat-inactivated FCS. HLA-DR molecules were purified using antibody-based affinity chromatography from cell lysates prepared in 50 mM Tris-HCL, pH 8.5, containing 1% (v/v) NP-40, 150 mM NaCl, 5 mM EDTA, and 2 mM PMSF. Briefly, columns of inactivated Sepharose CL4B and Protein A Sepharose were used as pre-columns. HLA-DR molecules were captured by passage of lysates over LB3.1 monoclonal antibody (anti-HLA-DRA) columns. Antibody columns were washed with 10 mM Tris-HCL, pH8.0 with 1% (v/v) NP-40, followed by PBS containing 0.4% (w/v) n-octylglucoside. MHC molecules were then eluted with 50 mM diethylamine in 0.15 M NaCl containing 0.4% (w/v) n-octylglucoside, pH 11.5. The pH was reduced to 8.0 and the eluates were concentrated by centrifugation in Centriprep 30 concentrators at 2000 rpm (Amicon, Beverly, Mass.).

HLA-DR Binding Assays:

Radioligand binding inhibition assays were used to measure the binding of peptides to soluble HLA-DR molecules based on the inhibition of binding of a radiolabeled standard peptide as described previously (Sidney J, Southwood S, Oseroff C, del Guercio M F, Grey H M, Sette A. Measurement of MHC/peptide interactions by gel filtration. Curr Protocols Immunol 1998; 18: 18.3.2-.3.9.). Briefly, 1-10 nM of radiolabeled peptide was co-incubated for 2 days at either room temperature or 37° C. with 1 µM to 1 nM purified HLA-DR molecules in the presence of a cocktail of protease inhibitors. Assays were performed at various pH conditions, ranging from pH 4 to pH 7. The final pH of assay mixtures is adjusted using citrate buffer as described elsewhere (Sidney J, Curr Protocols Immunol 1998). After incubation, the percentage of HLA-DR-bound radioactivity is determined by capturing HLA-DR/peptide complexes on Optiplates (Packard Instruments, Meriden, Conn.) coated with the LB3.1 antibody and determining bound counts per minute using the TopCount microscintillation counter (Packard Instruments). The amount of HLA-DR yielding 10-20% bound radioactivity is used in the inhibition assays in which the concentration of peptide yielding 50% inhibition of the binding of the radiolabeled peptide was calculated. Under the conditions used, the measured $IC_{50}$ values are reasonable approximations of the true Kd values. Competitor peptides are tested in 2-4 complete, independent experiments, at concentrations ranging from 30 µg/mL to 300 pg/mL. As in previous studies, peptides with affinities for specific HLA-DR molecules of 1000 nM or better are defined as binders for the respective antigens.

Enzyme-linked immunosorbent spot assay. A 10-day ELIspot for detecting low-frequency T cells was used to determine reactivity to the tumor antigen peptides (Table 1) as described (Knutson K L et al. J Clin Onc 2006; 24: 4254-61). A positive response to a peptide was defined as a frequency that was significantly (p<0.05, two-tailed t test) greater than the mean of control no-antigen wells and detectable (i.e., >1:100,000). PMA/Ionomycin and the CEF pool were used as positive non-tumor related controls as previously described (Knutson, 2006).

ELISA. ELISAs were done as previously described (Knutson, 2006). Briefly, 96-well plates were coated with 1 µg/ml IGFBP-2 protein, 200 ng/ml tetanus toxin or 1 µg/ml BSA. Human IgG was added at a concentration range of 200 to 0.2 ng/ml to some wells for standard curve generation. After washing and blocking, human sera were added to the plate at a 1:40 dilution in triplicate and plates were incubated for 2 hr at RT. After washing, 100 µL/well of HRP (Santa Cruz Biotechnology) was diluted 1:2000 and incubated for 1 hr at RT. After a final wash, each well was incubated with 100 µL (tetramethylbenzadine) TMB substrate (BD Bioscience). Color development was stopped with diluted HCL and absorbance was read at 450 nm on a plate reader.

The following examples are provided by way of illustration only and not by way of limitation. Those of skill in the art will readily recognize a variety of non-critical parameters that could be changed or modified to yield essentially similar results.

Example 1

Identification of Conserved HLA Class II-Restricted Peptides Derived from Tumor Associated Antigens Using Established Motif Search Algorithms To identify epitopes useful for vaccine design, a multi-disciplinary approach was used based initially on amino acid motif searching of tumor associated antigen sequences to identify potential HLA Class II motifs (see Table I). This was followed by high throughput synthetic peptide binding assays using purified HLA molecules to determine affinity and breadth of epitope peptide binding.

Algorithm Motif Searches:

Motif search algorithms were validated for the most common HLA Class II alleles and were focused on the HLA DRB1*0101, DRB1*1501, DRB1*0301, DRB1*0401, DRB1*0404, DRB1*1101, DRB5*0101, DRB4*0101, DRB3*0101, DRB1*0701, DRB1*0405, DRB1*0802, DRB1*0901, DRB1*1201, and DRB1*1302 supertypes in order to attain virtually 100% population coverage. The selected tumor associated antigen sequences were scanned for motif positive amino acid sequences using the motif definitions.

A total of about 150 Class II-restricted peptide sequences were identified that were specific for various DR supertypes (see Table I). Table I lists for each identified DR antigen peptide, the $IC_{50}$ (nM) for each purified HLA.

Example 2

Identification of HTL Epitopes for Tumor Vaccine Inclusion

Figure 2:
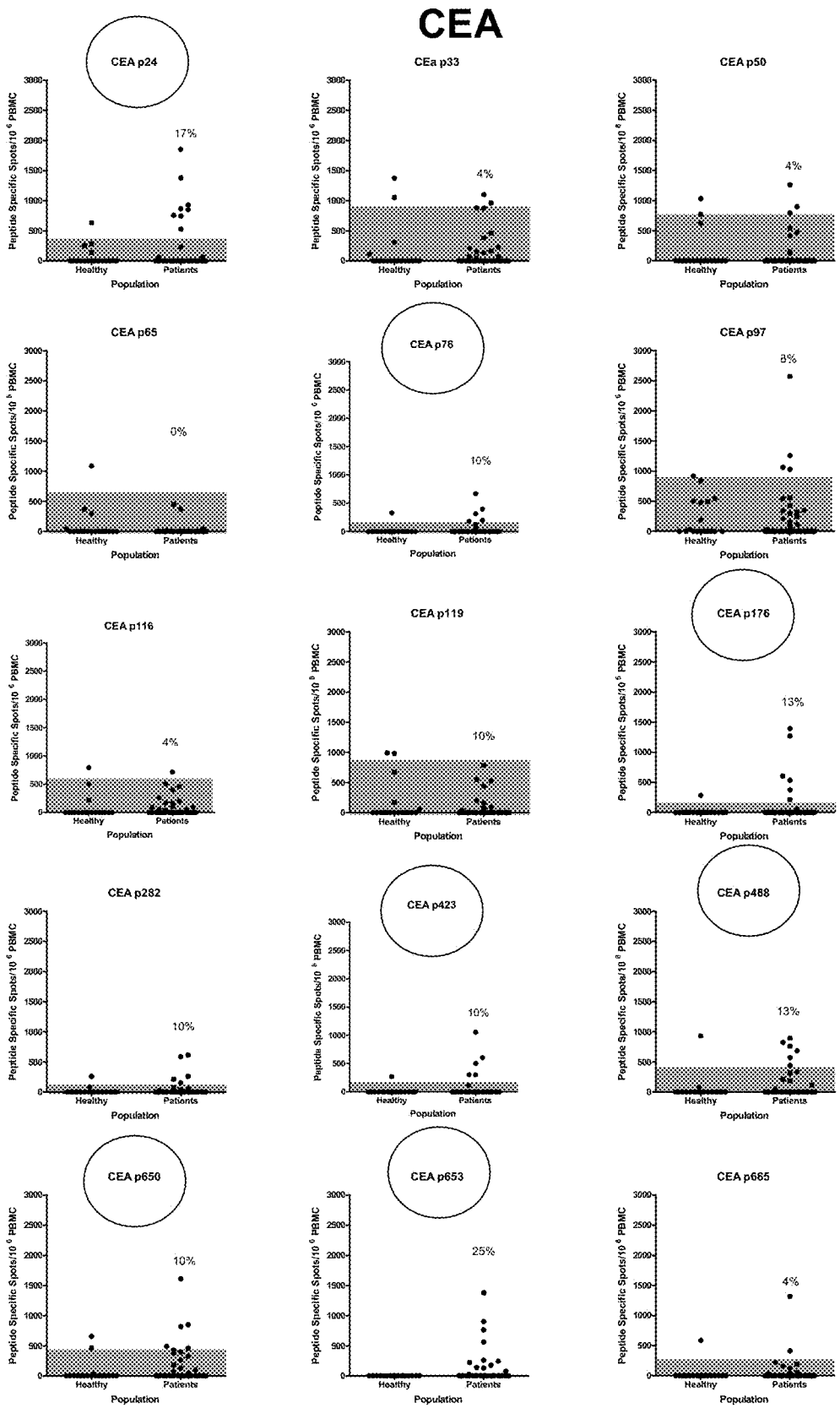
FIG. 2 shows the identification of preexistent immunity to promiscuous CEA HLA-DR epitopes.
Figure 3:
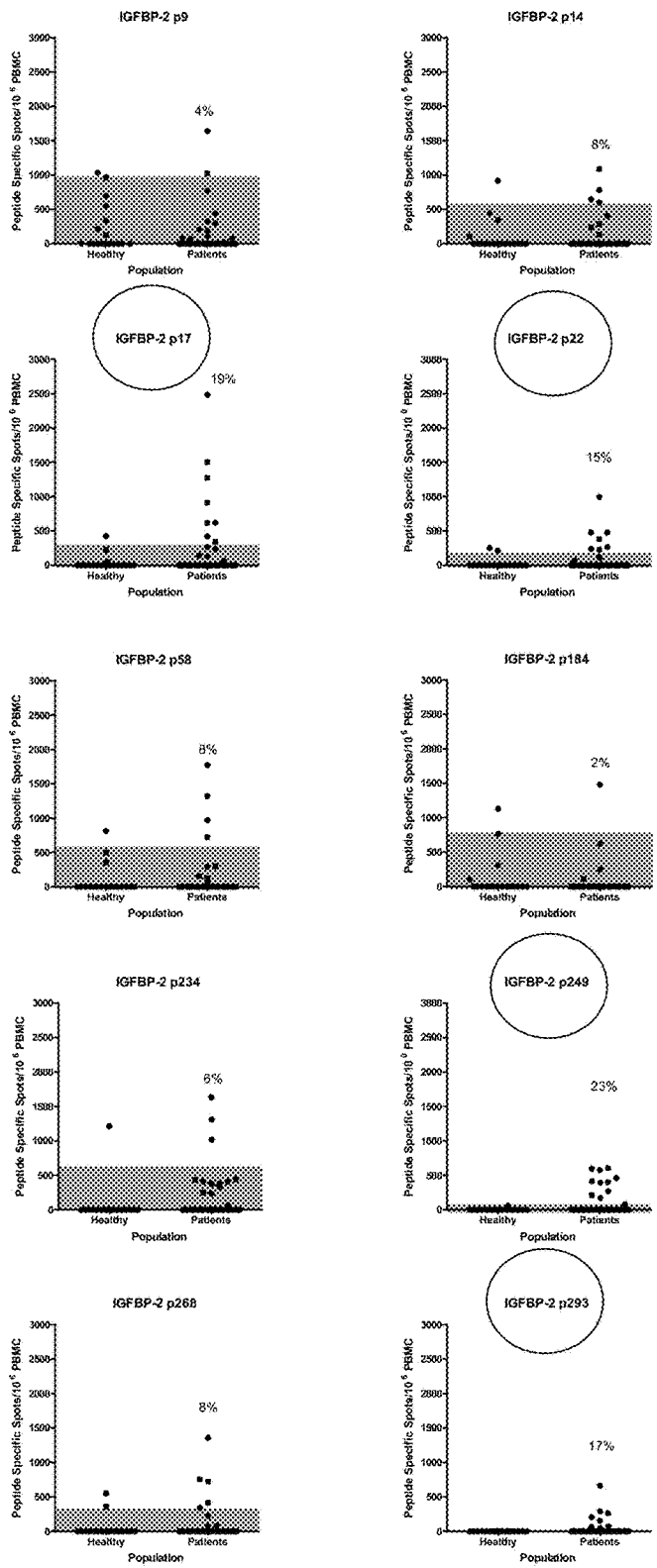
FIG. 3 shows the identification of preexistent immunity to promiscuous IGFBP2 HLA-DR epitopes.
Figure 4:
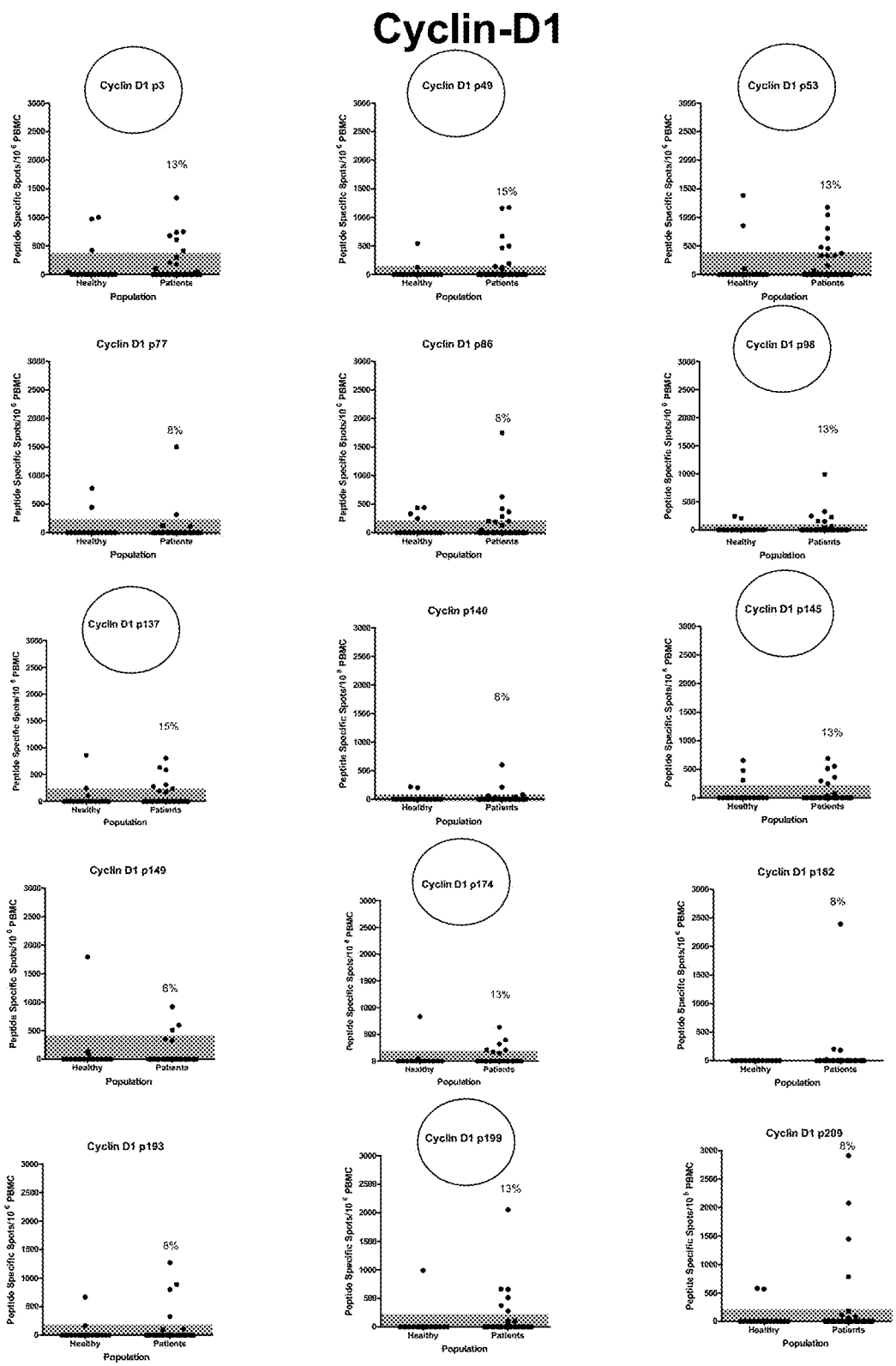
FIG. 4 shows the identification of preexistent immunity to promiscuous IGFBP2 HLA-DR epitopes.
Figure 5:
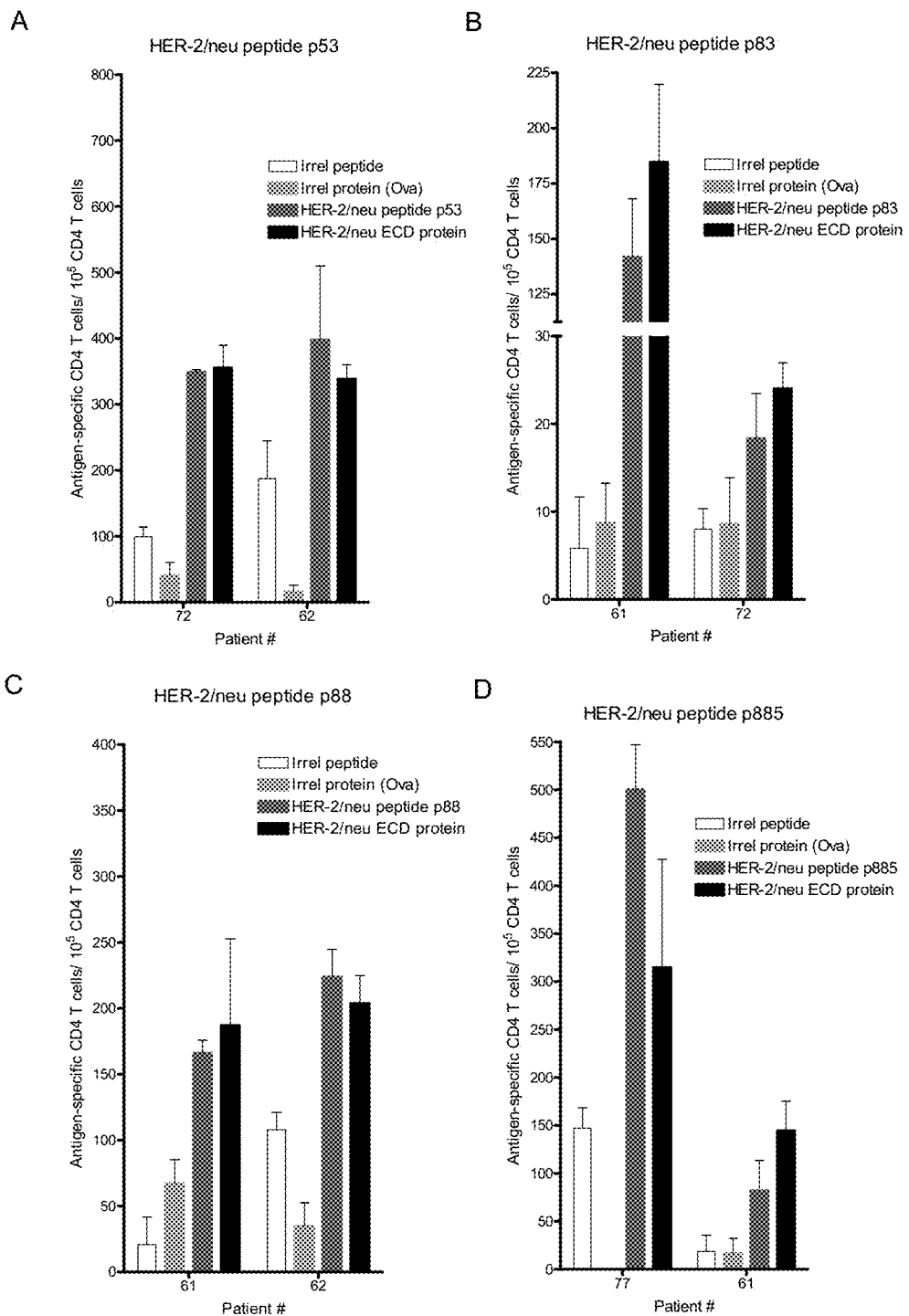
FIG. 5 shows the that HER-2/neu peptides, p59, p83, p88 and p885 are naturally processed and presented antigens. IFN-γ ELISpot analysis of short term T cell lines generated against HER-2/neu peptides, p53 (Panel A), p83 (Panel B), p88 (Panel C) and p885 (Panel D). The lines were tested for responses against respective culture peptides, an irrelevant 15-mer peptide, a HER-2/neu protein fragment (amino acids 22-122, Panels A-C; amino acids 676-1255, Panel D), or an irrelevant similar weight protein, ovalbumin. Each shows the results from two lines established from two different breast or ovarian cancer patients who had a positive ELIspot response to the peptide. Each bar is the mean (s.e.m.) of three replicates.
Figure 6:
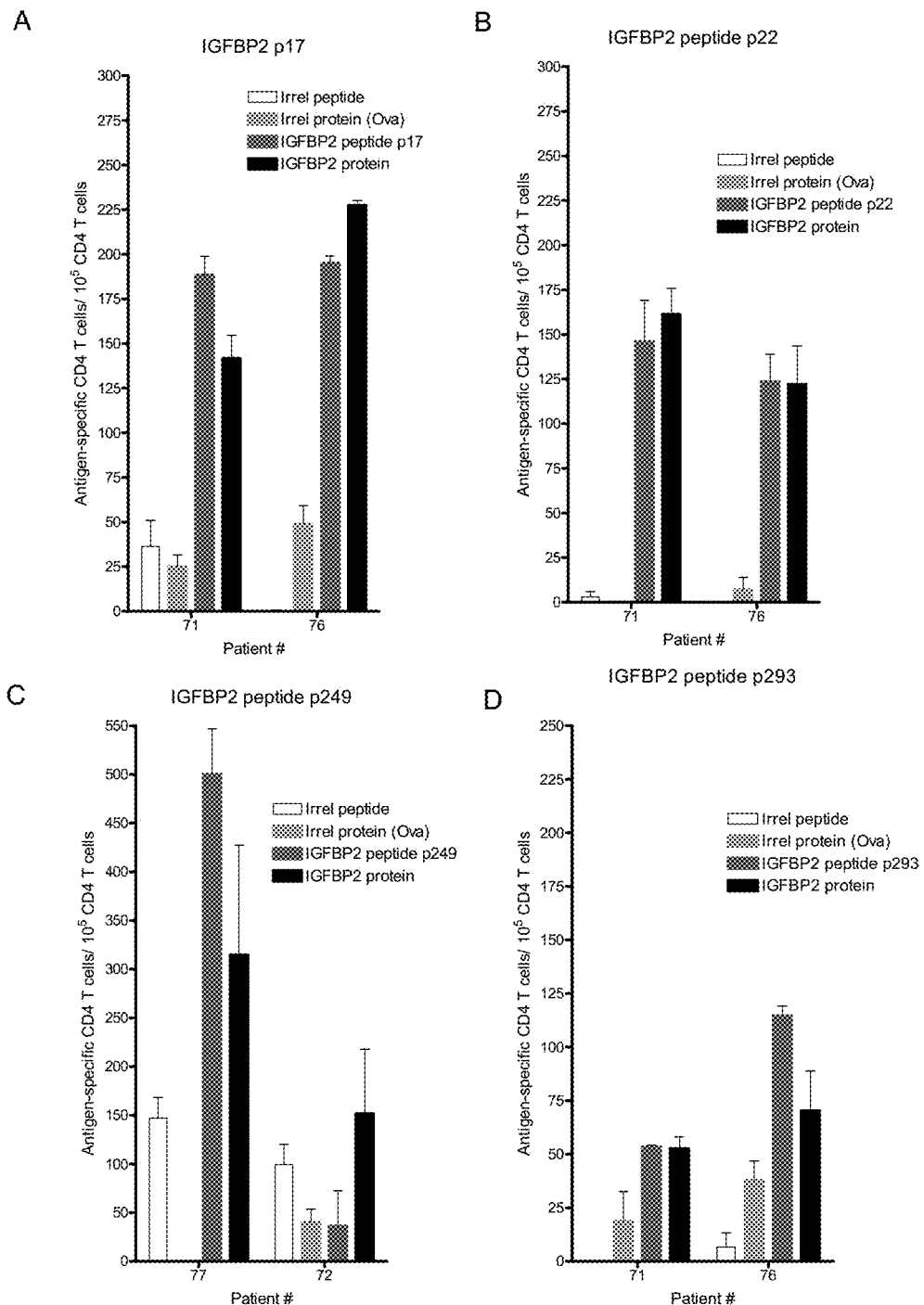
FIG. 6 shows that IGFBP2 peptides p17, p22, p249, and p293 are naturally processed peptides.

Of the peptides listed in Table I, those peptides that bound to at least 4 different HLA with an $IC_{50}$ of less than 1000 nM were identified and are shown in Table II. The peptide sequences of Table II were further evaluated for their binding capacity to purified MHC molecules. FIGS. 1 through 4 show those peptides of Table II which were immunogenic (shown in a circle). These HTL peptides are candidates for inclusion into a tumor vaccine.

Using predictive algorithms discussed above, candidate HLA-DR1-binding epitopes were identified. Binding assays targeting 15 different HLA-DR molecules revealed that 10 of the epitopes were indiscriminate, binding ($IC_{50}$<1000 nM) to at least four different HLA-DR variants. An interferon-gamma ELIspot assay was used to assess immunity to the indiscriminate binding peptides in 48 patients with either breast or ovarian cancer and 18 healthy controls. The results showed that elevated T cell immunity in patients was detected to several peptides (FIGS. 1-4).

Healthy donor and patient samples were obtained. Patients were free from active treatment for at least 30 days when blood (200 ml) was collected. For the T cell studies, the mean (±s.e.m) ages of the healthy donors and patients were 42±11 and 55±2 years, respectively (p<0.0001). Due to sera unavailability, not all of the controls used in the T cell studies were examined for tumor associated antigen antibodies in their sera. However, additional control and patient sera were available for antibody assessment. Additional healthy donor sera was obtained from Bioreclamation (Hicksville, N.Y.).

Using an ELIspot assay with a limit of detection of approximately 1:100,000 antigen-specific T cells per million PBMC, patient-derived PBMC were screened for reactivity against all of the HLA-DR binding peptides. The immunogenicity data of several peptides is shown in FIGS. 1-4.

Example 3

Design and Development of Multi-Epitope Vaccines

Peptides that bound to at least 4 different HLA subtypes as described above, and were shown to be immunogenic, as shown in FIGS. 1-4, were selected for inclusion in a multi-epitope vaccine. Table III shows the percent of patients that demonstrated positive responses and the binding patterns to specific HLA subtypes of eight vaccine candidates.

These example and equivalents thereof will become more apparent to those skilled in the art in light of the present disclosure and the accompanying claims. It should be understood, however, that the examples are designed for the purpose of illustration only and not limiting of the scope of the invention in any way.

TABLE I

HLA-DR binding affinity of Breast/Ovarian-derived peptides

| | | | | | IC$_{50}$ μM to purified HLA | | | | |
|---|---|---|---|---|---|---|---|---|---|
| Peptide | Sequence | Source | Protein | Position | DRB1 *0101 | DRB1 *0301 | DRB1 *0401 | DRB1 *0404 | DRB1 *0405 |
| 9019.0104 | RWCIPWQRLLLTASL | CEA.10 | CEA | 10 | 1467 | 7860 | 426 | 193 | 221 |
| 9019.0105 | LLTFWNPPTTAKLTI | CEA.24 | CEA | 24 | 6.9 | 16.313 | 273 | 52 | 258 |
| 9019.0106 | TAKLTIESTPFNVAE | CEA.33 | CEA | 33 | 72 | 613 | 106 | 41 | 383 |
| 9019.0107 | EVLLLVHNLPQHLFG | CEA.50 | CEA | 50 | 2.7 | 830 | 3.4 | 1.7 | 30 |
| 9019.0108 | YSWYKGERVDGNRQI | CEA.65 | CEA | 65 | 511 | — | 34 | 585 | 360 |
| 9019.0109 | NRQIIGYVIGTQQAT | CEA.76 | CEA | 76 | 216 | — | 108 | 1.5 | 129 |
| 9019.0110 | GYVIGTQQATPGPAY | CEA.81 | CEA | 81 | 21 | | 31 | 34 | 4210 |
| 9019.0111 | GPAYSGREIIYPNAS | CEA.92 | CEA | 92 | 9435 | | 12.989 | | |
| 9019.0112 | GREIIYPNASLLIQN | CEA.97 | CEA | 97 | 62 | 433 | 251 | 88 | 550 |
| 9019.0113 | DTGFYTLHVIKSDLV | CEA.116 | CEA | 116 | 64 | 984 | 84 | 260 | 95 |
| 9019.0114 | FYTLHVIKSDLVNEE | CEA.119 | CEA | 119 | 101 | 80 | 184 | 169 | 41 |
| 9019.0005 | LHVIKSDLVNEEATG | CEA.122 | CEA | 122 | 891 | 46 | 214 | 103 | 37 |
| 9019.0115 | KSDLVNEEATGQFRV | CEA.126 | CEA | 126 | 13.600 | 2530 | 236 | | |
| 9019.0116 | QFRVYPELPKPSISS | CEA.137 | CEA | 137 | 1780 | 1727 | 2916 | | |
| 9019.0117 | KPSISSNNSKPVEDK | CEA.146 | CEA | 146 | 405 | | 919 | 2111 | 6959 |
| 9019.0118 | YLWWVNNQSLPVSPR | CEA.176 | CEA | 176 | 2.4 | 100 | 832 | 203 | 80 |
| 9019.0119 | SDSVILNVLYGPDAP | CEA.226 | CEA | 226 | 111 | | 255 | 314 | 1453 |
| 9019.0120 | LNVLYGPDAPTISPL | CEA.231 | CEA | 231 | 331 | | 649 | 1378 | — |
| 9019.0121 | APTISPLNTSYRSGE | CEA.239 | CEA | 239 | 2431 | | 295 | 49 | 5994 |
| 9019.0122 | QYSWFVNGTFQQSTQ | CEA.268 | CEA | 268 | 5983 | | 21 | 7830 | 364 |
| 9019.0123 | QELFIPNITVNNSGS | CEA.282 | CEA | 282 | 147 | 644 | 25 | 227 | 379 |
| 9019.0124 | RTTVTTITVYAEPPK | CEA.310 | CEA | 310 | 4115 | | 259 | 697 | 32 |
| 9019.0125 | TITVYAEPPKPFITS | CEA.315 | CEA | 315 | 12.755 | 539 | — | 12.658 | 5704 |
| 9019.0126 | YLWWVNNQSLPVSPR | CEA.354 | CEA | 354 | 1123 | 234 | 12 | 248 | 88 |
| 9019.0127 | SDPVILNVLYGPDDP | CEA.404 | CEA | 404 | 384 | | 592 | 347 | 3732 |
| 9019.0128 | SYTYYRPGVNLSLSC | CEA.423 | CEA | 423 | 1.6 | 4425 | 6.8 | 4036 | 300 |
| 9019.0129 | YSWLIDGNIQQHTQE | CEA.447 | CEA | 447 | 1407 | | 95 | | |
| 9019.0130 | NSGLYTCQANNSASG | CEA.471 | CEA | 471 | 49 | | 33 | 37 | 96 |
| 9019.0131 | RTTVKTITVSAELPK | CEA.488 | CEA | 488 | 89 | 1267 | 58 | 54 | 11 |
| 9019.0132 | TITVSAELPKPSISS | CEA.493 | CEA | 493 | 223 | 74 | 9393 | 6997 | 3624 |
| 9019.0133 | KPSISSNNSKPVEDK | CEA.502 | CEA | 502 | 146 | | 403 | 1404 | 5564 |
| 9019.0134 | YLWWVNGQSLPVSPR | CEA.532 | CEA | 532 | 1.4 | | 2.5 | 1356 | 188 |
| 9019.0135 | VCGIQNSVSANRSDP | CEA.570 | CEA | 570 | 44 | | 72 | 26 | 1854 |
| 9019.0136 | QNSVSANRSDPVTLD | CEA.574 | CEA | 574 | 240 | | 511 | 1432 | — |
| 9019.0137 | SSYLSGANLNLSCHS | CEA.603 | CEA | 603 | 40 | | 580 | 1596 | 7822 |
| 9019.0138 | QYSWRINGIPQQHTQ | CEA.624 | CEA | 624 | 472 | | 43 | 1203 | 311 |
| 9019.0139 | INGIPQQHTQVLFIA | CEA.629 | CEA | 629 | 682 | | 181 | 680 | 942 |
| 9019.0140 | NGTYACFVSNLATGR | CEA.650 | CEA | 650 | 839 | 818 | 11 | 558 | 30 |
| 9019.0141 | YACFVSNLATGRNNS | CEA.653 | CEA | 653 | 183 | 774 | 225 | 41 | 327 |
| 9019.0142 | NNSIVKSITVSASGT | CEA.665 | CEA | 665 | 34 | 103 | 43 | 1.8 | 128 |
| 9019.0143 | SITVSASGTSPGLSA | CEA.671 | CEA | 671 | 2807 | | 75 | 11 | 3374 |
| 9019.0144 | SPGLSAGATVGIMIG | CEA.680 | CEA | 680 | 3507 | | 4191 | 2000 | 2380 |
| 1622.05 | TVGIMIGVLVGVALI | CEA.688 | CEA | 688 | 384 | | — | | |
| 9019.0006 | HQLLCCEVETIRRAY | Cyclin D1.3 | Cyclin D1 | 3 | 953 | 21 | 746 | 256 | 4200 |
| 9019.0146 | DANLLNDRVLRAMLK | Cyclin D1.19 | Cyclin D1 | 19 | 1463 | | 2342 | | |
| 9019.0147 | NDRVLRAMLKAEETC | Cyclin D1.24 | Cyclin D1 | 24 | 1174 | | 1963 | | |
| 9019.0148 | RAMLKAEETCAPSVS | Cyclin D1.29 | Cyclin D1 | 29 | 407 | | 360 | 375 | 12.517 |
| 9019.0149 | FKCVQKEVLPSMRKI | Cyclin D1.45 | Cyclin D1 | 45 | 4099 | | 315 | | |
| 9019.0012 | QKEVLPSMRKIVATW | Cyclin D1.49 | Cyclin D1 | 49 | 5825 | 111 | 12.182 | 1102 | 3720 |
| 9019.0150 | LPSMRKIVATWMLEV | Cyclin D1.53 | Cyclin D1 | 23 | 8.5 | 826 | 238 | 28 | 123 |
| 9019.0151 | MRKIVATWMLEVCEE | Cyclin D1.56 | Cyclin D1 | 26 | 764 | | 7953 | — | 1982 |
| 9019.0011 | MLEVCEEQKGEEEVF | Cyclin D1.64 | Cyclin D1 | 64 | | — | | | |
| 9019.0152 | EEFVTPLAMNYLDRF | Cyclin D1.74 | Cyclin D1 | 74 | 850 | | 2247 | 3070 | 2228 |
| 9019.0153 | VFPLAMNYLDRFLSL | Cyclin D1.77 | Cyclin D1 | 77 | 146 | 107 | 2332 | 1567 | 609 |
| 9019.0007 | DRFLSLEPVKKSRLQ | Cyclin D1.86 | Cyclin D1 | 86 | 16 | 290 | 18 | 61 | 150 |
| 9019.0154 | DRFLSLEPVKKSRLQ | Cyclin D1.86 | Cyclin D1 | 86 | 15 | | 80 | 80 | 251 |
| 9019.0155 | LEPVKKSRDQLLGAT | Cyclin D1.91 | Cyclin D1 | 91 | 102 | | 5112 | 696 | 13.689 |
| 9019.0156 | RLQLLGATCMFVASK | Cyclin D1.98 | Cyclin D1 | 98 | 12 | — | 91 | 633 | 1439 |
| 9019.0157 | TCMFVASKMKETIPL | Cyclin D1.105 | Cyclin D1 | 105 | 262 | | 342 | 5454 | 1744 |
| 9019.0158 | ASKMKETIPLTAEKL | Cyclin D1.110 | Cyclin D1 | 110 | 130 | | | 1992 | — |
| 1622.01 | TIPLTAEKLCLYTDN | Cyclin D1.116 | Cyclin D1 | 116 | 253 | 11.708 | 1230 | — | |
| 9019.0159 | KLCIYTDNSIRPEEL | Cyclin D1.123 | Cyclin D1 | 123 | 1915 | 64 | 95 | 241 | 3172 |
| 9019.0009 | DNSIRPEELLQMELL | Cyclin D1.129 | Cyclin D1 | 129 | 4554 | 147 | 4677 | 2803 | 16.500 |
| 9019.0160 | DNSIRPEELLQMELL | Cyclin D1.129 | Cyclin D1 | 129 | 1533 | | 1345 | | |
| 9019.0161 | PEELLQMELLLVNKL | Cyclin D1.134 | Cyclin D1 | 134 | 1274 | | 1027 | 318 | 603 |
| 9019.0010 | EELLQMELLLVNKLK | Cyclin D1.135 | Cyclin D1 | 135 | | 3386 | | | |
| 1622.06 | LLQMELLLVNKLKWN | Cyclin D1.135 | Cyclin D1 | 137 | 39 | — | 3939 | 6.4 | 332 |
| 9019.0163 | MELLLVNKLKWNLAA | Cyclin D1.140 | Cyclin D1 | 140 | 46 | 9006 | 177 | 481 | 2411 |
| 9019.0164 | VNKLKWNLAAMTPHD | Cyclin D1.145 | Cyclin D1 | 145 | 46 | 1419 | 68 | 781 | 747 |
| 9019.0165 | KWNLAAMTPHDFIEH | Cyclin D1.149 | Cyclin D1 | 149 | 33 | 6249 | 3405 | 653 | 122 |
| 9019.0013 | WNLAAMTPHDFIEHF | Cyclin D1.150 | Cyclin D1 | 150 | | 6425 | | | |
| 9019.0166 | PHDFIEHFLSKMPEA | Cyclin D1.157 | Cyclin D1 | 157 | 1246 | | 1299 | | |
| 9019.0167 | NKQIIRKHAQTFVAL | Cyclin D1.174 | Cyclin D1 | 174 | 4.7 | 561 | 6.5 | 23 | 25 |

TABLE I-continued

HLA-DR binding affinity of Breast/Ovarian-derived peptides

| ID | Sequence | Name | Protein | Pos | | | | | |
|---|---|---|---|---|---|---|---|---|---|
| 9019.0168 | AQTFVALCATDYKFI | Cyclin D1.182 | Cyclin D1 | 182 | 8.4 | 551 | 26 | 133 | 55 |
| 9019.0169 | VKFISNPPSMVAAGS | Cyclin D1.193 | Cyclin D1 | 193 | 6.7 | 4126 | 12 | 14 | 117 |
| 9019.0170 | PPSMVAAGSVVAAVQ | Cyclin D1.199 | Cyclin D1 | 199 | 6.8 | — | 12 | 26 | 1718 |
| 9019.0171 | VAAVQGLNLRSPNNF | Cyclin D1.209 | Cyclin D1 | 209 | 44 | 18.558 | 226 | 532 | 4248 |
| 9019.0172 | IEALLESSLRQAQQN | Cyclin D1.251 | Cyclin D1 | 251 | 2608 | | 18 | | |
| 9019.0014 | EALLESSLRQAQQNM | Cyclin D1.252 | Cyclin D1 | 252 | 8212 | 151 | 605 | 1019 | 12.905 |
| 9019.0024 | LAALCRWGLLLALLP | Her2/neu.3 | Her2.neu | 3 | 2044 | | 5394 | | |
| 9019.0025 | WGLLLALLPPGAAST | Her2/neu.9 | Her2.neu | 9 | 1687 | | 750 | 0.93 | 219 |
| 1622.02 | LLALLPPGAASTQVC | Her2/neu.12 | Her2.neu | 12 | 17 | | 5148 | 118 | — |
| 9019.0027 | GTDMKLRLPASPETH | Her2/neu.28 | Her2.neu | 28 | 2117 | | 1693 | | |
| 9019.0028 | RHLYQGCQVVQGNLE | Her2/neu.47 | Her2.neu | 47 | 1435 | | 422 | | |
| 9019.0029 | GCQVVQGNLELTYLP | Her2/neu.52 | Her2.neu | 52 | 2600 | | 2739 | | |
| 9019.0030 | NLELTYLPTNASLSF | Her2/neu.59 | Her2.neu | 59 | 49 | 7356 | 6.2 | 2.7 | 38 |
| 9019.0031 | LTYLPTNASLSELQD | Her2/neu.62 | Her2.neu | 62 | 9.7 | 3364 | 19 | 16 | 80 |
| 9019.0032 | IQEVQGYVLLAHNQV | Her2/neu.77 | Her2.neu | 77 | 57 | 7763 | 111 | 178 | 102 |
| 9019.0033 | YVLIAHNQVRQVPLQ | Her2/neu.83 | Her2.neu | 83 | 28 | 454 | 53 | 104 | 1185 |
| 9019.0034 | HNQVRQVPLQRLRIV | Her2/neu.88 | Her2.neu | 88 | 950 | 971 | 840 | 78 | 1303 |
| 9019.0035 | VRQVPLQRIRIVRGT | Her2/neu.91 | Her2.neu | 91 | 3065 | | 1798 | | |
| 9019.0001 | GTQLFEDNYALAVLD | Her2/neu.104 | Her2.neu | 104 | 210 | 29 | 640 | 3923 | 14.921 |
| 9019.0036 | GDPLNNTTPVTGASP | Her2/neu.120 | Her2.neu | 120 | 6356 | | 7461 | | |
| 9019.0037 | TTPVTGASPGGLREL | Her2/neu.126 | Her2.neu | 126 | 992 | | 2447 | 675 | 13.198 |
| 9019.0038 | PGGLRELQLRSLTEI | Her2/neu.134 | Her2.neu | 134 | 732 | | 3397 | 564 | 110 |
| 9019.0039 | TEILKGGVLIQRNPQ | Her2/neu.146 | Her2.neu | 146 | 71 | | 40 | 32 | 760 |
| 9019.0040 | GGVLIQRNPQLCYQD | Her2/neu.151 | Her2.neu | 151 | 142 | | 196 | 93 | 1845 |
| 9019.0041 | NPQLCYQDTILWKDI | Her2/neu.158 | Her2.neu | 158 | 3653 | | 368 | | |
| 9019.0042 | ICELHCPALVTYNTD | Her2/neu.262 | Her2.neu | 263 | 101 | | 754 | 136 | 1627 |
| 9019.0043 | STDVGSCTLVCPLHN | Her2/neu.305 | Her2.neu | 305 | 2872 | | — | | |
| 9019.0044 | CYGLGMEHLREVRAV | Her2/neu.342 | Her2.neu | 342 | 139 | 265 | 1027 | 493 | 5122 |
| 9019.0045 | MEHLREVRAVTASNI | Her2/neu.347 | Her2.neu | 347 | 9.6 | 2970 | 533 | 12 | 200 |
| 9019.0046 | LREVRAVTSANIQEF | Her2/neu.350 | Her2.neu | 350 | 17 | 3913 | 43 | 8.2 | 50 |
| 9019.0047 | CKKGFGSLAFLPESF | Her2/neu.367 | Her2.neu | 367 | 119 | | 121 | 171 | 310 |
| 9019.0048 | PDSFDGDPASNTAPL | Her2/neu.378 | Her2.neu | 378 | 10.101 | 989 | 301 | 9020 | 1724 |
| 9019.0049 | TAPLQPEQLQVFETL | Her2/neu.389 | Her2.neu | 389 | 1112 | 3674 | 2633 | | |
| 9019.0050 | ITGYLYTSAWPDSLP | Her2/neu.406 | Her2.neu | 406 | 96 | | 243 | 1771 | 8.5 |
| 9019.0051 | PDSLPDLSVFQNLQV | Her2/neu.410 | Her2.neu | 410 | — | | — | | |
| 9019.0052 | LSVFQNLQVIRGRIL | Her2/neu.422 | Her2.neu | 422 | 1.3 | 364 | 6.3 | 33 | 26 |
| 9019.0053 | NLQVIRGRILHNGAY | Her2/neu.427 | Her2.neu | 427 | 1.9 | 6879 | 971 | 200 | 3394 |
| 9019.0054 | RGRILHNGAYSLTLQ | Her2/neu.432 | Her2.neu | 432 | 2.4 | 710 | 480 | 129 | 2845 |
| 9019.0055 | SLTLQGLGISWLGLR | Her2/neu.442 | Her2.neu | 442 | 93 | | 143 | 110 | 409 |
| 9019.0056 | GLGISWLGLRSLREL | Her2/neu.447 | Her2.neu | 447 | 50 | | 41 | 163 | 3.1 |
| 9019.0057 | LRSLRELGSGLALIH | Her2/neu.459 | Her2.neu | 459 | 7.1 | — | 896 | 14 | 603 |
| 9019.0058 | GLALIHHNTHLCFVH | Her2/neu.464 | Her2.neu | 464 | 465 | | 434 | 171 | 477 |
| 9019.0059 | NTHLCFVHTVPWDQL | Her2/neu.471 | Her2.neu | 471 | 416 | | 796 | 207 | 116 |
| 9019.0060 | DECVGEGLACHQLCA | Her2/neu.502 | Her2.neu | 502 | 459 | | 1968 | 3405 | 2337 |
| 9019.0061 | GHCWGPGPTQCVNCS | Her2/neu.518 | Her2.neu | 518 | 1913 | | 3740 | | |
| 9019.0062 | SQFKRGQECVEEECRV | Her2/neu.532 | Her2.neu | 532 | 462 | | 1020 | 4549 | — |
| 9019.0063 | ECRVLQGLPREYVNA | Her2/neu.543 | Her2.neu | 543 | 262 | | 706 | 9151 | 812 |
| 9019.0064 | LQGLPREYVNARHCL | Her2/neu.547 | Her2.neu | 547 | 354 | 8995 | 201 | 1444 | 663 |
| 9019.0065 | PSGVKPDLSYMPIWK | Her2/neu.601 | Her2.neu | 601 | 1832 | 1578 | 1525 | | |
| 9019.0066 | ASPLTSIISAVVGIL | Her2/neu.648 | Her2.neu | 648 | 15 | 10.905 | 20 | 36 | 712 |
| 9019.0067 | ISAVVGILLVVVLGV | Her2/neu.655 | Her2.neu | 655 | 5153 | | 420 | 2996 | 447 |
| 9019.0068 | ILLVVVLGVVFGILI | Her2/neu.661 | Her2.neu | 661 | — | | 635 | 3532 | 376 |
| 9019.0069 | VLGVVFGILIKRRQQ | Her2/neu.665 | Her2.neu | 666 | 67 | 2449 | 177 | 335 | 104 |
| 9019.0070 | QQKIRKYTMRRLLQE | Her2/neu.679 | Her2.neu | 679 | 303 | | 3782 | 5396 | — |
| 9019.0071 | IRKYTMRRLLQETEL | Her2/neu.682 | Her2.neu | 682 | 665 | | 2766 | 2305 | 1050 |
| 9019.0072 | MRILKETELRKVKVL | Her2/neu.712 | Her2.neu | 712 | 266 | | 3193 | 1266 | 8030 |
| 9019.0073 | ETELRKVKVLGSGAF | Her2/neu.717 | Her2.neu | 717 | 284 | 19.518 | 246 | 27 | 145 |
| 9019.0074 | KVKVLGSGAFGTVYK | Her2/neu.722 | Her2.neu | 722 | 61 | | 810 | 204 | 10.552 |
| 9019.0075 | GENVKIPVAIKVLRE | Her2/neu.743 | Her2.neu | 743 | 491 | | 1065 | 488 | 2093 |
| 1622.03 | KIPVAIKVLRENTSP | Her2/neu.747 | Her2.neu | 747 | 1505 | | 3856 | 125 | 1178 |
| 9019.0077 | AYVMAGVGSPYVSRL | Her2/neu.771 | Her2.neu | 771 | 92 | | 164 | 171 | 596 |
| 9019.0078 | MAGVGSPYVSRLLGI | Her2/neu.774 | Her2.neu | 774 | 2050 | | 1651 | | |
| 9019.0079 | SRLLGICLTSTVQLV | Her2/neu.783 | Her2.neu | 783 | 80 | 2923 | 85 | 13 | 90 |
| 9019.0080 | TVQLVTQLMPYGCLL | Her2/neu.793 | Her2.neu | 793 | 164 | | 215 | 433 | 4326 |
| 9019.0081 | RGRLGSQDLLNWCMQ | Her2/neu.214 | Her2.neu | 214 | 1039 | | 1412 | | |
| 9019.0082 | LLNWCMQIAKGMSYL | Her2/neu.822 | Her2.neu | 822 | 944 | | 558 | 195 | 1094 |
| 9019.0083 | CMQLAKGMSYLEDVR | Her2/neu.826 | Her2.neu | 826 | 959 | | 2651 | 867 | 1040 |
| 9019.0002 | GMSYLEDVRLVHRDL | Her2/neu.832 | Her2.neu | 832 | 123 | 27 | 957 | 1357 | 4315 |
| 9019.0084 | VRLVHRDLAARNVLV | Her2/neu.839 | Her2.neu | 839 | 59 | 1503 | 105 | 245 | 561 |
| 9019.0085 | HRDLAARNVLVKSPN | Her2/neu.843 | Her2.neu | 843 | 158 | | 401 | 765 | 11.210 |
| 9019.0086 | ARNVLVKSPNGVKIT | Her2/neu.848 | Her2.neu | 848 | 65 | 1275 | 209 | 197 | 10.536 |
| 9019.0087 | PIKWMALESILRRRF | Her2/neu.885 | Her2.neu | 885 | 12 | 30 | 14 | 250 | 161 |
| 9019.0003 | IKWMALESILRRRFT | Her2/neu.886 | Her2.neu | 886 | 16 | 10 | 37 | 1075 | 435 |
| 9019.0088 | ESILRRRFTHQSDVW | Her2/neu.892 | Her2.neu | 892 | 168 | | 794 | 7977 | 2375 |
| 9019.0089 | SDVWSYGVTVWELMT | Her2/neu.903 | Her2.neu | 903 | 165 | | 2760 | 3621 | 1900 |
| 9019.0090 | GVTVWELMTFGAKPY | Her2/neu.909 | Her2.neu | 909 | 40 | | 377 | 4.1 | 2107 |
| 9019.0091 | VWELMTFGAKPYDCI | Her2/neu.912 | Her2.neu | 912 | 36 | | 676 | 144 | 4704 |
| 9019.0092 | AKPYDGIPAREIPDL | Her2/neu.920 | Her2.neu | 920 | 116 | | — | — | 12.548 |

TABLE I-continued

HLA-DR binding affinity of Breast/Ovarian-derived peptides

| | | | | | | | | | | |
|---|---|---|---|---|---|---|---|---|---|---|
| 1622.04 | ICTIDVYMIMVKCWM | Her2/neu.946 | Her2/neu | 946 | — | | 717 | — | 955 | |
| 9019.0094 | DVYMIMVKCWMIDSE | Her2/neu.950 | Her2/neu | 950 | 1312 | | 180 | 7807 | 274 | |
| 9019.0095 | RPRFRELVSEFSRMA | Her2/neu.966 | Her2/neu | 966 | 26 | 6218 | 38 | 62 | 151 | |
| 9019.0096 | FRELVSEFSRMARDP | Her2/neu.969 | Her2/neu | 969 | 20 | 150 | 22 | 51 | 1497 | |
| 9019.0004 | FSRMARDPQRFVVIQ | Her2/neu.976 | Her2/neu | 976 | 29 | 35 | 512 | 2224 | 555 | |
| 9019.0097 | DGDLGMGAAKGLQIL | Her2/neu.1087 | Her2/neu | 1087 | 110 | | 254 | 506 | 5799 | |
| 9019.0098 | AKGLQSLPTHDPSPL | Her2/neu.1095 | Her2/neu | 1095 | 149 | | 194 | 19 | 3864 | |
| 9019.0099 | LQRYSEDPTVPLPSE | Her2/neu.1109 | Her2/neu | 1109 | 1367 | 18 | 25 | 13.089 | 226 | |
| 9019.0100 | PEYVNQPDVRPQPPS | Her2/neu.1137 | Her2/neu | 1137 | 6165 | | 150 | | | |
| 9019.0101 | EGPLPAARPAGETLE | Her2/neu.1154 | Her2/neu | 1154 | 17.288 | | — | | | |
| 9019.0102 | GATLERPKTLSPGKN | Her2/neu.1164 | Her2/neu | 1164 | 1812 | | 2792 | | | |
| 9019.0103 | KDVFAFGGAVENPEY | Her2/neu.1182 | Her2/neu | 1182 | 1505 | | — | | | |
| 9019.0173 | LPRVGCPALPLPPPP | IGFBP2.2 | IGFBP2 | 2 | 1906 | | 6543 | | | |
| 9019.0174 | ALPLPPPPLLPLLPL | IGFBP2.9 | IGFBP2 | 9 | 174 | | 18 | 4.2 | 20 | |
| 9019.0175 | PPPLLPLLPLLLLLL | IGFBP2.14 | IGFBP2 | 14 | 15 | 5816 | 15 | 16 | 65 | |
| 9019.0176 | LLPLLPLLLLLLGAS | IGFBP2.17 | IGFBP2 | 17 | 119 | — | 337 | 35 | 674 | |
| 9019.0177 | PLLLLLLGASGGGGG | IGFBP2.22 | IGFBP2 | 22 | 20 | 18.033 | 339 | 2144 | 1422 | |
| 9019.0178 | AEVLPRCPPCTPERL | IGFBP2.39 | IGFBP2 | 39 | 1285 | | 1611 | | | |
| 9019.0179 | PERLAACGPPPVAPP | IGFBP2.50 | IGFBP2 | 50 | 28 | | 5545 | 163 | 4353 | |
| 9019.0180 | PPPVAPPAAVAAVAG | IGFBP2.58 | IGFBP2 | 58 | 178 | — | 380 | 81 | | |
| 9019.0181 | GARMPCAELVREPGC | IGFBP2.73 | IGFBP2 | 73 | 164 | | 11.638 | 13.072 | — | |
| 9019.0015 | CAELVREPGCGCCSV | IGFBP2.78 | IGFBP2 | 78 | | 12.298 | | | | |
| 9019.0016 | CARLEGEACGVYTPR | IGFBP2.93 | IGFBP2 | 93 | | — | | | | |
| 9019.0182 | ELPLQALVMGEGTCE | IGFBP2.121 | IGFBP2 | 121 | 1502 | | 6782 | | | |
| 9019.0017 | QALVMGEGTCEKRRD | IGFBP2.125 | IGFBP2 | 125 | | 2240 | | | | |
| 9019.0183 | SEGGLVENHVDSTMN | IGFBP2.157 | IGFBP2 | 157 | 1153 | | 1196 | | | |
| 9019.0184 | TMNMLGGGGSAGRKP | IGFBP2.169 | IGFBP2 | 169 | 1021 | | 791 | | | |
| 9019.0185 | LKSGMKELAVFREKV | IGFBP2.154 | IGFBP2 | 154 | 607 | — | 881 | 862 | 34 | |
| 9019.0186 | KELAVFREKVTEQHR | IGFBP2.189 | IGFBP2 | 189 | 2045 | | 21 | | | |
| 9019.0018 | ELAVFREKVIEQHRQ | IGFBP2.190 | IGFBP2 | 190 | | 8621 | | | | |
| 9019.0019 | REKVTEQHRQMGKGG | IGFBP2.195 | IGFBP2 | 195 | | 2839 | | | | |
| 9019.0187 | GKHHLGLEEPKKLRP | IGFBP2.209 | IGFBP2 | 209 | 218 | | 1654 | 2756 | 6494 | |
| 9019.0020 | KHHLGLEEPKKLRPP | IGFBP2.210 | IGFBP2 | 210 | | 4016 | | | | |
| 9019.0188 | EPKKLRPPPARTPCQ | IGFBP2.217 | IGFBP2 | 217 | 1258 | | 806 | | | |
| 9019.0189 | LDQVLERISTMRLPD | IGFBP2.234 | IGFBP2 | 234 | 795 | 452 | 25 | 20 | 18 | |
| 9019.0021 | IMRLPDERGPLEHLY | IGFBP2.243 | IGFBP2 | 243 | | — | | | | |
| 9019.0190 | ERGPLEHLYSLHIPN | IGFBP2.249 | IGFBP2 | 249 | 7.7 | — | 497 | 29 | 110 | |
| 9019.0191 | GLYNLKQCKMSLNGQ | IGFBP2.269 | IGFBP2 | 269 | 923 | — | 743 | 2835 | 5589 | |
| 9019.0192 | TGKLIQGAPTIRGDP | IGFBP2.293 | IGFBP2 | 293 | 148 | 9554 | 40 | 27 | 608 | |
| 9019.0022 | APTIRGDPECHLFYN | IGFBP2.300 | IGFBP2 | 300 | 4031 | 31 | 1643 | 2908 | — | |
| 9019.0023 | CHLFYNLQQEARGVH | IGFBP2.309 | IGFBP2 | 309 | 2490 | 162 | 1600 | 3187 | — | |

| | IC$_{50}$ μM to purified HLA | | | | | | | | | |
|---|---|---|---|---|---|---|---|---|---|---|
| Peptide | DRB1 *0701 | DRB1 *0802 | DRB1 *0901 | DRB1 *1101 | DRB1 *1201 | DRB1 *1302 | DRB1 *1501 | DRB3 *0101 | DRB4 *0101 | DRB5 *0101 |
| 9019.0104 | 107 | 263 | 4132 | 191 | 1558 | 2326 | 61 | — | 339 | 4014 |
| 9019.0105 | 3.7 | 174 | 5779 | 52 | 4995 | 245 | 46 | — | 2171 | 31 |
| 9019.0106 | 70 | 1736 | 4019 | 5977 | 2907 | 35 | 140 | — | 53 | 3350 |
| 9019.0107 | 5.4 | 59 | 989 | 40 | 5.4 | 0.36 | 4.7 | 334 | 50 | 1088 |
| 9019.0108 | 866 | 8432 | — | 1840 | — | 533 | 306 | 3002 | 453 | 1043 |
| 9019.0109 | 46 | 46 | 345 | 36 | 4351 | 990 | 2.6 | — | 5.2 | 2230 |
| 9019.0110 | 1705 | | | 5877 | | 43 | 836 | | 6.3 | 10.223 |
| 9019.0111 | 5252 | | | | | 154 | | | | |
| 9019.0112 | 29 | 1959 | 1355 | 2209 | 212 | 24 | 49 | 4035 | 43 | 10.612 |
| 9019.0113 | 23 | 90 | 83 | 174 | 174 | 1072 | 65 | 14.943 | 18 | 564 |
| 9019.0114 | 56 | 514 | 718 | 6385 | 616 | 1340 | 14 | 14.343 | 22 | 4501 |
| 9019.0115 | 3893 | — | — | 18.399 | — | 394 | 376 | — | 111 | — |
| 9019.0005 | 6338 | | | | | 9963 | | | | |
| 9019.0116 | 7976 | | | | | 786 | | | | |
| 9019.0117 | 407 | | | — | | 23 | 97 | | 5977 | — |
| 9019.0118 | 17 | 119 | 1912 | 22 | 1511 | 22 | 116 | 248 | 555 | 928 |
| 9019.0119 | 5236 | | | 9210 | | 83 | 351 | | 612 | — |
| 9019.0120 | 410 | | | — | | 218 | 583 | | 10.798 | |
| 9019.0121 | 10.607 | | | 3943 | | 125 | 1706 | | 1047 | 51 |
| 9019.0122 | 216 | | | 230 | | 14,768 | — | | 11.448 | 2661 |
| 9019.0123 | 1658 | 293 | 1086 | 358 | 1299 | 26 | 740 | — | 3880 | 3869 |
| 9019.0124 | 649 | | | — | | 2977 | 83 | | 6287 | 14.732 |
| 9019.0125 | 8230 | | | — | | 2322 | 62 | | — | 9255 |
| 9019.0126 | 28 | 243 | 299 | 33 | 1121 | 1921 | 227 | 1088 | 861 | 2284 |
| 9019.0127 | 2248 | | | 5432 | | 161 | 5699 | | 9262 | — |
| 9019.0128 | 5.4 | 21 | 1372 | 776 | 371 | 7.2 | 46 | 2626 | 1784 | 135 |
| 9019.0129 | 9827 | | | | | 1312 | | | | |
| 9019.0130 | 8139 | | | 7338 | | 1024 | 14,891 | | 100 | 4717 |
| 9019.0131 | 4.2 | 3763 | 367 | 6988 | 2758 | 962 | 29 | — | 1263 | 1917 |
| 9019.0132 | 29 | — | 6871 | — | — | 1076 | 1672 | | 10.349 | 3856 |
| 9019.0133 | 121 | | | — | | 4.1 | 138 | | — | — |

TABLE I-continued

HLA-DR binding affinity of Breast/Ovarian-derived peptides

| | | | | | | | | | | |
|---|---|---|---|---|---|---|---|---|---|---|
| 9019.0134 | 12 | | | 3195 | | 314 | 182 | | 4295 | 1348 |
| 9019.0135 | 1095 | | | — | | 921 | 8979 | | 1051 | 36 |
| 9019.0136 | 274 | | | — | | 2.7 | 6657 | | 2105 | 5816 |
| 9019.0137 | 465 | | | — | | 37 | 13.028 | | 42 | 14.095 |
| 9019.0138 | 11.900 | | | 151 | | 70 | 2074 | | 2286 | 1121 |
| 9019.0139 | 31 | | | | | 256 | 8287 | | 2700 | — |
| 9019.0140 | 20 | 70 | 377 | 2174 | 2052 | 30 | 2351 | 6963 | 3247 | 37 |
| 9019.0141 | 531 | 1774 | 4520 | 217 | 2399 | 107 | 1237 | — | 1569 | 17 |
| 9019.0142 | 34 | 184 | 469 | 209 | 1328 | 4.4 | 274 | 15.808 | 26 | 2280 |
| 9019.0143 | 1559 | | | 3319 | | 592 | 3110 | | 174 | 15.069 |
| 9019.0144 | 92 | | | — | | 80 | 3929 | | 2591 | — |
| 1622.05 | 4454 | | | — | | 5637 | 7770 | | 12.094 | 384 |
| 9019.0006 | 11.553 | 16.297 | 5607 | 3471 | 5585 | 349 | 325 | — | 60 | 2016 |
| 9019.0146 | — | | | | | 286 | | | | |
| 9019.0147 | 12.160 | | | | | 319 | | | | |
| 9019.0148 | 7793 | — | 5017 | 9145 | — | 16.129 | 15.733 | — | 313 | 1341 |
| 9019.0149 | 10.056 | | | | | 3587 | | | | |
| 9019.0012 | 481 | 1155 | 1088 | 58 | 1121 | 700 | 338 | — | 108 | 2019 |
| 9019.0150 | 4.6 | 1182 | 137 | 886 | 145 | 8.5 | 7.1 | 8449 | 50 | 47 |
| 9019.0151 | 249 | | | — | | 356 | 87 | | 281 | 17.021 |
| 9019.0011 | | | | | | | | | | |
| 9019.0152 | 1597 | | | 3414 | | 26 | 77 | | 72 | 4444 |
| 9019.0153 | 3332 | 259 | 19.713 | 27 | 79 | 5.4 | 59 | 239 | 2.6 | 2005 |
| 9019.0007 | 1057 | 37 | 18.378 | 46 | 4128 | — | 194 | — | 359 | 3.0 |
| 9019.0154 | 1834 | | | 51 | | 235 | 1075 | | 227 | 2.6 |
| 9019.0155 | 2152 | | | 1248 | | 221 | 208 | | 102 | 731 |
| 9019.0156 | 468 | 3144 | — | 831 | 513 | 227 | 277 | — | 421 | 504 |
| 9019.0157 | 17 | | | 61 | | 1031 | 1113 | | 2423 | 36 |
| 9019.0158 | 220 | | | 321 | | 530 | 1294 | | 2461 | 2364 |
| 1622.01 | — | — | — | — | — | — | 5360 | — | 738 | 253 |
| 9019.0159 | 1105 | 16.263 | 15.928 | — | — | 879 | 25 | — | 33 | 4620 |
| 9019.0009 | 6648 | | | — | | 3494 | 4757 | | 87 | 18.258 |
| 9019.0160 | 3440 | | | | | 939 | | | | |
| 9019.0161 | 401 | | | 1094 | | 44 | 1449 | | 11 | 2802 |
| 9019.0010 | | | | | | | | | | |
| 1622.06 | 2196 | 761 | 6097 | 187 | 1325 | 41 | 28 | — | 321 | 39 |
| 9019.0163 | 1797 | 360 | 3090 | 48 | 102 | 4.9 | 246 | — | 39 | 19 |
| 9019.0164 | 382 | 702 | 449 | 1043 | 110 | 3.0 | 356 | 5897 | 1839 | 2519 |
| 9019.0165 | 1101 | 18.625 | 4876 | 11.907 | 194 | 332 | 356 | — | 576 | 41 |
| 9019.0013 | | | | | | | | | | |
| 9019.0166 | 1160 | | | | | 820 | | | | |
| 9019.0167 | 4.4 | 195 | 236 | 34 | 3.9 | 2.0 | 3.3 | 342 | 8.7 | 23 |
| 9019.0168 | 1.3 | 445 | 526 | 276 | 132 | 219 | 97 | — | 46 | 18 |
| 9019.0169 | 324 | 319 | 752 | 88 | 21 | 24 | 84 | 5290 | 290 | 826 |
| 9019.0170 | 133 | 1401 | 301 | 466 | 10.090 | 55 | 26 | — | 91 | 957 |
| 9019.0171 | 161 | 10.850 | — | 11.089 | 2018 | 171 | 1205 | — | 296 | 3541 |
| 9019.0172 | — | | | | | 12.776 | | | | |
| 9019.0014 | — | | | 756 | | 4755 | 8176 | | 4028 | — |
| 9019.0024 | 7995 | | | | | 704 | | | | |
| 9019.0025 | 16.366 | | | 12 | | 521 | 21 | | 33 | 337 |
| 1622.02 | 7183 | | | 944 | | 10,697 | 17.445 | | 19.806 | 17 |
| 9019.0027 | 6814 | | | | | 14.523 | | | | |
| 9019.0028 | 4948 | | | | | 5043 | | | | |
| 9019.0029 | 1972 | | | | | 417 | | | | |
| 9019.0030 | 7.2 | 94 | 3055 | 30 | 141 | 105 | 23 | — | 29 | 189 |
| 9019.0031 | 15 | 426 | 4081 | 213 | 150 | 47 | 132 | 141 | 1633 | 173 |
| 9019.0032 | 35 | 213 | 302 | 165 | 3438 | 103 | 75 | 13.508 | 546 | 1361 |
| 9019.0033 | 92 | 300 | 358 | 208 | 302 | 1.9 | 679 | 649 | 124 | 18 |
| 9019.0034 | 80 | 85 | 6044 | 21 | 42 | 270 | 340 | — | 18 | 173 |
| 9019.0035 | 218 | | | | | 2546 | | | | |
| 9019.0001 | 129 | | | 9195 | | 4.0 | 450 | | 6955 | 3744 |
| 9019.0036 | 13.172 | | | | | 1030 | | | | |
| 9019.0037 | 1843 | | | 11.554 | | 605 | 17.148 | | 2519 | 3001 |
| 9019.0038 | 1541 | | | 2207 | | 786 | 4405 | | 2214 | 16.273 |
| 9019.0039 | 2486 | | | 692 | | 343 | 1183 | | 511 | 1878 |
| 9019.0040 | 14.279 | | | 1720 | | 34 | 106 | | 351 | 13.612 |
| 9019.0041 | — | | | | | 5074 | | | | |
| 9019.0042 | 1324 | | | 521 | | 3216 | 748 | | 441 | 2809 |
| 9019.0043 | 2139 | | | | | 6781 | | | | |
| 9019.0044 | 271 | — | — | 3064 | 18.979 | 25 | 690 | — | 444 | 3776 |
| 9019.0045 | 9.7 | 95 | 4345 | 262 | 221 | 23 | 86 | — | 81 | 216 |
| 9019.0046 | 12 | 456 | 5187 | 661 | 161 | 1.5 | 27 | — | 163 | 94 |
| 9019.0047 | 45 | | | 3080 | | 206 | 635 | | 316 | 4567 |
| 9019.0048 | 2823 | | | 12.591 | | 3905 | 805 | | 654 | — |
| 9019.0049 | 6994 | | | | | 2322 | | | | |
| 9019.0050 | 136 | | | 2573 | | 751 | 152 | | 270 | 67 |
| 9019.0051 | — | | | | | — | | | | |
| 9019.0052 | 7.1 | 146 | 859 | 9.6 | 486 | 80 | 33 | — | 67 | 17 |

TABLE I-continued

HLA-DR binding affinity of Breast/Ovarian-derived peptides

| | | | | | | | | | | |
|---|---|---|---|---|---|---|---|---|---|---|
| 9019.0053 | 12 | 119 | 4217 | 173 | 47 | 9.9 | 3.3 | 4320 | 446 | 28 |
| 9019.0054 | 5.6 | 5077 | 430 | 773 | 40 | 1.3 | 5.4 | 358 | 562 | 82 |
| 9019.0055 | 3096 | | | 6307 | | 1597 | 50 | | 22 | — |
| 9019.0056 | 55 | 1538 | 1140 | 2268 | 436 | 3030 | 5.2 | — | 154 | 2048 |
| 9019.0057 | 142 | 1075 | 594 | 309 | 498 | 16 | 24 | 16.142 | 549 | 726 |
| 9019.0058 | 277 | | | 2822 | | 18 | 164 | | 357 | 6081 |
| 9019.0059 | 178 | | | 793 | | 175 | 1431 | | 117 | 7390 |
| 9019.0060 | 2097 | | | 4976 | | 323 | 6267 | | 1117 | 12.277 |
| 9019.0061 | 6742 | | | | | 2912 | | | | |
| 9019.0062 | 540 | | | 16.162 | | 146 | 285 | | 1523 | 7043 |
| 9019.0063 | 1861 | | | 254 | | 548 | 635 | | 2072 | 211 |
| 9019.0064 | 1903 | | | 405 | | 670 | 423 | | 2551 | 49 |
| 9019.0065 | 2618 | | | | | 1531 | | | | |
| 9019.0066 | 24 | 3089 | 118 | 511 | 1431 | 14 | 59 | 18,926 | 1500 | 206 |
| 9019.0067 | 941 | | | 5188 | | 443 | 6005 | | 3109 | — |
| 9019.0068 | 780 | | | 2464 | | 478 | 7117 | | 11.015 | — |
| 9019.0969 | 17 | 35 | — | 12 | 268 | 17 | 185 | — | 958 | 38 |
| 9019.0070 | 44 | | | 40 | | 44 | 2.0 | | 93 | 300 |
| 9019.0071 | 722 | | | 46 | | 2583 | 1.6 | | 303 | 2207 |
| 9019.0072 | 170 | | | 2103 | | 1318 | 329 | | 368 | 1223 |
| 9019.0073 | 101 | 139 | 5423 | 176 | 2472 | 980 | 205 | — | 452 | 1020 |
| 9019.0074 | 77 | | | 1711 | | 1308 | 244 | | 1380 | 1369 |
| 9019.0075 | 180 | | | 4535 | | 1149 | 729 | | 34 | 8353 |
| 1622.03 | — | | | 4108 | | 501 | 611 | | 7805 | 1505 |
| 9019.0077 | 45 | | | 1738 | | 402 | 24 | | 5060 | 308 |
| 9019.0078 | 352 | | | | | 1508 | | | | |
| 9019.0079 | 9.0 | 634 | 137 | 80 | 446 | 4.7 | 39 | 3567 | 481 | 392 |
| 9019.0080 | 1288 | | | 11.126 | | 3594 | 9.4 | | 16 | 3002 |
| 9019.0081 | 2029 | | | | | 3367 | | | | |
| 9019.0082 | 380 | | | 159 | | 2082 | 799 | | 3359 | 92 |
| 9019.0083 | 116 | | | 405 | | 2232 | 1002 | | 3005 | 130 |
| 9019.0002 | 5408 | | | 244 | | 3789 | 567 | | 2543 | 467 |
| 9019.0084 | 356 | | | 16 | | 57 | 1097 | | 298 | 2425 |
| 9019.0085 | 1332 | | | 1618 | | 116 | 221 | | 525 | 302 |
| 9019.0086 | 118 | 717 | 4771 | 513 | 628 | 15 | 29 | 16.142 | 742 | 4.9 |
| 9019.0087 | 664 | 312 | 3620 | 133 | 66 | 349 | 3.3 | — | 62 | 3.4 |
| 9019.0003 | 1795 | 515 | 9282 | 136 | 241 | 1118 | 11 | — | 340 | 3.3 |
| 9019.0088 | 9598 | | | 1159 | | 16.279 | 2726 | | 818 | 5305 |
| 9019.0089 | 546 | | | 2639 | | 467 | 1879 | | — | 5423 |
| 9019.0090 | 558 | | | 315 | | 8868 | 20 | | 1171 | 34 |
| 9019.0091 | 191 | | | 1952 | | 7553 | 245 | | 3565 | 65 |
| 9019.0092 | 41 | | | — | | 19.575 | 6957 | | — | 3044 |
| 1622.04 | — | | | 1480 | | — | 2652 | | — | — |
| 9019.0094 | 297 | | | 179 | | 395 | 1303 | | 697 | 716 |
| 9019.0095 | 309 | 376 | 2321 | 125 | 1779 | 12.182 | 348 | — | 351 | 26 |
| 9019.0096 | 5055 | 1714 | — | 381 | — | — | 124 | 4537 | 1262 | 380 |
| 9019.0004 | 1422 | 798 | 1401 | 49 | 6867 | 240 | 1408 | 901 | 227 | 45 |
| 9019.0097 | 828 | | | 2233 | | 3224 | 1684 | | 896 | 2141 |
| 9019.0098 | 4459 | | | 6806 | | 3991 | 1665 | | 572 | — |
| 9019.0099 | 107 | | | 94 | | 280 | 5310 | | | |
| 9019.0100 | — | | | | | 1714 | | | | |
| 9019.0101 | 7463 | | | | | 10.247 | | | | |
| 9019.0102 | | | | | | 5332 | | | | |
| 9019.0103 | 1577 | | | | | 16.146 | | | | |
| 9019.0173 | — | | | | | 8936 | | | | |
| 9019.0174 | 336 | 1067 | | 41 | 1337 | 1524 | 262 | — | 40 | 9665 |
| 9019.0175 | 13 | 86 | 307 | 121 | 23 | 1322 | 5.0 | 16.239 | 2.1 | 121 |
| 9019.0176 | 964 | 213 | 5893 | 478 | 320 | 2922 | 182 | — | 19 | 2390 |
| 9019.0177 | 5882 | 5696 | — | 12.818 | 18.255 | 2164 | 253 | — | 316 | — |
| 9019.0178 | 15.970 | | | | | 5774 | | | | |
| 9019.0179 | — | | | 3541 | | 3618 | 4054 | | 4455 | 19.685 |
| 9019.0180 | 2684 | — | 317 | — | — | 237 | 1378 | — | 1888 | — |
| 9019.0181 | — | | | 2968 | | 16.279 | — | | 4697 | — |
| 9019.0015 | | | | | | | | | | |
| 9019.0016 | | | | | | | | | | |
| 9019.0182 | 15.638 | | | | | 9167 | | | | |
| 9019.0017 | | | | | | | | | | |
| 9019.0183 | 4623 | | | | | 2518 | | | | |
| 9019.0184 | 6177 | | | | | 5686 | | | | |
| 9019.0185 | — | 260 | — | 163 | 1768 | 4974 | 91 | — | 417 | 843 |
| 9019.0186 | — | | | | | — | | | | |
| 9019.0018 | | | | | | | | | | |
| 9019.0019 | | | | | | | | | | |
| 9019.0187 | 3697 | | | 16.749 | | 3029 | 3345 | | 1378 | 6390 |
| 9019.0020 | | | | | | | | | | |
| 9019.0188 | 1122 | | | | | 1213 | | | | |
| 9019.0189 | 5.2 | 1607 | 52 | 467 | 324 | 1052 | 84 | — | 367 | 223 |
| 9019.0021 | | | | | | | | | | |

TABLE I-continued

HLA-DR binding affinity of Breast/Ovarian-derived peptides

| | | | | | | | | | | |
|---|---|---|---|---|---|---|---|---|---|---|
| 9019.0190 | 18 | 9361 | 638 | 1993 | 50 | 1149 | 23 | — | 1618 | 4000 |
| 9019.0191 | 1791 | 204 | 9434 | 2600 | 413 | 561 | 223 | — | 1613 | 5609 |
| 9019.0192 | 883 | 5160 | 700 | 7989 | 2691 | 927 | 1733 | 2191 | 465 | 36 |
| 9019.0022 | 16.779 | — | — | — | 16.917 | 1674 | 3669 | 191 | 2510 | — |
| 9019.0023 | — | — | — | — | 1855 | 146 | — | 18.902 | 5310 | — |

— indicates binding affinity ≥20.000 nM.

TABLE II

Breast/Ovarian HLA-DR Supertype Candidates

| | | | | | IC$_{50}$ nM to purified HLA | | | | | |
|---|---|---|---|---|---|---|---|---|---|---|
| Peptide No. | Sequence | Source | Protein | Position | DRB1 *0101 | DRB1 *0301 | DRB1 *0401 | DRB1 *0404 | DRB1 *0405 | DRB1 *0701 |
| 9019.0105 | LLTFWNPPTTAKLTI | CEA.24 | CEA | 24 | 6.9 | 16.313 | 273 | 52 | 258 | 3.7 |
| 9019.0106 | TAKLTIESTPFNVAE | CEA.33 | CEA | 33 | 72 | 613 | 106 | 41 | 383 | 70 |
| 9019.0107 | EVLLLVHNLPQHLFG | CEA.50 | CEA | 50 | 2.7 | 830 | 3.4 | 1.7 | 30 | 5.4 |
| 9019.0108 | YSWYKGERVDGNRQI | CEA.65 | CEA | 65 | 511 | — | 34 | 585 | 360 | 866 |
| 9019.0109 | NRQIIGYVIGTQQAT | CEA.76 | CEA | 76 | 216 | — | 108 | 1.5 | 129 | 46 |
| 9019.0112 | GREIIYPNASLLIQN | CEA.97 | CEA | 97 | 62 | 433 | 251 | 88 | 550 | 29 |
| 9019.0113 | DTGFYTLHVIKSDLV | CEA.116 | CEA | 116 | 64 | 984 | 84 | 260 | 95 | 23 |
| 9019.0114 | FYTLHVIKSDLVNEE | CEA.119 | CEA | 119 | 101 | 80 | 184 | 169 | 41 | 56 |
| 9019.0118 | YLWWVNNQSLPVSPR | CEA.176 | CEA | 176 | 2.1 | 100 | 432 | 203 | 80 | 17 |
| 9019.0123 | QELFIPNITVNNSGS | CEA.282 | CEA | 282 | 147 | 644 | 25 | 227 | 379 | 1658 |
| 9019.0126 | YLWWVNNQSLPVSPR | CEA.354 | CEA | 354 | 1123 | 234 | 12 | 248 | 88 | 28 |
| 9019.0128 | SYTYYRPGVNLSLSC | CEA.423 | CEA | 423 | 1.6 | 4425 | 6.8 | 4036 | 300 | 5.4 |
| 9019.0131 | RTTVKTTTVSAELPK | CEA.488 | CEA | 488 | 89 | — | 58 | 54 | 11 | 4.2 |
| 9019.0140 | NGTYACFVSNLATGR | CEA.650 | CEA | 650 | 839 | 818 | 11 | 558 | 30 | 20 |
| 9019.0141 | YACFVSNLATGRNNS | CEA.653 | CEA | 653 | 183 | 774 | 225 | 41 | 327 | 531 |
| 9019.0142 | NNSIVKSITVSASGT | CEA.665 | CEA | 665 | 34 | 103 | 43 | 1.8 | 128 | 34 |
| 9019.0006 | HQLLCCEVETIRRAY | Cyclin D1.3 | Cyclin D1 | 3 | 953 | 21 | 746 | 256 | 4200 | 11.553 |
| 9019.0012 | QKEVLPSMRKIVATW | Cyclin D1.49 | Cyclin D1 | 49 | 9825 | 111 | 12.162 | 1102 | 3720 | 481 |
| 9019.0150 | LPSMRKIVATWMLEV | Cyclin D1.53 | Cyclin D1 | 53 | 8.5 | 826 | 238 | 28 | 123 | 4.6 |
| 9019.0153 | VFPLAMXNYLDRFLSL | Cyclin D1.77 | Cyclin D1 | 77 | 146 | 107 | 2352 | 1567 | 609 | 3332 |
| 9019.0007 | DRFLSLEPVKKSRLQ | Cyclin D1.86 | Cyclin D1 | 86 | 16 | 290 | 18 | 61 | 159 | 1057 |
| 9019.0156 | RLQLLLGATCMFVASK | Cyclin D1.98 | Cyclin D1 | 98 | 12 | — | 91 | 633 | 1439 | 468 |
| 1622.06 | LLQMELLLVNKLSWN | Cyclin D1.117 | Cyclin D1 | 137 | 39 | — | 3539 | 6.4 | 332 | 2196 |
| 9019.0163 | MELLLVNKLKWNLAA | Cyclin D1.140 | Cyclin D1 | 140 | 46 | 9006 | 177 | 491 | 2411 | 1979 |
| 9019.0164 | VNKLKWNLAAMTPHD | Cyclin D1.145 | Cyclin D1 | 145 | 46 | 1419 | 88 | 781 | 747 | 382 |
| 9019.0165 | KWNLAAMTPHDFIEH | Cyclin D1.149 | Cyclin D1 | 149 | 33 | 6249 | 3405 | 653 | 122 | 1101 |
| 9019.0167 | NKQIIKHAQTFVAL | Cyclin D1.174 | Cyclin D1 | 174 | 4.7 | 561 | 6.5 | 23 | 25 | 4.4 |
| 9019.0168 | AQTFVALCATDVKFI | Cyclin D1.182 | Cyclin D1 | 182 | 8.4 | 551 | 26 | 133 | 55 | 13 |
| 9019.0169 | VKFISNPPSMVAAGS | Cyclin D1.193 | Cyclin D1 | 193 | 6.7 | 4128 | 12 | 18 | 117 | 304 |
| 9019.0170 | PPSMVAAGSVVAAVQ | Cyclin D1.199 | Cyclin D1 | 199 | 6.8 | — | 12 | 26 | 1718 | 133 |
| 9019.0171 | VAAVQGLNLRSPNNF | Cyclin D1.209 | Cyclin D1 | 209 | 44 | 18.558 | 226 | 532 | 4248 | 161 |
| 9019.0030 | NLELTYLPTNASLSF | Her2/neu.59 | Her2/neu | 59 | 4.9 | 7356 | 6.2 | 2.7 | 38 | 7.2 |
| 9019.0031 | LTYLPTNASLSFLQD | Her2/neu.62 | Her2/neu | 62 | 9.3 | 3364 | 19 | 16 | 80 | 15 |
| 9019.0032 | YQEVQGYVLIAHNQV | Her2/neu.77 | Her2/neu | 77 | 57 | 7763 | 111 | 178 | 102 | 35 |
| 9019.0033 | TVLIAHNQVRQVPLQ | Her2/neu.83 | Her2/neu | 83 | 28 | 454 | 53 | 104 | 1185 | 92 |
| 9019.0034 | HNQVRQVPLQRLRIV | Her2/neu.88 | Her2/neu | 88 | 950 | 971 | 840 | 78 | 1303 | 80 |
| 9019.0045 | MEHLREVRAVTSANI | Her2/neu.347 | Her2/neu | 347 | 9.6 | 2970 | 533 | 12 | 200 | 9.7 |
| 9019.0046 | LREVRAVTSANIQEF | Her2/neu.350 | Her2/neu | 350 | 17 | 3913 | 43 | 8.2 | 50 | 12 |
| 9019.0052 | LSVFQNLQVIRGRIL | Her2/neu.422 | Her2/neu | 422 | 1.3 | 345 | 6.3 | 33 | 26 | 7.1 |
| 9019.0054 | RGRILHNGAYSLTLQ | Her2/neu.432 | Her2/neu | 432 | 2.4 | 710 | 480 | 129 | 2845 | 5.6 |
| 9019.0057 | LRSLRELGSGLALIH | Her2/neu.455 | Her2/neu | 455 | 7.1 | — | 896 | 14 | 603 | 142 |
| 9019.0069 | VLGVVFGILIKRRQQ | Her2/neu.666 | Her2/neu | 666 | 67 | 2449 | 177 | 335 | 101 | 17 |
| 9019.0079 | SRLLGICLTSTVQLV | Her2/neu.783 | Her2/neu | 783 | 80 | 2923 | 85 | 13 | 90 | 9.0 |
| 9019.0087 | PIKWMALESILRRRF | Her2/neu.885 | Her2/neu | 885 | 12 | 30 | 14 | 250 | 161 | 664 |
| 9019.0003 | IKWMALESILRRRFT | Her2/neu.886 | Her2/neu | 886 | 16 | 10 | 37 | 1075 | 435 | 1795 |
| 9019.0004 | FRSMARDPQRFVVPQ | Her2/neu.976 | Her2/neu | 976 | 29 | 35 | 512 | 2224 | 855 | 1423 |
| 9019.0174 | ALPLPPPPLLPLLPL | IGFBP2.9 | IGFBP2 | 9 | 174 | — | 18 | 4.2 | 20 | 336 |
| 9019.0175 | PPPLLPLLPLLLLLL | IGFBP2.14 | IGFBP2 | 14 | 15 | 5816 | 15 | 16 | 65 | 13 |
| 9019.0176 | LLPLLPLLLLLLGAS | IGFBP2.17 | IGFBP2 | 17 | 119 | — | 337 | 35 | 674 | 964 |
| 9019.0177 | PLLLLLLGASGGGGG | IGFBP2.22 | IGFBP2 | 22 | 20 | 18.033 | 339 | 2144 | 1422 | 5882 |
| 9019.0180 | PPPVAPPAAVAAVAG | IGFBP2.58 | IGFBP2 | 58 | 178 | — | 380 | 81 | — | 2684 |
| 9019.0185 | LKSGMKELAVFREKV | IGFBP2.184 | IGFBP2 | 184 | 607 | — | 881 | 862 | 34 | — |
| 9019.0189 | LDQVLERISTMRLPD | IGFBP2.234 | IGFBP2 | 234 | 795 | 452 | 25 | 20 | 18 | 5.2 |
| 9019.0190 | ERGPLEHLYSLHIPN | IGFBP2.249 | IGFBP2 | 249 | 7.7 | — | 497 | 29 | 110 | 18 |

TABLE II-continued

Breast/Ovarian HLA-DR Supertype Candidates

| | | | | | | | | | | |
|---|---|---|---|---|---|---|---|---|---|---|
| 9019.0191 | GLYNLKQCKMSLNGQ | IGFBP2.268 | IGFBP2 | 268 | 923 | — | 743 | 2835 | 5589 | 1791 |
| 9019.0192 | TGKLIQGAPTIRGDP | IGFBP2.293 | IGFBP2 | 293 | 148 | 9554 | 40 | 27 | 608 | 883 |

| | IC$_{50}$ nM to purified HLA | | | | | | | | | |
|---|---|---|---|---|---|---|---|---|---|---|
| Peptide No. | DRB1 *0802 | DRB1 *0901 | DRB1 *1101 | DRB1 *1201 | DRB1 *1302 | DRB1 *1501 | DRB3 *0101 | DRB4 *0101 | DRB5 *0101 | Total XRN |
| 9019.0105 | 174 | 5779 | 52 | 4995 | 245 | 45 | — | 2171 | 13 | 10 |
| 9019.0106 | 1736 | 4019 | 5997 | 2907 | 35 | 140 | — | 53 | 3550 | 9 |
| 9019.0107 | 19 | 989 | 40 | 5.4 | 0.36 | 4.7 | 334 | 50 | 1088 | 14 |
| 9019.0108 | 8432 | — | 1840 | — | 533 | 306 | 3002 | 453 | 1043 | 8 |
| 9019.0109 | 46 | 345 | 36 | 4351 | 990 | 2.6 | — | 5.2 | 2230 | 11 |
| 9019.0112 | 1959 | 1355 | 2209 | 212 | 24 | 49 | 4035 | 43 | 10.612 | 10 |
| 9019.0113 | 90 | 83 | 174 | 174 | 1072 | 65 | 14.943 | 18 | 564 | 13 |
| 9019.0114 | 514 | 718 | 6385 | 616 | 1340 | 14 | 14.343 | 22 | 4501 | 11 |
| 9019.0118 | 119 | 1912 | 22 | 1511 | 22 | 116 | 218 | 555 | 923 | 13 |
| 9019.0123 | 293 | 1086 | 358 | 1299 | 26 | 740 | — | 3880 | 3869 | 9 |
| 9019.0126 | 243 | 299 | 33 | 1121 | 1921 | 227 | 1088 | 861 | 2281 | 10 |
| 9019.0128 | 21 | 1372 | 776 | 371 | 7.2 | 46 | 2626 | 1784 | 135 | 10 |
| 9019.0131 | | | 6988.0 | | 962 | 29 | | 1263 | 1917 | 7 |
| 9019.0140 | 70 | 377 | 2174 | 2052 | 30 | 2351 | 6963 | 3247 | 37 | 10 |
| 9019.0141 | 1774 | 4520 | 217 | 2399 | 107 | 1237 | — | 1569 | 17 | 9 |
| 9019.0142 | 184 | 469 | 209 | 1328 | 4.4 | 274 | 15.808 | 26 | 2280 | 12 |
| 9019.0006 | 16.297 | 5607 | 3471 | 5585 | 349 | 325 | — | 60 | 2016 | 7 |
| 9019.0012 | 1155 | 1088 | 58 | 1121 | 700 | 228 | — | 108 | 2019 | 6 |
| 9019.0150 | 1182 | 137 | 886 | 145 | 8.5 | 7.1 | 8449 | 50 | 47 | 13 |
| 9019.0153 | 259 | 19.713 | 27 | 79 | 5.4 | 39 | 219 | 2.6 | 2005 | 10 |
| 9019.0007 | 37 | 18.378 | 46 | 4128 | — | 394 | — | 359 | 3.0 | 10 |
| 9019.0156 | 3144 | — | 831 | 513 | 227 | 277 | | 421 | 564 | 10 |
| 1622.06 | 765 | 6097 | 187 | 1325 | 44 | 28 | — | 321 | 39 | 9 |
| 9019.0163 | 368 | 3090 | 48 | 162 | 4.9 | 246 | — | 39 | 19 | 10 |
| 9019.0164 | 702 | 449 | 1043 | 116 | 3.0 | 356 | 5867 | 1839 | 2519 | 10 |
| 9019.0165 | 18.625 | 4876 | 11.307 | 194 | 332 | 356 | — | 576 | 41 | 8 |
| 9019.0167 | 115 | 235 | 34 | 3.9 | 2.0 | 3.3 | 342 | 8.7 | 23 | 15 |
| 9019.0168 | 445 | 536 | 276 | 132 | 219 | 97 | — | 46 | 18 | 14 |
| 9019.0169 | 319 | 752 | 88 | 21 | 24 | 84 | 5290 | 290 | 826 | 13 |
| 9019.0170 | 1401 | 301 | 466 | 10.090 | 55 | 26 | — | 91 | 957 | 10 |
| 9019.0171 | 10.850 | — | 11.089 | 2018 | 171 | 1205 | — | 296 | 3541 | 6 |
| 9019.0030 | 94 | 3055 | 30 | 141 | 105 | 23 | — | 29 | 189 | 12 |
| 9019.0031 | 426 | 1081 | 213 | 150 | 47 | 132 | 141 | 1633 | 173 | 12 |
| 9019.0032 | 213 | 302 | 165 | 3438 | 103 | 75 | 13.508 | 546 | 1361 | 11 |
| 9019.0033 | 300 | 358 | 208 | 302 | 1.9 | 679 | 649 | 1234 | 18 | 14 |
| 9019.0034 | 85 | 6644 | 21 | 42 | 270 | 340 | — | 18 | 173 | 12 |
| 9019.0045 | 95 | 4345 | 262 | 221 | 23 | 86 | — | 81 | 216 | 12 |
| 9019.0046 | 456 | 5187 | 661 | 161 | 1.5 | 27 | — | 163 | 94 | 12 |
| 9019.0052 | 1484 | 859 | 9.6 | 486 | 80 | 33 | — | 67 | 17 | 14 |
| 9019.0054 | 5077 | 430 | 773 | 40 | 1.3 | 5.4 | 358 | 562 | 82 | 13 |
| 9019.0057 | 1075 | 594 | 309 | 498 | 16 | 24 | 16.142 | 549 | 726 | 12 |
| 9019.0069 | 35 | — | 12 | 268 | 17 | 185 | — | 958 | 38 | 12 |
| 9019.0079 | 634 | 137 | 80 | 446 | 4.7 | 39 | 3567 | 481 | 392 | 13 |
| 9019.0087 | 312 | 3620 | 133 | 66 | 349 | 3.3 | — | 62 | 3.4 | 13 |
| 9019.0003 | 515 | 9282 | 136 | 241 | 1118 | 11 | — | 340 | 3.3 | 10 |
| 9019.0004 | 798 | 1481 | 49 | 6867 | 240 | 1408 | 901 | 227 | 45 | 10 |
| 9019.0174 | 1087 | — | 41 | 1337 | 1524 | 262 | — | 40 | 9665 | 8 |
| 9019.0175 | 86 | 307 | 121 | 23 | 1322 | 5.0 | 16.239 | 2.1 | 121 | 12 |
| 9019.0176 | 213 | 5893 | 458 | 320 | 2022 | 182 | — | 19 | 2390 | 10 |
| 9019.0177 | 5696 | — | 12.818 | 18.255 | 2164 | 253 | — | 316 | — | 4 |
| 9019.0180 | — | 317 | — | — | 237 | 1378 | — | 1888 | — | 5 |
| 9019.0185 | 260 | — | 163 | 1768 | 4974 | 91 | — | 417 | 843 | 9 |
| 9019.0189 | 1607 | 52 | 467 | 314 | 1052 | 84 | — | 367 | 223 | 12 |
| 9019.0190 | 9361 | 631 | 1993 | 50 | 1149 | 23 | — | 1648 | 4000 | 8 |
| 9019.0191 | 204 | 9434 | 2600 | 413 | 561 | 223 | — | 1613 | 5609 | 6 |
| 9019.0192 | 5160 | 700 | 7989 | 2691 | 927 | 1733 | 2191 | 465 | 36 | 9 |

— indicates binding affinity ≥20,000 nM.

TABLE III

Vaccine Candidates

| EPITOPE | % | DRB1 *0101 | DRB1 *0301 | DRB1 *0401 | DRB1 *0404 | DRB1 *0405 | DRB1 *0701 | DRB1 *0802 | DRB1 *0901 |
|---|---|---|---|---|---|---|---|---|---|
| HER2/NEU.59 | 15 | X |  | X | X | X | X | X |  |
| HER2/NEU.885 | 25 | X | X | X | X | X |  | X |  |
| CEA.24 | 17 | X |  | X | X | X | X | X |  |
| CEA.653 | 25 | X |  | X | X | X |  |  |  |
| IGFBP2.17 | 19 | X |  | X | X |  |  | X |  |
| IGFBP2.249 | 23 | X |  | X | X | X | X |  |  |
| CYCLIND1.53 | 13 | X |  | X | X | X | X |  | X |
| CYCLIND1.199 | 13 | X |  | X | X |  | X |  | X |

| EPITOPE | DRB1 *1101 | DRB1 *1201 | DRB1 *1302 | DRB1 *1501 | DRB3 *0101 | DRB4 *0101 | DRB5 *0101 |
|---|---|---|---|---|---|---|---|
| HER2/NEU.59 | X | X | X | X |  | X | X |
| HER2/NEU.885 | X | X |  | X |  | X | X |
| CEA.24 | X |  | X | X |  |  | X |
| CEA.653 | X |  | X |  |  |  | X |
| IGFBP2.17 | X | X |  | X |  | X |  |
| IGFBP2.249 |  | X |  | X |  |  |  |
| CYCLIND1.53 |  | X | X | X |  | X | X |
| CYCLIND1.199 | X |  | X | X |  | X |  |

% = Percent of patients with responses

---

What is claimed is:

1. A method for eliciting an immunogenic response in a mammal, wherein the method comprises administering to the mammal a composition comprising a pharmaceutical excipient and isolated immunogenic HLA-DR binding peptides having the sequences set forth in SEQ ID NOS:86, 90, 109, and 145 such that an immunogenic response occurs in the mammal.

2. The method of claim 1, wherein the mammal is a human.

3. The method of claim 1, wherein the immunogenic response is a helper T-cell response.

4. The method of claim 1, wherein the pharmaceutical excipient is selected from the group consisting of an adjuvant, a carrier, a pH-adjusting agent, a buffering agent, a tonicity adjusting agent, a wetting agent and a preservative.

5. The method of claim 1, wherein the pharmaceutical excipient is an adjuvant.

6. The method of claim 1, wherein the immunogenic HLA-DR binding peptides are lipidated.

7. The method of claim 1, wherein the composition further comprises a liposome.

8. The method of claim 1, wherein the composition further comprises an additional HTL-inducing peptide.

9. The method of claim 1, wherein the composition further comprises a CTL-inducing peptide.

10. The method of claim 1, wherein the composition further comprises at least two Carcinoembryonic Antigen (CEA) HTL peptides, at least two Cyclin D1 HTL peptides, and at least two Insulin Growth Factor Binding Protein 2 (IGFBP-2) HTL peptides.

* * * * *

UNITED STATES PATENT AND TRADEMARK OFFICE
CERTIFICATE OF CORRECTION

| | | |
|---|---|---|
| PATENT NO. | : 10,556,943 B2 | Page 1 of 1 |
| APPLICATION NO. | : 15/381454 | |
| DATED | : February 11, 2020 | |
| INVENTOR(S) | : Keith L. Knutson et al. | |

It is certified that error appears in the above-identified patent and that said Letters Patent is hereby corrected as shown below:

In the Specification

Column 1, Line 12, please delete "Oct. 3," and insert -- Oct. 30, -- therefor.

Signed and Sealed this
Twenty-first Day of July, 2020

Andrei Iancu
*Director of the United States Patent and Trademark Office*

SEQUENCE LISTING

<160> NUMBER OF SEQ ID NOS: 198

<210> SEQ ID NO 1
<211> LENGTH: 14
<212> TYPE: PRT
<213> ORGANISM: Clostridium tetani

<400> SEQUENCE: 1

Gln Tyr Ile Lys Ala Asn Ser Lys Phe Ile Gly Ile Thr Glu
1               5                   10

<210> SEQ ID NO 2
<211> LENGTH: 21
<212> TYPE: PRT
<213> ORGANISM: Plasmodium falciparum

<400> SEQUENCE: 2

Asp Ile Glu Lys Lys Ile Ala Lys Met Glu Lys Ala Ser Ser Val Phe
1               5                   10                  15

Asn Val Val Asn Ser
            20

<210> SEQ ID NO 3
<211> LENGTH: 17
<212> TYPE: PRT
<213> ORGANISM: Streptococcus sp.

<400> SEQUENCE: 3

Tyr Gly Ala Val Asp Ser Ile Leu Gly Gly Val Ala Thr Tyr Gly Ala
1               5                   10                  15

Ala

<210> SEQ ID NO 4
<211> LENGTH: 13
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala or D-Ala
<220> FEATURE:
<221> NAME/KEY: MOD_RES
<222> LOCATION: (3)..(3)
<223> OTHER INFORMATION: cyclohexylalanine, Phe or Tyr
<220> FEATURE:
<221> NAME/KEY: MOD_RES
<222> LOCATION: (13)..(13)
<223> OTHER INFORMATION: Ala or D-Ala

<400> SEQUENCE: 4

Ala Lys Xaa Val Trp Ala Asn Thr Leu Lys Ala Ala Ala
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Trp Cys Ile Pro Trp Gln Arg Leu Leu Leu Thr Ala Ser Leu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Leu Thr Phe Trp Asn Pro Pro Thr Thr Ala Lys Leu Thr Ile
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Ala Lys Leu Thr Ile Glu Ser Thr Pro Phe Asn Val Ala Glu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Val Leu Leu Leu Val His Asn Leu Pro Gln His Leu Phe Gly
1               5                   10                  15

<210> SEQ ID NO 9
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Ser Trp Tyr Lys Gly Glu Arg Val Asp Gly Asn Arg Gln Ile
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Arg Gln Ile Ile Gly Tyr Val Ile Gly Thr Gln Gln Ala Thr
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Tyr Val Ile Gly Thr Gln Gln Ala Thr Pro Gly Pro Ala Tyr
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Pro Ala Tyr Ser Gly Arg Glu Ile Ile Tyr Pro Asn Ala Ser
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Arg Glu Ile Ile Tyr Pro Asn Ala Ser Leu Leu Ile Gln Asn
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Thr Gly Phe Tyr Thr Leu His Val Ile Lys Ser Asp Leu Val
```

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Tyr Thr Leu His Val Ile Lys Ser Asp Leu Val Asn Glu Glu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu His Val Ile Lys Ser Asp Leu Val Asn Glu Glu Ala Thr Gly
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ser Asp Leu Val Asn Glu Glu Ala Thr Gly Gln Phe Arg Val
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Phe Arg Val Tyr Pro Glu Leu Pro Lys Pro Ser Ile Ser Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Pro Ser Ile Ser Ser Asn Asn Ser Lys Pro Val Glu Asp Lys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic

```
                                 peptide

<400> SEQUENCE: 20

Tyr Leu Trp Trp Val Asn Asn Gln Ser Leu Pro Val Ser Pro Arg
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Asp Ser Val Ile Leu Asn Val Leu Tyr Gly Pro Asp Ala Pro
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Asn Val Leu Tyr Gly Pro Asp Ala Pro Thr Ile Ser Pro Leu
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Pro Thr Ile Ser Pro Leu Asn Thr Ser Tyr Arg Ser Gly Glu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Tyr Ser Trp Phe Val Asn Gly Thr Phe Gln Gln Ser Thr Gln
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Glu Leu Phe Ile Pro Asn Ile Thr Val Asn Asn Ser Gly Ser
1               5                   10                  15

<210> SEQ ID NO 26
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Thr Thr Val Thr Thr Ile Thr Val Tyr Ala Glu Pro Pro Lys
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Ile Thr Val Tyr Ala Glu Pro Pro Lys Pro Phe Ile Thr Ser
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Asp Pro Val Ile Leu Asn Val Leu Tyr Gly Pro Asp Asp Pro
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Tyr Thr Tyr Tyr Arg Pro Gly Val Asn Leu Ser Leu Ser Cys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Ser Trp Leu Ile Asp Gly Asn Ile Gln Gln His Thr Gln Glu
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

Asn Ser Gly Leu Tyr Thr Cys Gln Ala Asn Asn Ser Ala Ser Gly
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Thr Thr Val Lys Thr Ile Thr Val Ser Ala Glu Leu Pro Lys
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Ile Thr Val Ser Ala Glu Leu Pro Lys Pro Ser Ile Ser Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Leu Trp Trp Val Asn Gly Gln Ser Leu Pro Val Ser Pro Arg
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Cys Gly Ile Gln Asn Ser Val Ser Ala Asn Arg Ser Asp Pro
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Asn Ser Val Ser Ala Asn Arg Ser Asp Pro Val Thr Leu Asp
1               5                   10                  15

<210> SEQ ID NO 37
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 37

Ser Ser Tyr Leu Ser Gly Ala Asn Leu Asn Leu Ser Cys His Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Tyr Ser Trp Arg Ile Asn Gly Ile Pro Gln Gln His Thr Gln
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Asn Gly Ile Pro Gln Gln His Thr Gln Val Leu Phe Ile Ala
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn Gly Thr Tyr Ala Cys Phe Val Ser Asn Leu Ala Thr Gly Arg
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Ala Cys Phe Val Ser Asn Leu Ala Thr Gly Arg Asn Asn Ser
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Asn Ser Ile Val Lys Ser Ile Thr Val Ser Ala Ser Gly Thr
1               5                   10                  15
```

```
<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ile Thr Val Ser Ala Ser Gly Thr Ser Pro Gly Leu Ser Ala
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Pro Gly Leu Ser Ala Gly Ala Thr Val Gly Ile Met Ile Gly
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Val Gly Ile Met Ile Gly Val Leu Val Gly Val Ala Leu Ile
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

His Gln Leu Leu Cys Cys Glu Val Glu Thr Ile Arg Arg Ala Tyr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Ala Asn Leu Leu Asn Asp Arg Val Leu Arg Ala Met Leu Lys
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

Asn Asp Arg Val Leu Arg Ala Met Leu Lys Ala Glu Glu Thr Cys
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ala Met Leu Lys Ala Glu Glu Thr Cys Ala Pro Ser Val Ser
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Phe Lys Cys Val Gln Lys Glu Val Leu Pro Ser Met Arg Lys Ile
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Lys Glu Val Leu Pro Ser Met Arg Lys Ile Val Ala Thr Trp
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Pro Ser Met Arg Lys Ile Val Ala Thr Trp Met Leu Glu Val
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Met Arg Lys Ile Val Ala Thr Trp Met Leu Glu Val Cys Glu Glu
1               5                   10                  15

<210> SEQ ID NO 54
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 54

Met Leu Glu Val Cys Glu Glu Gln Lys Cys Glu Glu Glu Val Phe
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Glu Glu Val Phe Pro Leu Ala Met Asn Tyr Leu Asp Arg Phe
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Val Phe Pro Leu Ala Met Asn Tyr Leu Asp Arg Phe Leu Ser Leu
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Arg Phe Leu Ser Leu Glu Pro Val Lys Lys Ser Arg Leu Gln
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Glu Pro Val Lys Lys Ser Arg Leu Gln Leu Leu Gly Ala Thr
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Leu Gln Leu Leu Gly Ala Thr Cys Met Phe Val Ala Ser Lys
1               5                   10                  15
```

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Cys Met Phe Val Ala Ser Lys Met Lys Glu Thr Ile Pro Leu
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ser Lys Met Lys Glu Thr Ile Pro Leu Thr Ala Glu Lys Leu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Ile Pro Leu Thr Ala Glu Lys Leu Cys Ile Tyr Thr Asp Asn
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Leu Cys Ile Tyr Thr Asp Asn Ser Ile Arg Pro Glu Glu Leu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Asn Ser Ile Arg Pro Glu Glu Leu Leu Gln Met Glu Leu Leu
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 65

Pro Glu Glu Leu Leu Gln Met Glu Leu Leu Leu Val Asn Lys Leu
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Glu Leu Leu Gln Met Glu Leu Leu Leu Val Asn Lys Leu Lys
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Leu Gln Met Glu Leu Leu Leu Val Asn Lys Leu Lys Trp Asn
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Glu Leu Leu Leu Val Asn Lys Leu Lys Trp Asn Leu Ala Ala
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Asn Lys Leu Lys Trp Asn Leu Ala Ala Met Thr Pro His Asp
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Trp Asn Leu Ala Ala Met Thr Pro His Asp Phe Ile Glu His
1               5                   10                  15

<210> SEQ ID NO 71
<211> LENGTH: 15
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 71

Trp Asn Leu Ala Ala Met Thr Pro His Asp Phe Ile Glu His Phe
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Pro His Asp Phe Ile Glu His Phe Leu Ser Lys Met Pro Glu Ala
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Asn Lys Gln Ile Ile Arg Lys His Ala Gln Thr Phe Val Ala Leu
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Ala Gln Thr Phe Val Ala Leu Cys Ala Thr Asp Val Lys Phe Ile
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Val Lys Phe Ile Ser Asn Pro Pro Ser Met Val Ala Ala Gly Ser
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Pro Pro Ser Met Val Ala Ala Gly Ser Val Val Ala Ala Val Gln
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Val Ala Ala Val Gln Gly Leu Asn Leu Arg Ser Pro Asn Asn Phe
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Glu Ala Leu Leu Glu Ser Ser Leu Arg Gln Ala Gln Gln Asn
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Ala Leu Leu Glu Ser Ser Leu Arg Gln Ala Gln Gln Asn Met
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Ala Ala Leu Cys Arg Trp Gly Leu Leu Ala Leu Leu Pro
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Gly Leu Leu Leu Ala Leu Leu Pro Pro Gly Ala Ala Ser Thr
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Leu Ala Leu Leu Pro Pro Gly Ala Ala Ser Thr Gln Val Cys
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Thr Asp Met Lys Leu Arg Leu Pro Ala Ser Pro Glu Thr His
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg His Leu Tyr Gln Gly Cys Gln Val Val Gln Gly Asn Leu Glu
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Cys Gln Val Val Gln Gly Asn Leu Glu Leu Thr Tyr Leu Pro
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asn Leu Glu Leu Thr Tyr Leu Pro Thr Asn Ala Ser Leu Ser Phe
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Thr Tyr Leu Pro Thr Asn Ala Ser Leu Ser Phe Leu Gln Asp
1               5                   10                  15

<210> SEQ ID NO 88
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ile Gln Glu Val Gln Gly Tyr Val Leu Ile Ala His Asn Gln Val
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Tyr Val Leu Ile Ala His Asn Gln Val Arg Gln Val Pro Leu Gln
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

His Asn Gln Val Arg Gln Val Pro Leu Gln Arg Leu Arg Ile Val
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Arg Gln Val Pro Leu Gln Arg Leu Arg Ile Val Arg Gly Thr
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Thr Gln Leu Phe Glu Asp Asn Tyr Ala Leu Ala Val Leu Asp
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Asp Pro Leu Asn Asn Thr Thr Pro Val Thr Gly Ala Ser Pro
```

-continued

```
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Thr Pro Val Thr Gly Ala Ser Pro Gly Gly Leu Arg Glu Leu
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Pro Gly Gly Leu Arg Glu Leu Gln Leu Arg Ser Leu Thr Glu Ile
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Glu Ile Leu Lys Gly Gly Val Leu Ile Gln Arg Asn Pro Gln
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Val Leu Ile Gln Arg Asn Pro Gln Leu Cys Tyr Gln Asp
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asn Pro Gln Leu Cys Tyr Gln Asp Thr Ile Leu Trp Lys Asp Ile
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 99

Ile Cys Glu Leu His Cys Pro Ala Leu Val Thr Tyr Asn Thr Asp
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Thr Asp Val Gly Ser Cys Thr Leu Val Cys Pro Leu His Asn
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Tyr Gly Leu Gly Met Glu His Leu Arg Glu Val Arg Ala Val
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Met Glu His Leu Arg Glu Val Arg Ala Val Thr Ser Ala Asn Ile
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Arg Glu Val Arg Ala Val Thr Ser Ala Asn Ile Gln Glu Phe
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Cys Lys Lys Ile Phe Gly Ser Leu Ala Phe Leu Pro Glu Ser Phe
1               5                   10                  15

<210> SEQ ID NO 105

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Pro Glu Ser Phe Asp Gly Asp Pro Ala Ser Asn Thr Ala Pro Leu
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Thr Ala Pro Leu Gln Pro Glu Gln Leu Gln Val Phe Glu Thr Leu
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ile Thr Gly Tyr Leu Tyr Ile Ser Ala Trp Pro Asp Ser Leu Pro
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Pro Asp Ser Leu Pro Asp Leu Ser Val Phe Gln Asn Leu Gln Val
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Leu Ser Val Phe Gln Asn Leu Gln Val Ile Arg Gly Arg Ile Leu
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110
```

Asn Leu Gln Val Ile Arg Gly Arg Ile Leu His Asn Gly Ala Tyr
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Gly Arg Ile Leu His Asn Gly Ala Tyr Ser Leu Thr Leu Gln
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Leu Thr Leu Gln Gly Leu Gly Ile Ser Trp Leu Gly Leu Arg
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Leu Gly Ile Ser Trp Leu Gly Leu Arg Ser Leu Arg Glu Leu
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Leu Arg Ser Leu Arg Glu Leu Gly Ser Gly Leu Ala Leu Ile His
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Leu Ala Leu Ile His His Asn Thr His Leu Cys Phe Val His
1               5                   10                  15

<210> SEQ ID NO 116
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 116

Asn Thr His Leu Cys Phe Val His Thr Val Pro Trp Asp Gln Leu
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Glu Cys Val Gly Glu Gly Leu Ala Cys His Gln Leu Cys Ala
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly His Cys Trp Gly Pro Gly Pro Thr Gln Cys Val Asn Cys Ser
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Gln Phe Leu Arg Gly Gln Glu Cys Val Glu Glu Cys Arg Val
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Glu Cys Arg Val Leu Gln Gly Leu Pro Arg Glu Tyr Val Asn Ala
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Gln Gly Leu Pro Arg Glu Tyr Val Asn Ala Arg His Cys Leu
1               5                   10                  15
```

```
<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Pro Ser Gly Val Lys Pro Asp Leu Ser Tyr Met Pro Ile Trp Lys
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Ser Pro Leu Thr Ser Ile Ile Ser Ala Val Val Gly Ile Leu
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ile Ser Ala Val Val Gly Ile Leu Leu Val Val Val Leu Gly Val
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ile Leu Leu Val Val Val Leu Gly Val Val Phe Gly Ile Leu Ile
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Leu Gly Val Val Phe Gly Ile Leu Ile Lys Arg Arg Gln Gln
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127
```

```
Gln Gln Lys Ile Arg Lys Tyr Thr Met Arg Arg Leu Leu Gln Glu
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Arg Lys Tyr Thr Met Arg Arg Leu Leu Gln Glu Thr Glu Leu
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Met Arg Ile Leu Lys Glu Thr Glu Leu Arg Lys Val Lys Val Leu
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Glu Thr Glu Leu Arg Lys Val Lys Val Leu Gly Ser Gly Ala Phe
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Val Lys Val Leu Gly Ser Gly Ala Phe Gly Thr Val Tyr Lys
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Glu Asn Val Lys Ile Pro Val Ala Ile Lys Val Leu Arg Glu
1               5                   10                  15

<210> SEQ ID NO 133
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 133

Lys Ile Pro Val Ala Ile Lys Val Leu Arg Glu Asn Thr Ser Pro
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Tyr Val Met Ala Gly Val Gly Ser Pro Tyr Val Ser Arg Leu
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Met Ala Gly Val Gly Ser Pro Tyr Val Ser Arg Leu Leu Gly Ile
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Arg Leu Leu Gly Ile Cys Leu Thr Ser Thr Val Gln Leu Val
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Thr Val Gln Leu Val Thr Gln Leu Met Pro Tyr Gly Cys Leu Leu
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Gly Arg Leu Gly Ser Gln Asp Leu Leu Asn Trp Cys Met Gln
1               5                   10                  15
```

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Leu Leu Asn Trp Cys Met Gln Ile Ala Lys Gly Met Ser Tyr Leu
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Cys Met Gln Ile Ala Lys Gly Met Ser Tyr Leu Glu Asp Val Arg
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Gly Met Ser Tyr Leu Glu Asp Val Arg Leu Val His Arg Asp Leu
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Val Arg Leu Val His Arg Asp Leu Ala Ala Arg Asn Val Leu Val
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

His Arg Asp Leu Ala Ala Arg Asn Val Leu Val Lys Ser Pro Asn
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 144

Ala Arg Asn Val Leu Val Lys Ser Pro Asn His Val Lys Ile Thr
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Ile Lys Trp Met Ala Leu Glu Ser Ile Leu Arg Arg Arg Phe
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Lys Trp Met Ala Leu Glu Ser Ile Leu Arg Arg Arg Phe Thr
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Glu Ser Ile Leu Arg Arg Arg Phe Thr His Gln Ser Asp Val Trp
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Asp Val Trp Ser Tyr Gly Val Thr Val Trp Glu Leu Met Thr
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Val Thr Val Trp Glu Leu Met Thr Phe Gly Ala Lys Pro Tyr
1               5                   10                  15

<210> SEQ ID NO 150
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 150

Val Trp Glu Leu Met Thr Phe Gly Ala Lys Pro Tyr Asp Gly Ile
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Lys Pro Tyr Asp Gly Ile Pro Ala Arg Glu Ile Pro Asp Leu
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ile Cys Thr Ile Asp Val Tyr Met Ile Met Val Lys Cys Trp Met
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Val Tyr Met Ile Met Val Lys Cys Trp Met Ile Asp Ser Glu
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Pro Arg Phe Arg Glu Leu Val Ser Glu Phe Ser Arg Met Ala
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Phe Arg Glu Leu Val Ser Glu Phe Ser Arg Met Ala Arg Asp Pro
1               5                   10                  15
```

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Phe Ser Arg Met Ala Arg Asp Pro Gln Arg Phe Val Val Ile Gln
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asp Gly Asp Leu Gly Met Gly Ala Ala Lys Gly Leu Gln Ser Leu
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Lys Gly Leu Gln Ser Leu Pro Thr His Asp Pro Ser Pro Leu
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Gln Arg Tyr Ser Glu Asp Pro Thr Val Pro Leu Pro Ser Glu
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Pro Glu Tyr Val Asn Gln Pro Asp Val Arg Pro Gln Pro Pro Ser
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 161

Glu Gly Pro Leu Pro Ala Ala Arg Pro Ala Gly Ala Thr Leu Glu
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Ala Thr Leu Glu Arg Pro Lys Thr Leu Ser Pro Gly Lys Asn
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Lys Asp Val Phe Ala Phe Gly Gly Ala Val Glu Asn Pro Glu Tyr
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Leu Pro Arg Val Gly Cys Pro Ala Leu Pro Leu Pro Pro Pro Pro
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Leu Pro Leu Pro Pro Pro Pro Leu Leu Pro Leu Leu Pro Leu
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Pro Pro Leu Leu Pro Leu Leu Pro Leu Leu Leu Leu Leu Leu
1               5                   10                  15

<210> SEQ ID NO 167
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Leu Pro Leu Leu Pro Leu Leu Leu Leu Leu Gly Ala Ser
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Pro Leu Leu Leu Leu Leu Leu Gly Ala Ser Gly Gly Gly Gly Gly
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Glu Val Leu Phe Arg Cys Pro Pro Cys Thr Pro Glu Arg Leu
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Pro Glu Arg Leu Ala Ala Cys Gly Pro Pro Val Ala Pro Pro
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Pro Pro Pro Val Ala Pro Pro Ala Ala Val Ala Ala Val Ala Gly
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Ala Arg Met Pro Cys Ala Glu Leu Val Arg Glu Pro Gly Cys
```

```
                1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Cys Ala Glu Leu Val Arg Glu Pro Gly Cys Gly Cys Cys Ser Val
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Cys Ala Arg Leu Glu Gly Glu Ala Cys Gly Val Tyr Thr Pro Arg
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Glu Leu Pro Leu Gln Ala Leu Val Met Gly Glu Gly Thr Cys Glu
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gln Ala Leu Val Met Gly Glu Gly Thr Cys Glu Lys Arg Arg Asp
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Glu Gly Gly Leu Val Glu Asn His Val Asp Ser Thr Met Asn
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 178

Thr Met Asn Met Leu Gly Gly Gly Gly Ser Ala Gly Arg Lys Pro
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Leu Lys Ser Gly Met Lys Glu Leu Ala Val Phe Arg Glu Lys Val
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Lys Glu Leu Ala Val Phe Arg Glu Lys Val Thr Glu Gln His Arg
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Glu Leu Ala Val Phe Arg Glu Lys Val Thr Glu Gln His Arg Gln
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Glu Lys Val Thr Glu Gln His Arg Gln Met Gly Lys Gly Gly
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Lys His His Leu Gly Leu Glu Glu Pro Lys Lys Leu Arg Pro
1               5                   10                  15

<210> SEQ ID NO 184

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Lys His His Leu Gly Leu Glu Glu Pro Lys Lys Leu Arg Pro Pro
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Glu Pro Lys Lys Leu Arg Pro Pro Ala Arg Thr Pro Cys Gln
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Leu Asp Gln Val Leu Glu Arg Ile Ser Thr Met Arg Leu Pro Asp
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Thr Met Arg Leu Pro Asp Glu Arg Gly Pro Leu Glu His Leu Tyr
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Glu Arg Gly Pro Leu Glu His Leu Tyr Ser Leu His Ile Pro Asn
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

```
Gly Leu Tyr Asn Leu Lys Gln Cys Lys Met Ser Leu Asn Gly Gln
1               5                   10                  15
```

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

```
Thr Gly Lys Leu Ile Gln Gly Ala Pro Thr Ile Arg Gly Asp Pro
1               5                   10                  15
```

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

```
Ala Pro Thr Ile Arg Gly Asp Pro Glu Cys His Leu Phe Tyr Asn
1               5                   10                  15
```

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

```
Cys His Leu Phe Tyr Asn Glu Gln Gln Glu Ala Arg Gly Val His
1               5                   10                  15
```

<210> SEQ ID NO 193
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

```
Gly Pro Gly Pro Gly
1               5
```

<210> SEQ ID NO 194
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

```
Pro Gly Pro Gly Pro
1               5
```

<210> SEQ ID NO 195
<211> LENGTH: 22
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: This sequence may encompass 0-11 "Gly Pro"
      repeating units

<400> SEQUENCE: 195

Gly Pro Gly Pro Gly Pro Gly Pro Gly Pro Gly Pro Gly Pro Gly Pro
1               5                   10                  15

Gly Pro Gly Pro Gly Pro
            20

<210> SEQ ID NO 196
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 0-11 "Pro Gly"
      repeating units

<400> SEQUENCE: 196

Pro Gly Pro Gly Pro Gly Pro Gly Pro Gly Pro Gly Pro Gly Pro Gly
1               5                   10                  15

Pro Gly Pro Gly Pro Gly
            20

<210> SEQ ID NO 197
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(22)
<223> OTHER INFORMATION: This region may encompass 0-11 "Gly Pro"
      repeating units

<400> SEQUENCE: 197

Gly Pro Gly Pro Gly Pro Gly Pro Gly Pro Gly Pro Gly Pro Gly Pro
1               5                   10                  15

Gly Pro Gly Pro Gly Pro Gly
            20

<210> SEQ ID NO 198
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(22)
<223> OTHER INFORMATION: This region may encompass 0-11 "Pro Gly"
      repeating units

<400> SEQUENCE: 198

Pro Gly Pro Gly Pro Gly Pro Gly Pro Gly Pro Gly Pro Gly Pro Gly
1               5                   10                  15

Pro Gly Pro Gly Pro Gly Pro
            20
```